(12) United States Patent
Albrecht et al.

(10) Patent No.: US 9,505,767 B2
(45) Date of Patent: Nov. 29, 2016

(54) PYRAZOLO[1,5-A]PYRIMIDIN-7(4H)-ONEHISTONE DEMETHYLASE INHIBITORS

(71) Applicants: Genentech, Inc., South San Francisco, CA (US); Constellation Pharmaceuticals, Inc., Cambridge, MA (US)

(72) Inventors: Brian K. Albrecht, Cambridge, MA (US); Steven F. Bellon, Wellesley, MA (US); Victor S. Gehling, Somerville, MA (US); Jean-Christophe Harmange, Andover, MA (US); Yves LeBlanc, Kirkland (CA); Jun Liang, South San Francisco, CA (US); Steven R. Magnuson, South San Francisco, CA (US); Vickie Hsiao-Wei Tsui, South San Francisco, CA (US); Birong Zhang, South San Francisco, CA (US)

(73) Assignees: Genentech, Inc., South San Francisco, CA (US); Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/477,566

(22) Filed: Sep. 4, 2014

(65) Prior Publication Data
US 2015/0065522 A1 Mar. 5, 2015

Related U.S. Application Data

(60) Provisional application No. 61/874,310, filed on Sep. 5, 2013.

(51) Int. Cl.
| | | |
|---|---|---|
| *C07D 487/04* | (2006.01) | |
| *A61K 31/519* | (2006.01) | |
| *A61K 45/06* | (2006.01) | |
| *A61N 5/10* | (2006.01) | |

(52) U.S. Cl.
CPC ........... *C07D 487/04* (2013.01); *A61K 31/519* (2013.01); *A61K 45/06* (2013.01); *A61N 5/10* (2013.01)

(58) Field of Classification Search
CPC .................................................. C07D 471/04
See application file for complete search history.

(56) References Cited

U.S. PATENT DOCUMENTS

| | | |
|---|---|---|
| 2007/0072881 A1 | 3/2007 | Guzi et al. |
| 2012/0088775 A1 | 4/2012 | Zhang et al. |
| 2012/0277224 A1 | 11/2012 | Mccall et al. |
| 2014/0275092 A1 | 9/2014 | Albrecht et al. |

FOREIGN PATENT DOCUMENTS

| | | | |
|---|---|---|---|
| EP | 0531901 A2 | 3/1993 | |
| EP | 1238979 A1 | 9/2002 | |
| WO | WO 03/101993 A1 | 12/2003 | |
| WO | WO 2010/086040 A1 | 8/2010 | |
| WO | WO 2012149157 A2 * | 11/2012 | ........... A61K 31/519 |
| WO | WO 2014/066795 A1 | 5/2014 | |

OTHER PUBLICATIONS

STN-Chemical database registry # 908524-37-8 for 2,5-dimethyl-3-(2-thienyl)-Pyrazolo[1,5-a]pyrimidin-7(4H)-one, Entered STN: Sep. 26, 2006.*
Online "http://web.archive.org/web/20090414214134/http://www.htscompounds.com/index.html" dated Apr. 14, 2009, accessed Aug. 21, 2015.*
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
Online "http://web.archive.org/web/20031225052253/http://www.specs.net/", accessed Apr. 1, 2015.*
Hamada "Design, Synthesis, Enzyme-Inhibitory Activity, and Effect on Human Cancer Cells of a Novel Series of Jumonji Domain-Containing Protein 2 Histone Demethylase Inhibitors" J. Med. Chem. 2010, 53, 5629-5638.*
Rotili "Pan-Histone Demethylase Inhibitors Simultaneously Targeting Jumonji C and Lysine-Specific Demethylases Display High Anticancer Activities" J. Med. Chem. 2014, 57, 42-55.*
Pozharskii et. al. Heterocycles in Life and Society Wiley, 1997, pp. 1-6.*
Pitt "Heteroaromatic Rings of the Future" J. Med. Chem. 2009, 52, 2952-2963.*
Online "http://web.archive.org/web/20061103222641/http://www.lifechemicals.com/eng/order/" dated Nov. 3, 2006 accessed Jan. 12, 2016.*
STN-Chemical database registry # 946212-74-4 for Pyrazolo[1,5-a]pyrimidin-7(4H)-one, 5-(chloromethyl)-3-[3-(3,4-
(Continued)

(Continued)

*Primary Examiner* — David K O'Dell
(74) *Attorney, Agent, or Firm* — Viksnins Harris & Padys PLLP

(57) ABSTRACT

The present invention relates to compounds formula (I):

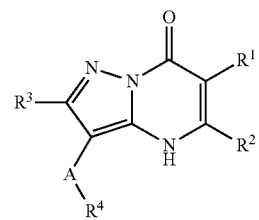

and to salts thereof, wherein $R^1$-$R^4$ and A have any of the values defined in the specification, and compositions and uses thereof. The compounds are useful as inhibitors of histone demethylases, such as KDM5. Also included are pharmaceutically acceptable compositions comprising the compounds of the present invention and methods of using said compositions in the treatment of various disorders.

3 Claims, No Drawings

(56) References Cited

OTHER PUBLICATIONS dimethoxyphenyl)-1,2,4-oxadiazol-5-yl]-2-(methylthio)-, Entered STN: Sep. 7, 2007.*

Borisov et al., "Parallel Liquid-Phase Synthesis of 5-(1H-4-Pyrazolyl)-[1,2,4]oxadiazole Libraries", *J. Comb. Chem.*, 11, 1023-1029 (2009).

Ibrahim et al., "Synthesis and biological activities of some new fully fused quinazoline derivatives", *Indian Journal of Chemistry*, vol. 37B, 62-67 (1998).

Patent Cooperation Treaty, International Searching Authority, Search Report and Written Opinion for PCT/US2014/054114, 13 pages, Jan. 20, 2015.

Qi et al., "Design, synthesis and biological activity of pyrazolo[1,5-a]pyrimidin-7(4H)-ones as novel Kv7/KCNQ potassium channel activators", *European Journal of Medicinal Chemistry 46*, 934-943 (2011).

Selleri et al., "Synthesis, benzodiazepine receptor affinity and in vivo testing of 3-aryl-4, 7-dihydro-6-($N^{1'}$-alkylpyrazolo-3'-or 5'-yl)pyrazolo[1,5-a]pyrimidin-7-ones", *Eur J Med Chem 32*, 941-953 (1997).

Selleri et al., "Synthesis and Benzodiazepine Receptor Affinity of Pyrazolo[1,5-a]pyrimidine Derivatives. 3. New 6-(3-Thienyl) Series as α1 Selective Ligands", *J. Med. Chem. 46*, 310-313 (2003).

Sharma et al., "A chromatin-mediated reversible drug tolerant state in cancer cell subpopulations", *Cell 141* (1), 69-80 (2010).

Wang et al., "Indazolylpyrazolopyrimidine as Highly Potent B-Raf Inhibitors with in Vivo Activity", *J. Med. Chem.*, 53, 7874-7878 (2010).

\* cited by examiner

PYRAZOLO[1,5-A]PYRIMIDIN-7(4H)-ONE HISTONE DEMETHYLASE INHIBITORS

CROSS-REFERENCE TO RELATED APPLICATION

This patent application claims the benefit of priority of U.S. application Ser. No. 61/874,310, filed Sep. 5, 2013, which application is herein incorporated by reference.

TECHNICAL FIELD OF THE INVENTION

The present invention relates to compounds useful as inhibitors of histone demethylases, such as KDM5.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding or chromatin-modifying enzymes. Significantly, an increasing number of these enzymes have been associated with a variety of disorders such as cancer. Thus, therapeutic agents directed against this emerging class of gene regulatory enzymes promise new approaches to the treatment of human diseases.

Additionally, the relatively rapid acquisition of resistance to cancer drugs remains a key obstacle to successful cancer therapy. Substantial efforts to elucidate the molecular basis for such drug resistance have revealed a variety of mechanisms, including drug efflux, acquisition of drug binding-deficient mutants of the target, engagement of alternative survival pathways and epigenetic alterations. Rare, stochastic, resistance-conferring genetic alterations have been found within a tumor cell population selected during drug treatment. See Sharma et al., *Cell* 141(1):69-80 (2010). The KDM5/JARID1 family of histone demethylases was found to play a role in cancer resistance. The KDM5/JARID1 family of demethylases in humans contains four members, KDM5A, KDM5B, KDM5C and KDM5D. KDM5 family members contain five conserved domains: JmjN, ARID, JmjC, PHD and a $C_5HC_2$ zinc finger. Amino acid sequences of KDM5A, KDM5B, KDM5C and KDM5D are known and are publicly available, e.g., see UniProtKB/Swiss-Prot (see e.g., KDM5A (e.g., P29375-1 and P29375-2), KDM5B (e.g., Q9UGL1-1 and Q9UGL1-2), KDM5C (e.g., P41229-1, P41229-2, P41229-3 and P41229-4) and KDM5D (e.g., Q9BY66-1, Q9BY66-2 and Q9BY66-3). There is currently a need for compounds that inhibit of KDM5 demethylases for treating hyperproliferative diseases, preventing drug resistance, and/or for improving the efficacy of other cancer treatments (e.g. targeted therapies, chemotherapies, and radiotherapies.

SUMMARY OF THE INVENTION

One aspect includes the use of a compound of formula (I):

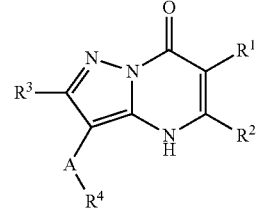

or a pharmaceutically acceptable salt thereof, wherein:

$R^1$ and $R^2$ are each independently H, $C_{1-12}$alkyl, $C_{2-12}$alkenyl, $C_{2-12}$alkynyl, carbocyclyl, heterocyclyl, halo, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —C=$NOR^a$, —$C(=N(R^a))N(R^a)_2$, —$OC(O)R^a$, or —$OC(O)N(R^a)_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups $R^x$; and wherein $R^1$ and $R^2$ are not each H; or $R^1$ and $R^2$ taken together with the atoms to which they are attached form a 4, 5, 6, 7, or 8 membered carbocyclyl, which carbocyclyl is optionally substituted with one or more groups $R^x$;

$R^3$ is H, $C_{1-6}$alkyl, trifluoromethyl, 3-6 membered carbocyclyl, 3-6 membered heterocyclyl, halo, —$OR^f$, —$SR^f$, —$N(R^f)_2$, —CN, or —$NO_2$, wherein said alkyl, carbocyclyl and heterocyclyl are optionally substituted with one or more groups independently selected from oxo, halo, $C_{1-3}$alkoxy and $C_{1-3}$alkyl;

$R^4$ is H, $C_{2-12}$alkenyl, $C_{2-12}$alkynyl, carbocyclyl, heterocyclyl, halo, —$OR^g$, —$SR^g$, —$N(R^g)_2$, —CN, —$NO_2$, —$C(O)R^g$, —$CO_2R^g$, —$C(O)N(R^g)_2$, —$C(O)SR^g$, —$C(O)C(O)R^g$, —$C(O)CH_2C(O)R^g$, —$C(S)N(R^g)_2$, —$C(S)OR^g$, —$S(O)R^g$, —$SO_2R^g$, —$SO_2N(R^g)_2$, —$N(R^g)C(O)R^g$, —$N(R^g)C(O)N(R^g)_2$, —$N(R^g)SO_2R^g$, —$N(R^g)SO_2N(R^g)_2$, —$N(R^g)N(R^h)_2$, —$N(R^g)C(=N(R^g))N(R^g)_2$, —$C(=N)N(R^g)_2$, —C=$NOR^g$, —$C(=N(R^g))N(R^g)_2$, —$OC(O)R^g$, or —$OC(O)N(R^g)_2$, wherein each $C_{1-12}$alkyl, $C_{2-12}$alkenyl, $C_{2-12}$alkynyl, carbocyclyl, and heterocyclyl of $R^4$ is optionally substituted with one or more groups $R^x$;

$R^5$ is H, $C_{2-12}$alkenyl, $C_{2-12}$alkynyl, carbocyclyl, and heterocyclyl, wherein each $C_{1-12}$alkyl, $C_{2-12}$alkenyl, $C_{2-12}$alkynyl, carbocyclyl, and heterocyclyl is optionally substituted with one or more groups independently selected from oxo, $C_{1-12}$ alkyl, $C_{1-12}$haloalkyl, carbocyclyl, heterocyclyl, halo, —CN, —$NO_2$, —$NR^mR^m$, —$OR^m$, —$C(=O)OR^m$, and —$OC(=O)R^m$; or $R^5$ and $R^2$ taken together with the atoms to which they are attached form a heterocyclyl;

each $R^a$ is independently selected from H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups $R^x$;

each $R^f$ is independently selected from H, $C_{1-3}$ alkyl, trifluoromethyl, 3-6 membered carbocyclyl, and 3-6 membered heterocyclyl; or two $R^f$ groups together with the nitrogen to which they are attached form a 3-6 membered heterocycle;

each $R^g$ is independently selected from H, $C_{1-6}$alkyl, $C_{2-6}$alkenyl, $C_{2-6}$alkynyl, $C_{3-8}$carbocyclyl, and heterocyclyl, wherein each $C_{1-6}$alkyl, $C_{2-6}$alkenyl, $C_{2-6}$alkynyl, $C_{3-8}$carbocyclyl, and heterocyclyl is optionally substituted with one or more groups $R^x$; or two $R^g$ groups together with the nitrogen to which they are attached form a 3-6 membered heterocycle;

each $R^m$ is independently selected from H, $C_{1-6}$alkyl, $C_{2-6}$alkenyl, $C_{2-6}$alkynyl, $C_{1-6}$haloalkyl, carbocyclyl, $C_{1-6}$ alkanoyl, phenyl, and benzyl, wherein any $C_{1-6}$alkyl, $C_{2-6}$alkenyl, $C_{2-6}$alkynyl, $C_{1-6}$haloalkyl, carbocyclyl, $C_{1-6}$ alkanoyl, phenyl, or benzyl is optionally substituted with one or more groups independently selected from halo, —CN, —NO$_2$, —NR$^y$R$^z$, and —OR$^w$; or two R$^m$ groups together with the nitrogen to which they are attached form a 3-6 membered heterocycle;

A is a monocyclic or bicyclic heteroaryl ring that is substituted with $R^4$ and that is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, —OR$^t$, —C(O)R$^t$, —COO, —OC(O)R$^t$, —N(R$^t$)$_2$, and carbocyclyl;

each $R^t$ is independently selected from H, $C_{1-6}$alkyl, $C_{2-6}$alkenyl, $C_{2-6}$alkynyl, $C_{3-8}$carbocyclyl, and heterocyclyl, wherein each $C_{1-6}$alkyl, $C_{2-6}$alkenyl, $C_{2-6}$alkynyl, $C_{3-8}$carbocyclyl, and heterocyclyl is optionally substituted with one or more groups $R^x$; or two $R^t$ groups together with the nitrogen to which they are attached form a 3-6 membered heterocycle;

each $R^v$ is independently hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, halo, amino, hydroxyl, and $C_1$-$C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^w$ is independently selected from H, $C_{1-4}$alkyl, $C_{1-4}$alkanoyl, phenyl, benzyl, and phenethyl;

each $R^x$ is independently selected from oxo, $C_{1-6}$alkyl, $C_{2-6}$alkenyl, $C_{2-6}$alkynyl, $C_{1-6}$haloalkyl, carbocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —S(O)$_2$—N(R$^v$)$_2$, —N(R$^v$)—C(O)—R$^v$, —N(R$^v$)—S(O)—R$^v$, —N(R$^v$)—S(O)$_2$—R$^v$, —N(R$^v$), —S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, $C_{1-6}$haloalkyl and carbocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —S(O)$_2$—N(R$^v$)$_2$, —N(R$^v$)—C(O)—R$^v$, —N(R$^v$)—S(O)—R$^v$—N(R$^v$)—S(O)$_2$—R$^v$ and $C_{1-6}$alkyl that is optionally substituted with one or more groups independently selected from oxo and halo; and each $R^y$ and $R^z$ is independently selected from H, $C_{1-4}$alkyl, $C_{1-4}$alkanoyl, $C_{1-4}$alkoxycarbonyl, phenyl, benzyl, and phenethyl, or $R^y$ and $R^z$ together with the nitrogen to which they are attached form a heterocyclyl;

for the prophylactic or therapeutic treatment of a proliferative disorder (e.g. cancer).

Another aspect includes a composition, comprising a compound of formula (I) or a pharmaceutically acceptable salt thereof, and a pharmaceutically acceptable adjuvant, carrier, or vehicle.

Another aspect includes compounds and compositions for treating diseases, disorders or conditions associated with KDM5 activity. Such diseases, disorders, or conditions include those described herein.

Another aspect includes a compound of formula (I) and salts thereof.

Another aspect includes a pharmaceutical composition comprising a compound of formula (I) or a pharmaceutically acceptable salt thereof.

Another aspect includes a method of treating a disease associated with KDM5 activity, comprising administering an therapeutically effective amount of a compound of formula (I), or a pharmaceutically acceptable salt thereof, to a patient in need thereof.

Another aspect includes the use of a compound of formula (I), or a pharmaceutically acceptable salt thereof, in therapy. Another aspect includes the use of a pharmaceutical composition comprising a compound of formula (I), or a pharmaceutically acceptable salt thereof, in therapy.

Another aspect includes the use of a compound of formula (I), or a pharmaceutically acceptable salt thereof, in treating a disease associated with KDM5 activity. Another aspect includes the use of a pharmaceutical composition comprising a compound of formula (I), or a pharmaceutically acceptable salt thereof, in treating a disease associated with KDM5 activity.

Another aspect includes the use of a compound of formula (I), or a pharmaceutically acceptable salt thereof, in the manufacture of a medicament for the treatment of a disease associated with KDM5 activity. Another aspect includes the use of a pharmaceutical composition comprising a compound of formula (I), or a pharmaceutically acceptable salt thereof, in the manufacture of a medicament for the treatment of a disease associated with KDM5 activity.

Another aspect includes a method of increasing the efficacy of a cancer treatment comprising a cancer therapy agent, comprising administering to a patient (a) an effective amount of a compound of formula (I) or a pharmaceutically acceptable salt thereof, and (b) an effective amount of the cancer therapy agent.

Another aspect includes a method of treating an individual with cancer who has an increased likelihood of developing resistance to a cancer therapy agent comprising administering to the individual (a) an effective amount of a compound of formula (I) or a pharmaceutically acceptable salt thereof, and (b) an effective amount of the cancer therapy agent.

Another aspect includes compounds for the study of histone demethylases, such as KDM5, the study of intracellular signal transduction pathways mediated by such histone demethylases, and the comparative evaluation of modulators of these demethylases.

Another aspect includes a process for preparing a compound of formula I or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75th Ed.

Unless otherwise stated, compounds of formula I include enantiomeric, diastereomeric and geometric (or conformational)) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more: hydrogen by deuterium or tritium, carbon by $^{13}C$— or $^{14}C$ carbon, nitrogen by a $^{15}N$ nitrogen, sulfur by a $^{33}S$, $^{34}S$ or $^{36}S$ sulfur, or oxygen by a $^{17}O$ or $^{18}O$ oxygen. are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically—enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a Spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and Spiro carbocyclyls include spiro[2.2]pentane, spiro[2.3]hexane, spiro[2.4]heptane, spiro[2.5]octane and spiro[4.5]decane, each of which are independently optionally substituted with one or more groups described herein. The term carbocyclyl includes aryl ring systems as defined herein.

The term "alkyl," as used herein, refers to a saturated linear or branched-chain monovalent hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, heptyl, octyl, nonyl, decyl, undecyl and dodecyl.

The term "alkenyl," as used herein, denotes a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—$CH=CH_2$), prop-1-enyl (—$CH=CHCH_3$), prop-2-enyl (—$CH_2CH=CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched monovalent hydrocarbon radical with at least one carbon-carbon, triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched monovalent radical represented by the formula —OR in which R is alkyl, alkenyl, alkynyl or carbocyclyl. Alkoxy groups include methoxy, ethoxy, propoxy, isopropoxy, mono-, di- and tri-fluoromethoxy and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, phthalimidyl, naphthimidyl, phenantriidinyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S). A heterocyclyl can optionally be substituted with one or more substituents independently selected from those defined herein.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, SO$_2$), and any nitrogen heteroatom may optionally be quaternized (e.g. [NR$_4$]$^+$Cl$^-$, [NR$_4$]$^+$OH$^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6, 7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "inhibitor" refers to a compound that binds to and inhibits a KDM5 enzyme with measurable affinity and activity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, refer to a measurable reduction in activity of a KDM5 enzyme between: (i) a sample comprising a compound of formula I or composition thereof and such KDM5 enzyme, and (ii) an equivalent sample comprising such KDM5 enzyme, in the absence of said compound, or composition thereof.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein) or those in which the condition or disorder is to be prevented.

Exemplary Values

In one embodiment a compound of formula (I) or a salt thereof is provided, provided that:

when -A-R$^4$ is 2-pyridyl, 3-pyridyl, 4-piperidino-3-pyridyl, 4-hydroxy-3-pyridyl, 4-methoxy-3-pyridyl, 4-morpholino-3-pyridyl, 4-pyrrolidino-3-pyridyl, 6-fluoro-2-pyridyl, and R$^3$ is hydrogen, methyl, ethyl, or methoxy, then R$^1$ is not H;

when -A-R$^4$ is 2-thienyl and R$^3$ is trifluoromethyl, then R$^1$ is not H;

when $R^1$ and $R^2$ taken together with the atoms to which they are attached form a 5 membered carbocyclyl and -A-$R^4$ is 1-naphthyl, then $R^3$ is not methyl;

when $R^1$ is 2-hydroxyethyl, $R^2$ is methyl, and $R^3$ is methyl, then -A-$R^4$ is not 6-(N,N-dimethylamino)-4-methyl-3-pyridyl;

when $R^1$ is 3-thienyl, $R^2$ is hydrogen, $R^3$ is hydrogen, then -A-$R^4$ is not 2-pyridyl or 3-pyridyl;

when $R^1$ is hydrogen, $R^2$ is 3-nitrophenyl or 2,3,4,5-tetrafluorophenyl, and $R^3$ is trifluoromethyl, then -A-$R^4$ is not 2-thienyl;

when and $R^3$ is methylthio then -A-$R^4$ is not 1,2,4-oxadiazol-5-yl substituted with 4-methylphenyl, 4-chlorophenyl, phenyl, 3,4-methylenedioxyphenyl, or 2-thienyl; and when $R^2$ is H, $R^3$ is H, and -A-$R^4$ is 3-thienyl, then $R^1$ is not phenyl, 3-thienyl, 2-thienyl, 1H-pyrazol-3-yl, 1-methyl-1H-pyrazol-3-yl, 1-methyl-1H-pyrazol-5-yl, 1-ethyl-1H-pyrazol-3-yl, or 1-ethyl-1H-pyrazol-5-yl.

In certain embodiments $R^1$ is H, $C_{1-12}$alkyl, $C_{2-12}$alkenyl, $C_{2-12}$alkynyl, carbocyclyl, heterocyclyl, halo, —O$R^a$, —S$R^a$, —N($R^a$)$_2$, —CN, —NO$_2$, —C(O)$R^a$, —CO$_2R^a$, —C(O)N($R^a$)$_2$, —C(O)S$R^a$, —C(O)C(O)$R^a$, —C(O)CH$_2$C(O)$R^a$, —C(S)N($R^a$)$_2$, —C(S)O$R^a$, —S(O)$R^a$, —SO$_2R^a$, —SO$_2$N($R^a$)$_2$, —N($R^a$)C(O)$R^a$, —N($R^a$)C(O)N($R^a$)$_2$, —N($R^a$)SO$_2R^a$, —N($R^a$)SO$_2$N($R^a$)$_2$, —N($R^a$)N($R^a$)$_2$, —N($R^a$)C(=N($R^a$))N($R^a$)$_2$, —C(=N)N($R^a$)$_2$, —C=NO$R^a$, —C(=N($R^a$))N($R^a$)$_2$, —OC(O)$R^a$, or —OC(O)N($R^a$)$_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more In certain embodiments $R^1$ is $C_{1-12}$alkyl, $C_{2-12}$alkenyl, $C_{2-12}$alkynyl, carbocyclyl, heterocyclyl, halo, —O$R^a$, —S$R^a$, —N($R^a$)$_2$, —CN, —NO$_2$, —C(O)$R^a$, —CO$_2R^a$, —C(O)N($R^a$)$_2$, —C(O)S$R^a$, —C(O)C(O)$R^a$, —C(O)CH$_2$C(O)$R^a$, —C(S)N($R^a$)$_2$, —C(S)O$R^a$, —S(O)$R^a$, —SO$_2R^a$, —SO$_2$N($R^a$)$_2$, —N($R^a$)C(O)$R^a$, —N($R^a$)C(O)N($R^a$)$_2$, —N($R^a$)SO$_2R^a$, —N($R^a$)SO$_2$N($R^a$)$_2$, —N($R^a$)N($R^a$)$_2$, —N($R^a$)C(=N($R^a$))N($R^a$)$_2$, —C(=N)N($R^a$)$_2$, —C=NO$R^a$, —C(=N($R^a$))N($R^a$)$_2$, —OC(O)$R^a$, or —OC(O)N($R^a$)$_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups $R^x$.

In certain embodiments $R^1$ and $R^2$ taken together with the atoms to which they are attached form an optionally substituted 4, 5, 6, 7, or 8 membered carbocyclyl.

In certain embodiments $R^1$ is H, $C_{1-6}$alkyl, carbocyclyl, halo, or —CN, wherein any $C_{1-6}$alkyl or carbocyclyl is independently optionally substituted with one or more groups independently selected from carbocyclyl, halo, —CN, and —O—$R^v$.

In certain embodiments $R^1$ is H, methyl, ethyl, isopropyl, cyclopropyl, methoxy, fluoro, chloro, or cyano; or $R^1$ and $R^2$ taken together with the atoms to which they are attached form an optionally substituted 5 membered carbocyclyl.

In certain embodiments $R^2$ is H, $C_{1-12}$alkyl, $C_{2-12}$alkenyl, $C_{2-12}$alkynyl, carbocyclyl, heterocyclyl, halo, —O$R^a$, —S$R^a$, —N($R^a$), —CN, —NO$_2$, —C(O)$R^a$, —CO$_2R^a$, —C(O)N($R^a$)$_2$, —C(O)S$R^a$, —C(O)C(O)$R^a$, —C(O)CH$_2$C(O)$R^a$, —C(S)N($R^a$)$_2$, —C(S)O$R^a$, —S(O)$R^a$, —SO$_2R^a$, —SO$_2$N($R^a$)$_2$, —N($R^a$)C(O)$R^a$, —N($R^a$)C(O)N($R^a$)$_2$, —N($R^a$)SO$_2R^a$, —N($R^a$)SO$_2$N($R^a$)$_2$, —N($R^a$)N($R^a$)$_2$, —N($R^a$)C(=N($R^a$))N($R^a$)$_2$, —C(=N)N($R^a$)$_2$, —C=NO$R^a$, —C(=N($R^a$))N($R^a$)$_2$, —OC(O)$R^a$, or —OC(O)N($R^a$)$_2$, wherein each $C_{1-12}$alkyl, $C_{2-12}$alkynyl, carbocyclyl, and heterocyclyl of $R^1$ and $R^2$ is independently optionally substituted with one or more groups $R^x$.

In certain embodiments $R^2$ is $C_{1-12}$alkyl, $C_{2-12}$alkenyl, $C_{2-12}$alkynyl, carbocyclyl, heterocyclyl, halo, —O$R^a$, —S$R^a$, —N($R^a$), —CN, —NO$_2$, —C(O)$R^a$, —CO$_2R^a$, —C(O)N($R^a$)$_2$, —C(O)S$R^a$, —C(O)C(O)$R^a$, —C(O)CH$_2$C(O)$R^a$, —C(S)N($R^a$)$_2$, —C(S)O$R^a$, —S(O)$R^a$, —SO$_2R^a$, —SO$_2$N($R^a$)$_2$, —N($R^a$)C(O)$R^a$, —N($R^a$)C(O)N($R^a$)$_2$, —N($R^a$)SO$_2R^a$, —N($R^a$)SO$_2$N($R^a$)$_2$, —N($R^a$)N($R^a$)$_2$, —N($R^a$)C(=N($R^a$))N($R^a$)$_2$, —C(=N)N($R^a$)$_2$, —C=NO$R^a$, —C(=N($R^a$))N($R^a$)$_2$, —OC(O)$R^a$, or —OC(O)N($R^a$)$_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups $R^x$.

In certain embodiments $R^2$ is H, $C_{1-6}$alkyl, or aryl, wherein each $C_{1-6}$alkyl is optionally substituted with one or more groups independently selected from —O—$R^v$.

In certain embodiments $R^2$ is H, methyl, ethyl, isopropyl, hydroxymethyl, or phenyl; or $R^1$ and $R^2$ taken together with the atoms to which they are attached form an optionally substituted 5 membered carbocyclyl.

In certain embodiments, one of $R^1$ and $R^2$ are other than H.

In certain embodiments $R^3$ is H.

In certain embodiments $R^3$ is $C_{1-3}$ alkyl, trifluoromethyl, 3-6 (e.g. 3, 4, 5, or 6) membered carbocyclyl, 3-6 (e.g. 3, 4, 5, or 6) membered heterocyclyl, halo, hydroxyl, —O$R^f$, —SH, —S$R^f$, —N($R^f$)$_2$, —CN, or —NO$_2$.

In certain embodiments A is a 5 or 6 membered monocyclic heteroaryl ring that is substituted with $R^4$ and that is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, —O$R^t$, —C(O)$R^t$, —CO$_2R^t$, —OC(O)$R^t$, —N($R^t$)$_2$, and carbocyclyl.

In certain embodiments A is a 9 or 10 membered bicyclic heteroaryl ring that is substituted with $R^4$ and that is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, —C(O)$R^t$, —CO$_2R^t$, —OC(O)$R^t$, —N($R^t$)$_2$, and carbocyclyl.

In certain embodiments A is a 5-membered heteroaryl ring comprising 1, 2, 3, or 4 heteroatoms that is substituted with $R^4$ and that is also optionally substituted with one or more groups independently selected from halo, nitro, cyano, $C_{1-6}$alkyl, $C_{2-4}$alkenyl, $C_{2-6}$alkynyl, $C_{1-6}$haloalkyl, —C(O)$R^t$, —CO$_2R^t$, —OC(O)$R^t$, —N($R^t$)$_2$, and carbocyclyl.

In certain embodiments A is a 5-membered heteroaryl ring comprising 1, 2, 3, or 4 nitrogen atoms, which ring is substituted with $R^4$ and which ring is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, —O$R^t$, —C(O)$R^t$, —CO$_2R^t$, —OC(O)$R^t$, —N($R^t$)$_2$, and carbocyclyl.

In certain embodiments A is a 5-membered heteroaryl ring comprising one heteroatom, which ring is substituted with $R^4$ and which ring is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, —O$R^t$, —C(O)$R^t$, —C(O)$_2R^t$, —OC(O)$R^t$, —N($R^t$)$_2$, and carbocyclyl.

In certain embodiments A is a 5-membered heteroaryl ring comprising two heteroatoms, which ring is substituted with $R^4$ and which ring is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, —OR$^t$, —C(O)R$^t$, —CO$_2$R$^t$, —OC(O)R$^t$, —N(R$^t$)$_2$, and carbocyclyl.

In certain embodiments A is a 5-membered heteroaryl ring comprising three heteroatoms, which ring is substituted with R$^4$ and which ring is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, —C(O)R$^t$, —CO$_2$R$^t$, —OC(O)R$^t$, —N(R$^t$)$_2$, and carbocyclyl.

In certain embodiments A is a pyrazole, imidazole, oxadiazole, or isoxazole ring, which pyrazole, imidazole, oxadiazole, or isoxazole ring is substituted with R$^4$ and which pyrazole, imidazole, oxadiazole, or isoxazole ring is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, C$_{1-6}$alkoxy, C$_{1-6}$alkanoyl, C$_{1-6}$alkanoyloxy, C$_{1-6}$alkoxycarbonyl, carbocyclyl, and —N(R$^t$)$_2$.

In certain embodiments A is a pyrazole ring which is substituted with R$^4$ and which is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, C$_{1-6}$alkoxy, C$_{1-6}$alkanoyl, C$_{1-6}$alkanoyloxy, C$_{1-6}$alkoxycarbonyl, C$_{3-8}$-carbocyclyl, and —N(R$^t$)$_2$.

In certain embodiments A is an imidazole ring which is substituted with R$^4$ and which is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, C$_{1-6}$alkoxy, C$_{1-6}$alkanoyl, C$_{1-6}$alkanoyloxy, C$_{1-6}$alkoxycarbonyl, C$_{3-8}$-carbocyclyl, and —N(R$^t$)$_2$.

In certain embodiments A is an oxadiazole ring which is substituted with R$^4$ and which is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, C$_{1-6}$alkoxy, C$_{1-6}$alkanoyl, C$_{1-6}$alkanoyloxy, C$_{1-6}$alkoxycarbonyl, C$_{3-8}$-carbocyclyl, and —N(R$^t$)$_2$.

In certain embodiments A is an isoxazole ring which is substituted with R$^4$ and which is also optionally substituted with one or more groups independently selected from halo, nitro, cyano, C$_{1-6}$alkyl, C$_{2-6}$alkenyl, C$_{2-6}$alkynyl, C$_{1-6}$haloalkyl, C$_{1-6}$alkoxy, C$_{1-6}$alkanoyl, C$_{1-6}$alkanoyloxy, C$_{1-6}$alkoxycarbonyl, C$_{3-8}$-carbocyclyl, and —N(R$^t$)$_2$.

In certain embodiments R$^4$ is H, C$_{1-6}$alkyl, C$_{2-6}$alkenyl, C$_{2-6}$alkynyl, carbocyclyl, heterocyclyl, —C(O)R$^g$, —CO$_2$R$^g$, or —C(O)N(R$^g$)$_2$, wherein each C$_{1-6}$alkyl, C$_{3-6}$alkenyl, C$_{3-6}$alkynyl, carbocyclyl, and heterocyclyl of R$^4$ is independently optionally substituted with one or more groups R$^x$.

In certain embodiments R$^4$ is heteroaryl that is optionally substituted with one or more groups independently selected from R$^x$.

In certain embodiments R$^4$ is heteroaryl that is optionally substituted with one or more groups independently selected from C$_{1-6}$alkyl, C$_{1-6}$haloalkyl, carbocyclyl, —F, —Cl, —Br, —I, —NO$_2$, —N(R$^v$)$_2$, —CN, —C(O)—N(R$^v$)$_2$, —O—C(O)—R$^v$, —C(O)—R$^v$, —C(O)—O—R$^v$, —C(O)—N(R$^v$)$_2$, and —N(R$^v$)—C(O)—R$^v$.

In certain embodiments R$^4$ is a pyrimidine, thiazole, pyridine, isoquinoline, or pyridazine ring, which ring is optionally substituted with one or more groups independently selected from C$_{1-6}$alkyl, carbocyclyl, —F, —Cl, —Br, —I, —N(R$^v$)$_2$, —O—R$^v$, and —C(O)—O—R$^v$.

In certain embodiments -A-R$^4$ taken together is selected from:

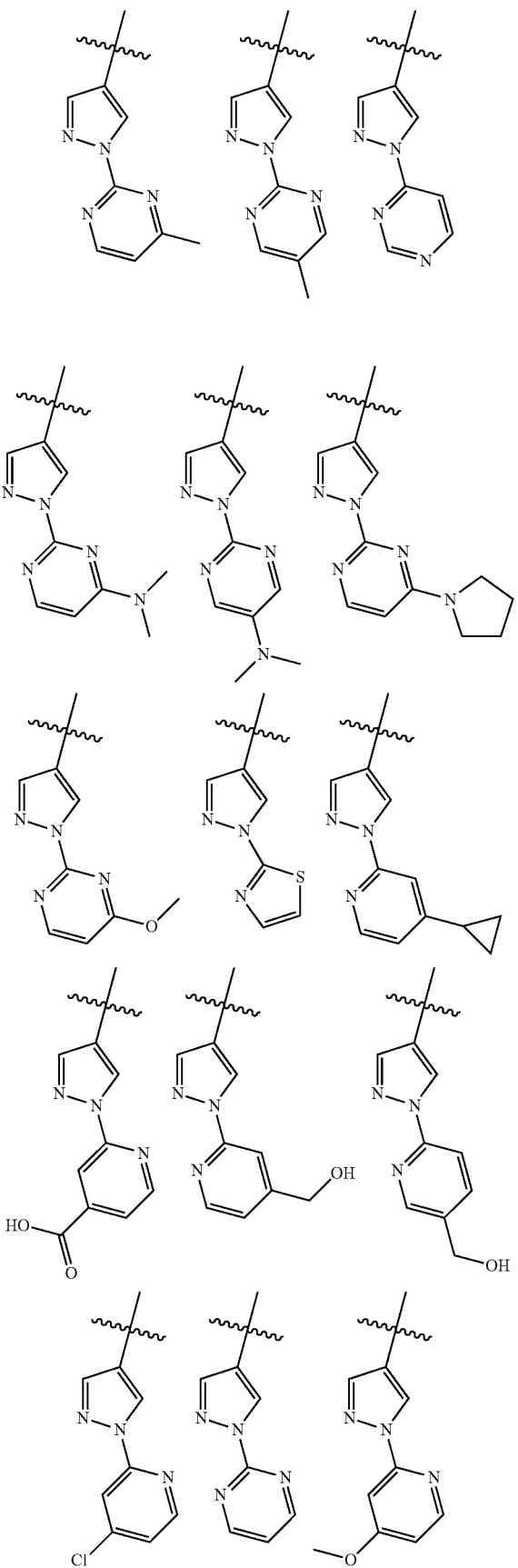

-continued
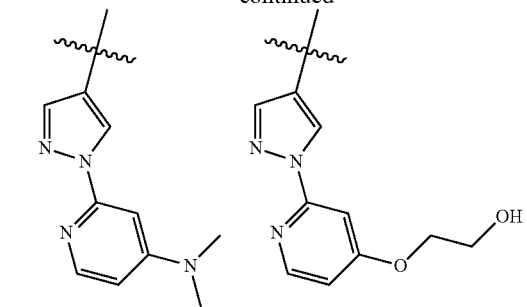
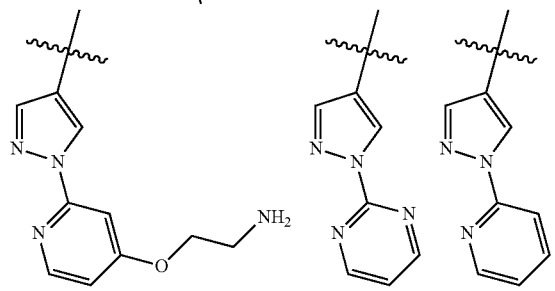
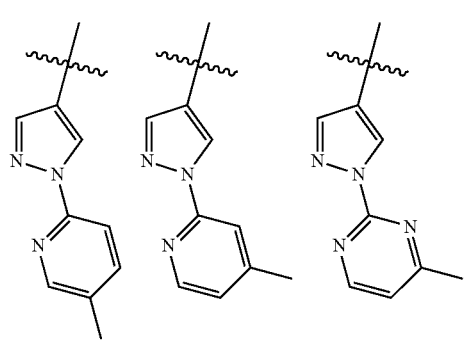
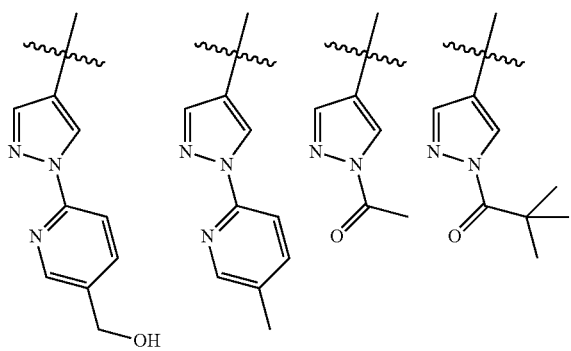
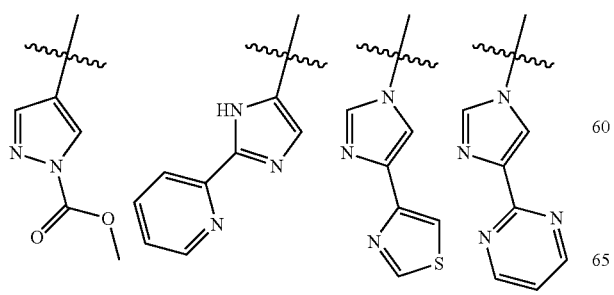
-continued
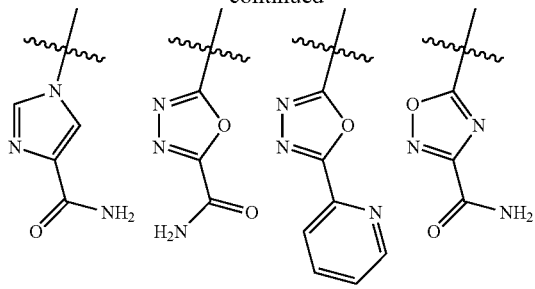
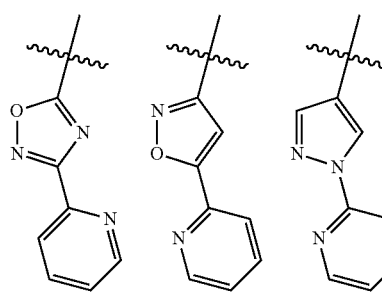
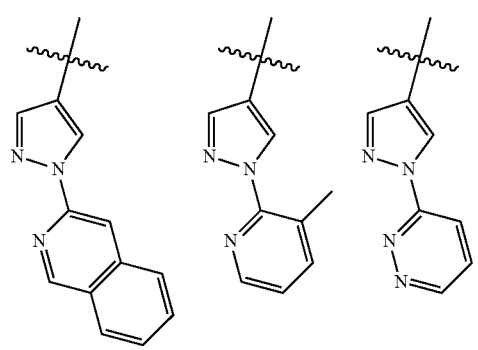
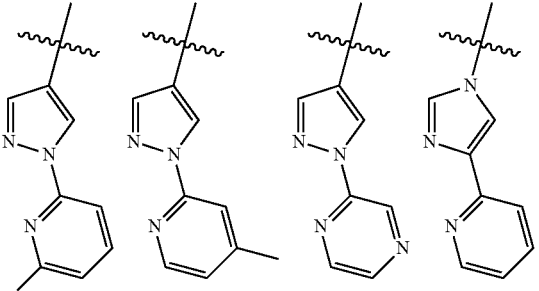
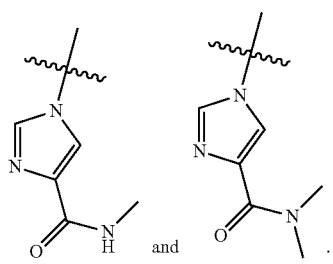
and Another aspect includes a compound selected from:
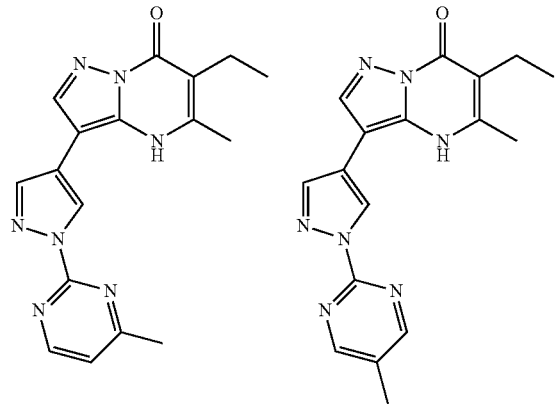
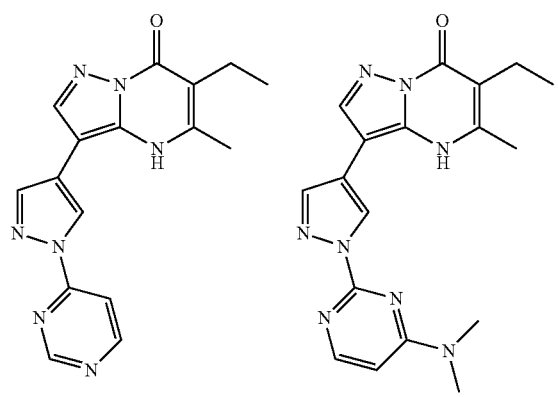
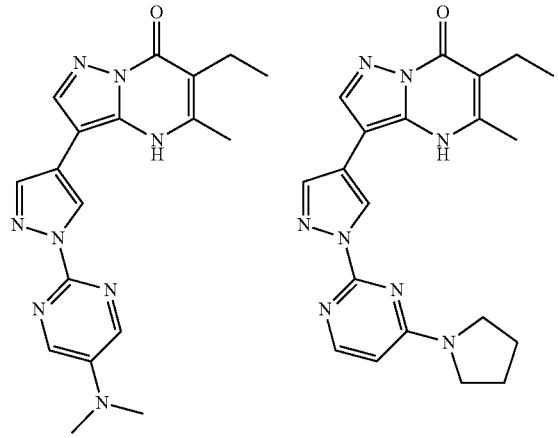
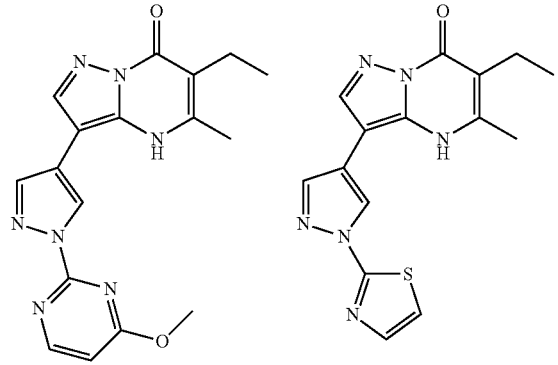
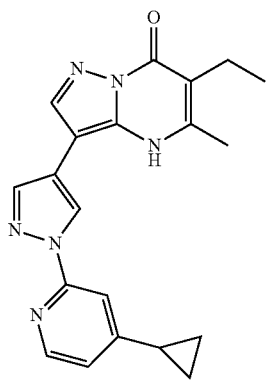
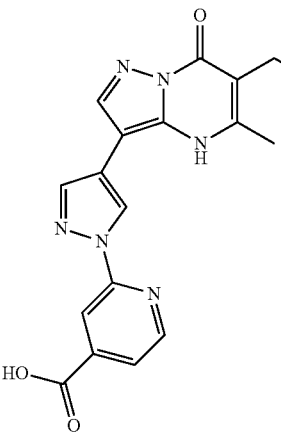
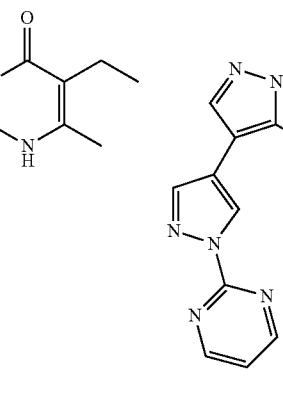

-continued
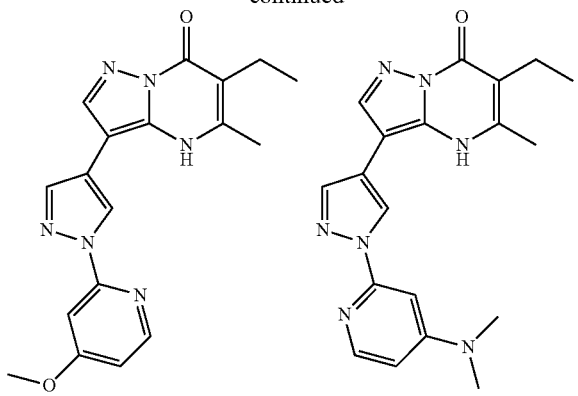
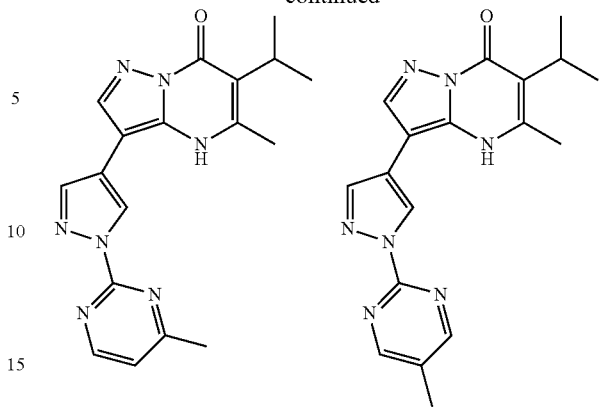
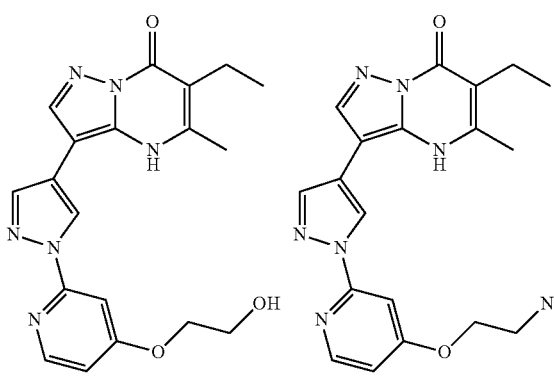
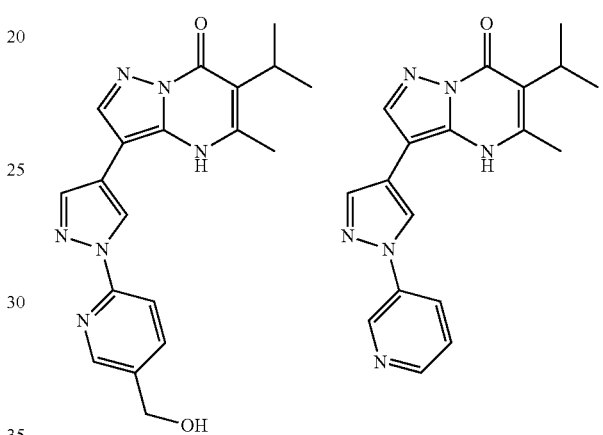
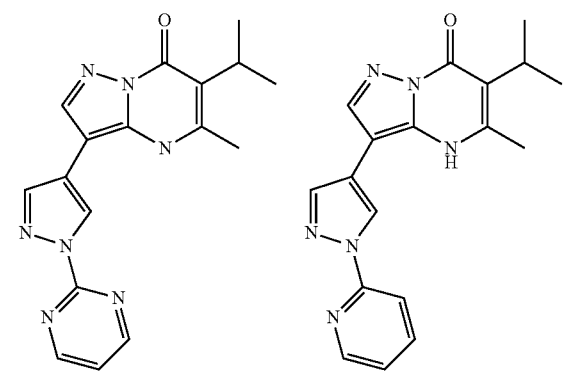
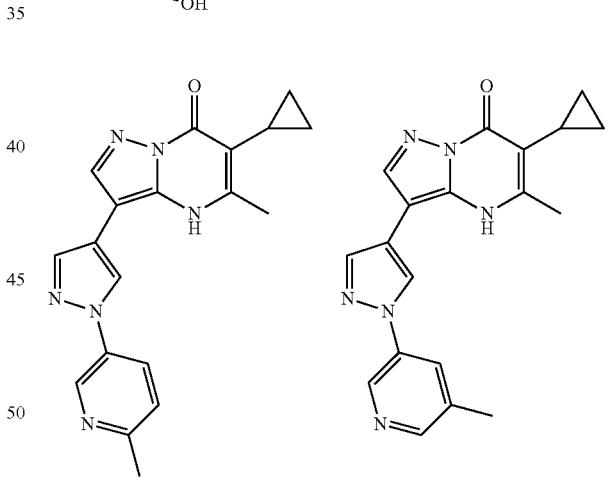
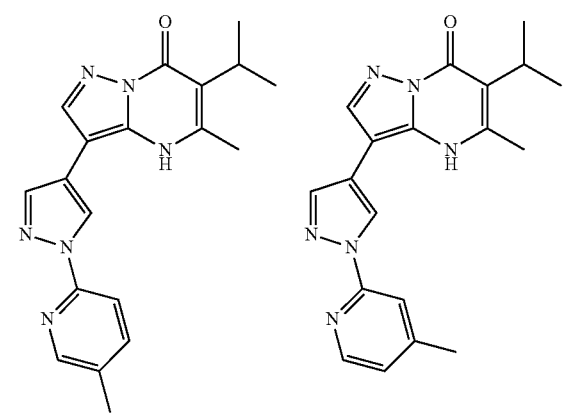
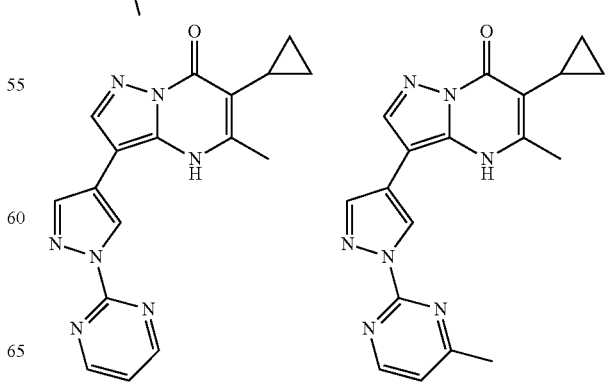

21
-continued
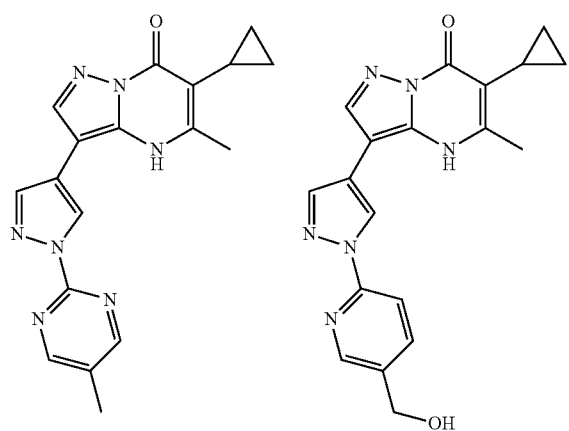
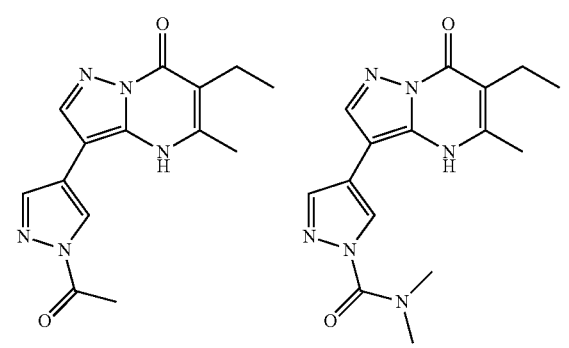
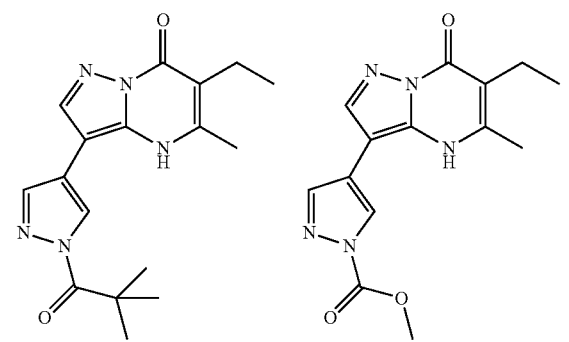
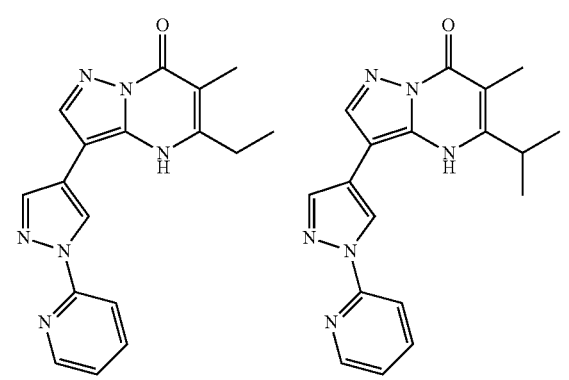
22
-continued
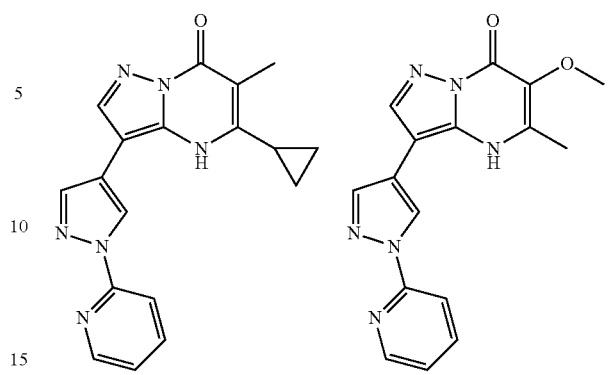
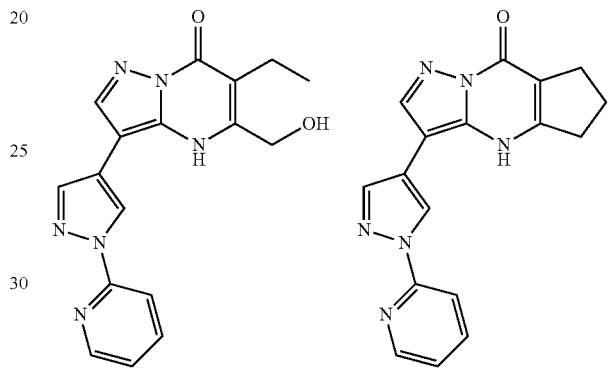
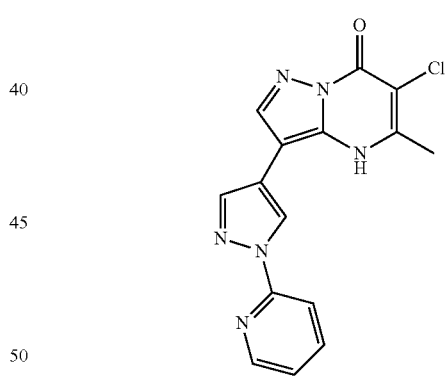
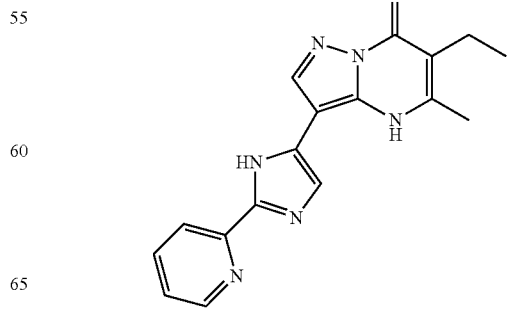

-continued
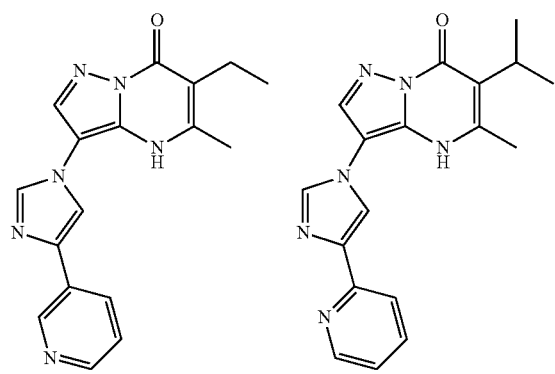
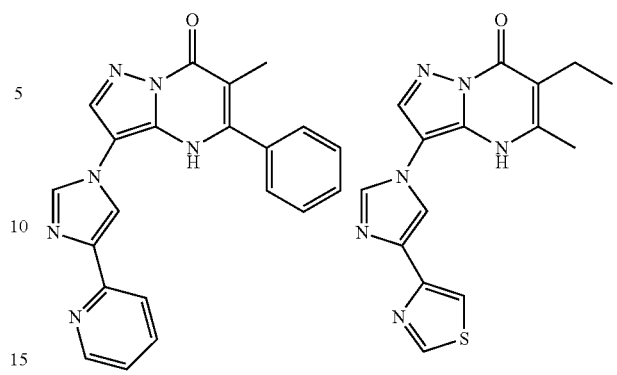
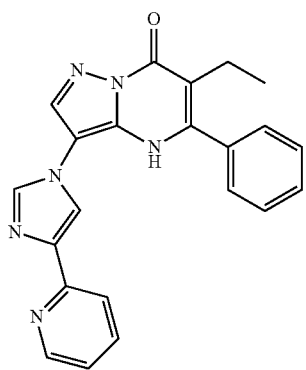
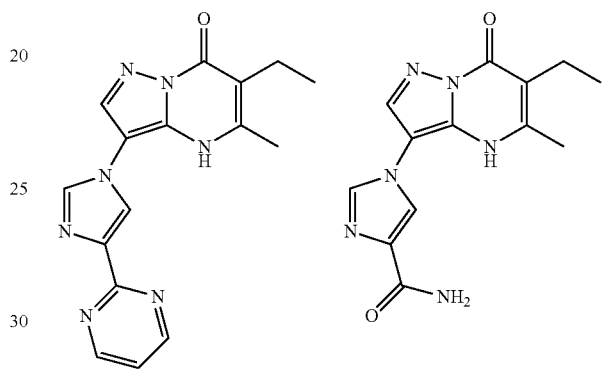
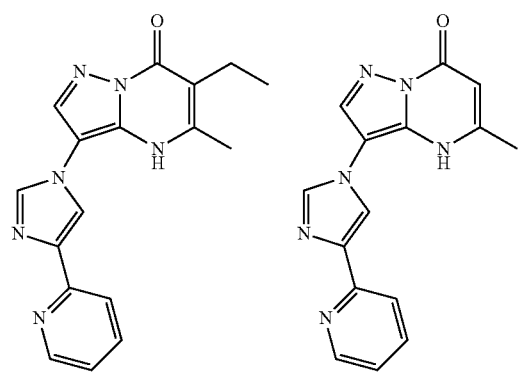
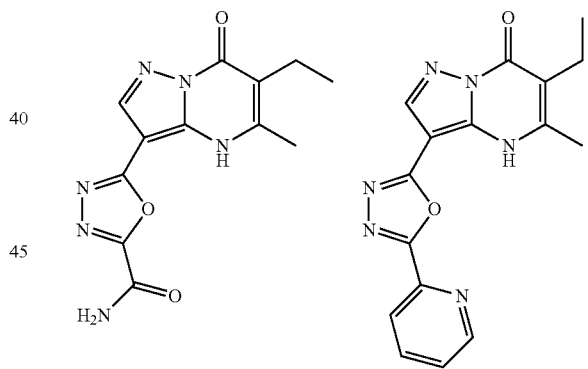
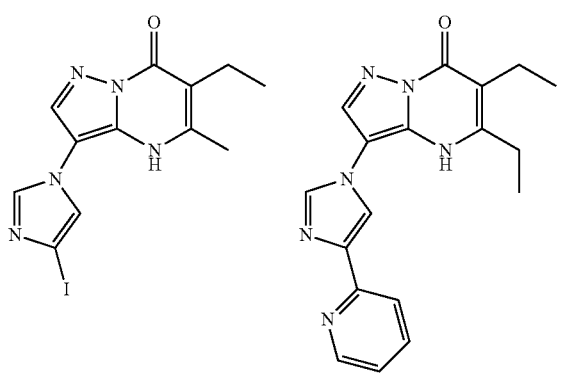
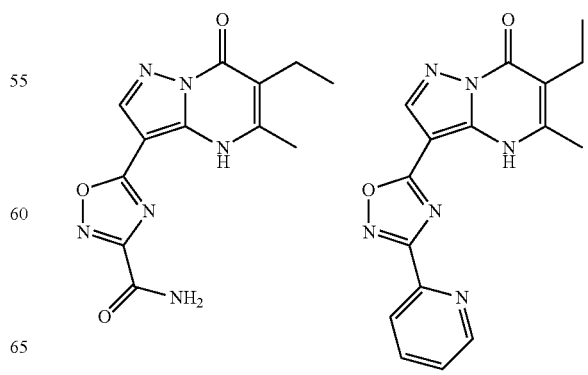

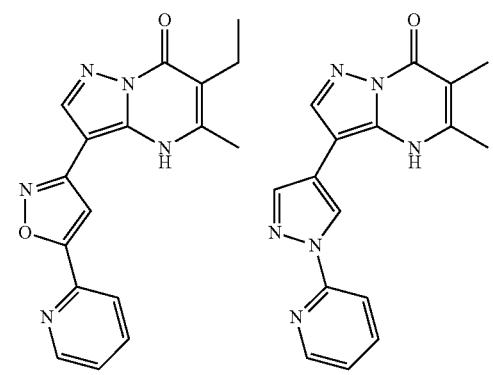
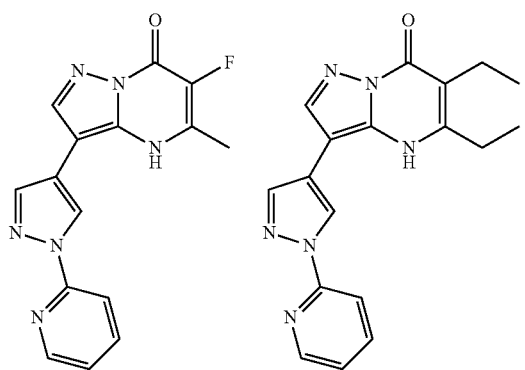
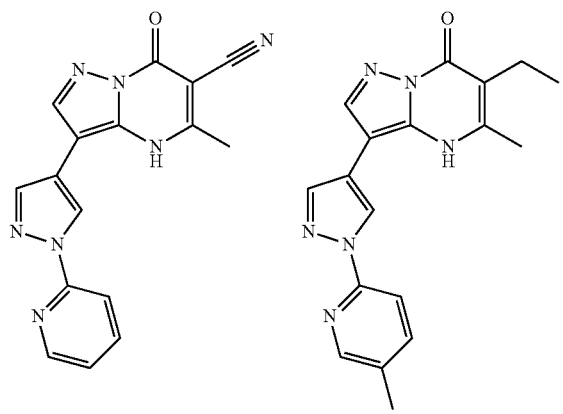
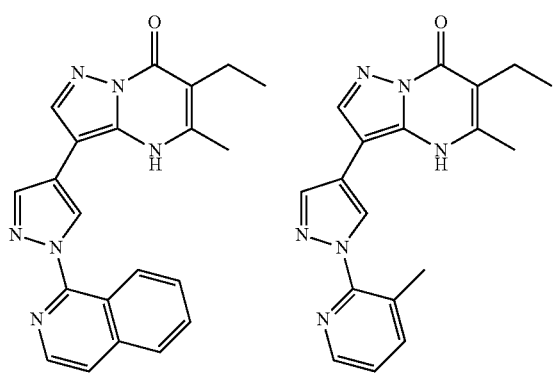
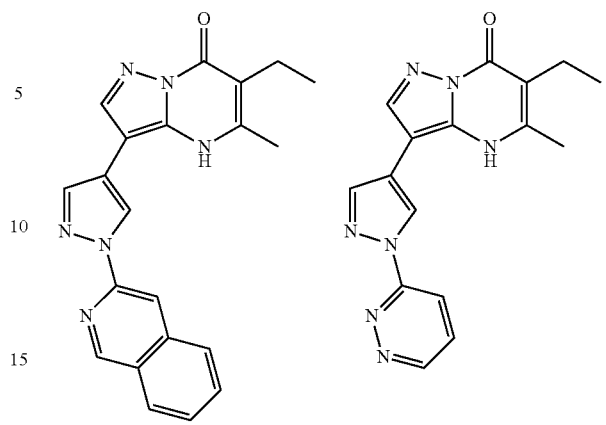
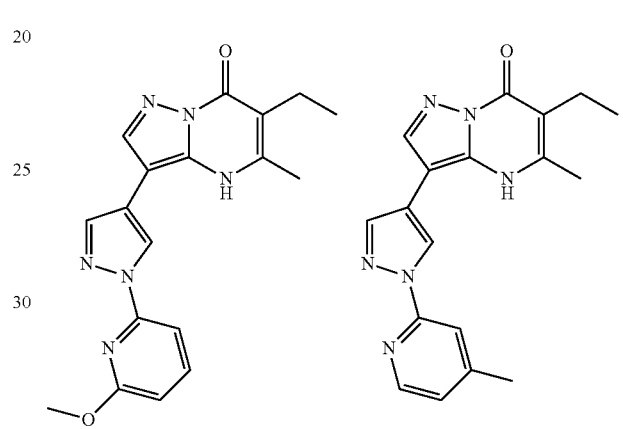
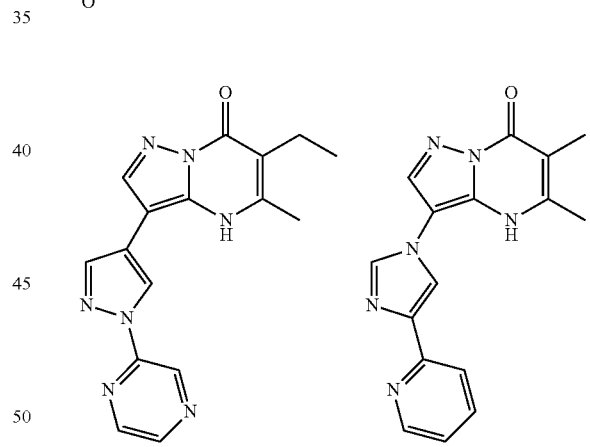
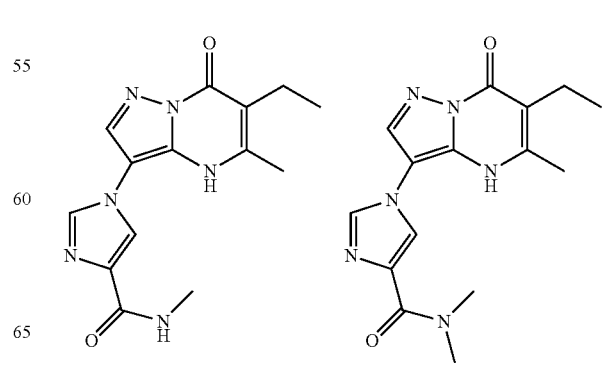

-continued

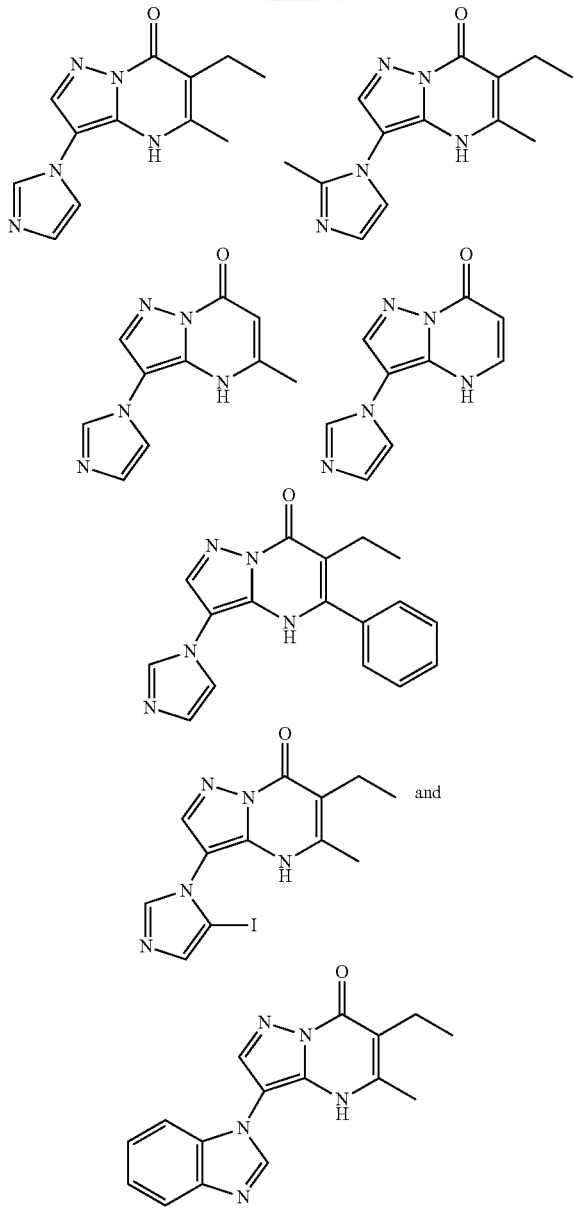

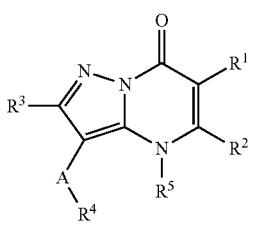

and salts thereof.

One embodiment provides the use of a compound of formula (I):

I or a salt thereof, wherein:

$R^1$ and $R^2$ are each independently H, $C_{1-12}$alkyl, $C_{2-12}$alkenyl, $C_{2-12}$alkynyl, carbocyclyl, heterocyclyl, halo, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —$C(=N)N(R^a)_2$, —$C=NOR^a$, —$C(=N(R^a))N(R^a)_2$, —$OC(O)R^a$, or —$OC(O)N(R^a)_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups $R^x$; and wherein $R^1$ and $R^2$ are not each H; or $R^1$ and $R^2$ taken together with the atoms to which they are attached form a 4, 5, 6, 7, or 8 membered carbocyclyl, which carbocyclyl is optionally substituted with one or more groups $R^x$;

$R^3$ is H, $C_{1-6}$alkyl, trifluoromethyl, 3-6 membered carbocyclyl, 3-6 membered heterocyclyl, halo, —$OR^f$, —$SR^f$, —$N(R^f)_2$, —CN, or —$NO_2$, wherein said alkyl, carbocyclyl and heterocyclyl are optionally substituted with one or more groups independently selected from oxo, halo, $C_{1-3}$alkoxy and $C_{1-3}$alkyl;

$R^4$ is H, $C_{1-12}$alkyl, $C_{2-12}$alkenyl, $C_{2-12}$alkynyl, carbocyclyl, heterocyclyl, halo, —$OR^g$, —$SR^g$, —$N(R^g)_2$, —CN, —$NO_2$, —$C(O)R^g$, —$CO_2R^g$, —$C(O)N(R^g)_2$, —$C(O)SR^g$, —$C(O)C(O)R^g$, —$C(O)CH_2C(O)R^g$, —$C(S)N(R^g)_2$, —$C(S)OR^g$, —$S(O)R^g$, —$SO_2R^g$, —$SO_2N(R^g)_2$, —$N(R^g)C(O)R^g$, —$N(R^g)C(O)N(R^g)_2$, —$N(R^g)SO_2R^g$, —$N(R^g)SO_2N(R^g)_2$, —$N(R^g)N(R^h)_2$, —$N(R^g)C(=N(R^g))N(R^g)_2$, —$C(=N)N(R^g)_2$, —$C=NOR^g$, —$C(=N(R^g))N(R^g)_2$, —$OC(O)R^g$, or —$OC(O)N(R^g)_2$, wherein each $C_{1-12}$alkyl, $C_{3-12}$alkenyl, $C_{3-12}$alkynyl, carbocyclyl, and heterocyclyl of $R^4$ is optionally substituted with one or more groups $R^x$;

$R^5$ is H, $C_{2-12}$alkenyl, $C_{2-12}$alkynyl, carbocyclyl, and heterocyclyl, wherein each $C_{1-12}$alkyl, $C_{2-12}$alkenyl, $C_{2-12}$alkynyl, carbocyclyl, and heterocyclyl is optionally substituted with one or more groups independently selected from oxo, $C_{1-12}$ alkyl, $C_{1-12}$haloalkyl, carbocyclyl, heterocyclyl, halo, —CN, —$NO_2$, —$NR^mR^m$, —$OR^m$, —$C(=O)OR^m$, and —$OC(=O)R^m$; or $R^5$ and $R^2$ taken together with the atoms to which they are attached form a heterocyclyl;

each $R^a$ is independently selected from H, $C_{1-6}$alkyl, $C_{2-6}$alkenyl, $C_{2-6}$alkynyl, carbocyclyl, and heterocyclyl, wherein each $C_{1-6}$alkyl, $C_{3-6}$alkenyl, $C_{3-6}$alkynyl, carbocyclyl, and heterocyclyl is optionally substituted with one or more groups $R^x$;

each $R^f$ is independently selected from H, $C_{1-3}$ alkyl, trifluoromethyl, 3-6 membered carbocyclyl, and 3-6 membered heterocyclyl; or two $R^f$ groups together with the nitrogen to which they are attached form a 3-6 membered heterocycle;

each $R^g$ is independently selected from H, $C_{1-6}$alkyl, $C_{2-6}$alkenyl, $C_{2-6}$alkynyl, $C_{3-8}$carbocyclyl, and heterocyclyl, wherein each $C_{1-6}$alkyl, $C_{3-6}$alkenyl, $C_{3-6}$alkynyl, $C_{3-8}$carbocyclyl, and heterocyclyl is optionally substituted with one or more groups $R^x$; or two $R^g$ groups together with the nitrogen to which they are attached form a 3-6 membered heterocycle;

each $R^m$ is independently selected from H, $C_{1-6}$alkyl, $C_{2-6}$alkenyl, $C_{2-6}$alkynyl, $C_{1-6}$haloalkyl, carbocyclyl, $C_{1-6}$ alkanoyl, phenyl, and benzyl, wherein any $C_{1-6}$alkyl, $C_{2-6}$alkenyl, $C_{2-6}$alkynyl, $C_{1-6}$ haloalkyl, carbocyclyl, $C_{1-6}$ alkanoyl, phenyl, or benzyl is optionally substituted with one or more groups independently selected from halo, —CN, —$NO_2$, —$NR^yR^z$, and —$OR^w$; or two $R^m$ groups together with the nitrogen to which they are attached form a 3-6 membered heterocycle;

A is a monocyclic or bicyclic heteroaryl ring that is substituted with $R^4$ and that is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, —$OR^t$, —$C(O)R^t$, —$CO_2R^t$, —$OC(O)R^t$, —$N(R^t)_2$, and carbocyclyl;

each $R^t$ is independently selected from H, $C_{1-6}$alkyl, $C_{2-6}$alkenyl, $C_{2-6}$alkynyl, $C_{3-8}$carbocyclyl, and heterocyclyl, wherein each $C_{1-6}$alkyl, $C_{3-6}$alkenyl, $C_{3-6}$alkynyl, $C_{3-8}$carbocyclyl, and heterocyclyl is optionally substituted with one or more groups $R^x$; or two $R^t$ groups together with the nitrogen to which they are attached form a 3-6 membered heterocycle;

each $R^v$ is independently hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, halo, amino, hydroxyl, and $C_1$-$C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^w$ is independently selected from H, $C_{1-4}$alkanoyl, phenyl, benzyl, and phenethyl;

each $R^x$ is independently selected from oxo, $C_{1-6}$alkyl, $C_{2-6}$alkenyl, $C_{2-6}$alkynyl, $C_{1-6}$haloalkyl, carbocyclyl, —F, —Cl, —Br, —I, —$NO_2$, —$N(R^v)_2$, —CN, —C(O)—N$(R^v)_2$, —S(O)—N$(R^v)_2$, —S(O)$_2$—N$(R^v)_2$, —O—$R^v$, —S—$R^v$, —O—C(O)—$R^v$, —O—C(O)—O—$R^v$, —C(O)—$R^v$, —C(O)—O—$R^v$, —S(O)—$R^v$, —S(O)$_2$—$R^v$, —O—C(O)—N$(R^v)_2$, —N$(R^v)$—C(O)—O$R^v$, —N$(R^v)$—C(O)—N$(R^v)_2$, —S(O)$_2$—N$(R^v)_2$, —N$(R^v)$—C(O)—$R^v$, —N$(R^v)$—S(O)—$R^v$, —N$(R^v)$—S(O)$_2$—$R^v$, —N$(R^v)$—S(O)—N$(R^v)_2$, and —N$(R^v)$—S(O)$_2$—N$(R^v)_2$, wherein any $C_{1-6}$alkyl, $C_{2-6}$alkenyl, $C_{2-6}$alkynyl, $C_{1-6}$haloalkyl and carbocyclyl is optionally substituted with one or more groups independently selected from oxo, halo, —$NO_2$, —$N(R^v)_2$, —CN, —C(O)—N$(R^v)_2$, —S(O)—N$(R^v)_2$, —S(O)$_2$—N$(R^v)_2$, —O—$R^v$, —S—$R^v$, —O—C(O)—$R^v$, —C(O)—$R^v$, —C(O)—O—$R^v$, —S(O)—$R^v$, —S(O)$_2$—$R^v$, —C(O)—N$(R^v)_2$, —S(O)$_2$—N$(R^v)_2$, —N$(R^v)$—C(O)—$R^v$, —N$(R^v)$—S(O)—$R^v$—N$(R^v)$—S(O)$_2$—$R^v$ and $C_{1-6}$alkyl that is optionally substituted with one or more groups independently selected from oxo and halo; and each $R^y$ and $R^z$ is independently selected from H, $C_{1-4}$alkyl, $C_{1-4}$alkanoyl, $C_{1-4}$alkoxycarbonyl, phenyl, benzyl, and phenethyl, or $R^y$ and $R^z$ together with the nitrogen to which they are attached form a heterocyclyl;

for the prophylactic or therapeutic treatment of a proliferative disorder.

In certain embodiments $R^1$ is H, $C_{1-12}$alkyl, $C_{2-12}$alkenyl, $C_{2-12}$alkynyl, carbocyclyl, heterocyclyl, halo, —$OR^a$, —$SR^a$, —$N(R^a)$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —C=$NOR^a$, —C(=N($R^a$))N$(R^a)_2$, —$OC(O)R^a$, or —$OC(O)N(R^a)_2$, wherein each $C_{2-12}$alkenyl, $C_{2-12}$alkynyl, carbocyclyl, and heterocyclyl of $R^1$ and $R^2$ is independently optionally substituted with one or more groups $R^x$.

In certain embodiments $R^1$ is $C_{1-12}$alkyl, $C_{2-12}$alkenyl, $C_{2-12}$alkynyl, carbocyclyl, heterocyclyl, halo, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —C=$NOR^a$, —C(=N($R^a$))N$(R^a)_2$, —$OC(O)R^a$, or —$OC(O)N(R^a)_2$, wherein each $C_{2-12}$alkenyl, $C_{2-12}$alkynyl, carbocyclyl, and heterocyclyl of $R^1$ and $R^2$ is independently optionally substituted with one or more groups $R^x$.

In certain embodiments $R^2$ is H, $C_{2-12}$alkenyl, $C_{2-12}$alkynyl, carbocyclyl, heterocyclyl, halo, —$OR^a$, —$SR^a$, —$N(R^a)$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —C=$NOR^a$, —C(=N($R^a$))N$(R^a)_2$, —$OC(O)R^a$, or —$OC(O)N(R^a)_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups $R^x$.

In certain embodiments $R^2$ is $C_{1-12}$alkyl, $C_{2-12}$alkenyl, $C_{2-12}$alkynyl, carbocyclyl, heterocyclyl, halo, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —C=$NOR^a$, —C(=N($R^a$))N$(R^a)_2$, —$OC(O)R^a$, or —$OC(O)N(R^a)_2$, wherein each $C_{2-12}$alkenyl, $C_{2-12}$alkynyl, carbocyclyl, and heterocyclyl of $R^1$ and $R^2$ is independently optionally substituted with one or more groups $R^x$.

In certain embodiments $R^4$ is H, $C_{1-6}$alkyl, $C_{2-6}$alkenyl, $C_{2-6}$alkynyl, carbocyclyl, heterocyclyl, —$C(O)R^g$, —$CO_2R^g$, or —$C(O)N(R^g)_2$, wherein each $C_{1-6}$alkyl, $C_{2-6}$alkenyl, $C_{2-6}$alkynyl, carbocyclyl, and heterocyclyl of $R^4$ is optionally substituted with one or more groups $R^x$.

Uses, Formulation and Administration

Pharmaceutically Acceptable Compositions

Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit KDM5. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 95-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof for the inhibition of KDM5. Compounds of formula (I) may also be used to inhibit the removal of methyl marks on histone lysine residues, including inhibiting the removal of methyl marks from mono-, di- or tri-methylation of histones H1, H2A, H2B, H3 and H4, such as H3K4 (including for example the KDM5 substrate H3K4me3), thereby altering interactions of these histone proteins with DNA and/or other proteins, and altering certain subsequent genetic or protein expression. Compounds of formula (I) may also be used to inhibit KDM5 and reduce drug-tolerant cells, thereby treating or preventing drug-resistant diseases, such as drug-resistant cancer. In certain embodiments, the disease can be treated using compounds of formula (I) to prevent resistance from forming, for example before targets of chemotherapies become mutated to confer resistance to such chemotherapies.

In certain embodiments, the binding or inhibition activity of a compound of formula (I) may be determined by running a competition experiment where a compound of formula (I) is incubated with the KDM5 enzyme bound to known radioligands. Detailed conditions for assaying a compound of formula (I) as an inhibitor of KDM5 or a mutant thereof are set forth in the Examples below.

In certain embodiments, detection of KDM5 activity is achieved with in vitro assays, which can be either direct binding (non-catalytic) or enzymatic (catalytic) assays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes.

Another aspect includes a method of treating or preventing a disease responsive to the inhibition of KDM5 activity in a patient. The method includes administering a therapeutically effective amount of a compound of formula (I) or a salt thereof to a patient in need thereof.

Another aspect includes the use of a compound of formula (I), or a pharmaceutically acceptable salt thereof, in therapy. Another aspect includes the use of a pharmaceutical composition comprising a compound of formula (I), or a pharmaceutically acceptable salt thereof, in therapy.

Another aspect includes the use of a compound of formula (I), or a pharmaceutically acceptable salt thereof, in treating a disease associated with KDM5 activity. Another aspect includes the use of a pharmaceutical composition comprising a compound of formula (I), or a pharmaceutically acceptable salt thereof, in treating a disease associated with KDM5 activity.

Another aspect includes the use of a compound of formula (I), or a pharmaceutically acceptable salt thereof, in the manufacture of a medicament for the treatment of a disease associated with KDM5 activity. Another aspect includes the use of a pharmaceutical composition comprising a compound of formula (I), or a pharmaceutically acceptable salt thereof, in the manufacture of a medicament for the treatment of a disease associated with KDM5 activity.

In certain embodiments, the disease or condition is a hyperproliferative disease, cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Another aspect includes a method for treating, ameliorating or preventing cancer, drug-resistant cancer or another proliferative disorder by administration of an effective amount of a compound of formula (I) or salt thereof to a mammal, for example a human, in need of such treatment. In certain embodiments, the disease to be treated is cancer or drug resistant cancer.

Examples of cancers that may be treated using the compounds and methods described herein include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, androgen dependent cancer, angioimmunoblastic T-cell lymphoma, angiomyolipoma, angiosarcoma, astrocytoma, atypical teratoid rhabdoid tumor, B-cell chronic lymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor and Wilms' tumor.

Another embodiment includes a method for the treatment of benign proliferative disorders. Examples of benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma and juvenile polyposis syndrome.

Another embodiment includes a therapeutic method useful for modulating protein methylation, gene expression, cell proliferation, cell differentiation and/or apoptosis in vivo in diseases mentioned above, in particular cancer, comprising administering to a patient in need of such therapy a pharmacologically active and therapeutically effective amount of one or more of the compounds of formula (I).

Another embodiment includes a method for regulating endogenous or heterologous promoter activity by contacting a cell with a compound of formula (I).

Another embodiment includes the use of a compound of formula I or salt thereof for the production of pharmaceutical compositions which are employed for the treatment and/or prophylaxis and/or amelioration of the diseases, disorders, illnesses and/or conditions as mentioned herein.

Another embodiment includes the use of a compound of formula I or salt thereof for the production of pharmaceutical compositions which are employed for the treatment and/or prophylaxis of diseases and/or disorders responsive or sensitive to the inhibition of histone demethylases, particularly those diseases mentioned above, such as e.g. cancer.

Compounds of formula (I) or salts thereof may be administered using any amount and any route of administration effective for treating or lessening the severity of the disorder. The exact amount required will vary from patient to patient, depending on the species, age, and general condition of the patient, for example the severity of the disorder, the particular compound, its mode of administration, and the like.

The total daily usage of a compound of formula (I) by a given patient will be decided by the attending physician within the scope of sound medical judgment. The specific effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Another embodiment includes a method of inhibiting KDM5 activity in a biological sample comprising contacting said biological sample with a compound of formula I or salt thereof.

The term "biological sample", as used herein, includes, without limitation, a cell, cell cultures or extracts thereof; biopsied material obtained from a mammal or extracts thereof; and blood, saliva, urine, feces, semen, tears, or other body fluids or extracts thereof.

Co-Administration of Compounds and Other Agents

The compounds of formula (I) or salts thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{132}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfuram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chiomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2-methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

The amount of both the compound of formula (I) or salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Another aspect includes treating or preventing drug resistance in a patient using a compound of formula (I) or a pharmaceutically acceptable salt thereof. For example, a method of treating or preventing drug resistant cancer in a patient comprises administering a therapeutically effective amount of a compound of formula (I) to the patient alone or in combination with a cytotoxic agent. In certain embodiments, the individual is selected for treatment with a cytotoxic agent (e.g., targeted therapies, chemotherapies, and/or radiotherapies). In certain embodiments, the individual starts treatment comprising administration of a compound of formula (I) or a pharmaceutically acceptable salt thereof prior to treatment with the cytotoxic agent. In certain embodiments, the individual concurrently receives treatment comprising the compound of formula (I) or a pharmaceutically acceptable salt thereof and the cytotoxic agent. In certain embodiments, the compound of formula (I) or the pharmaceutically acceptable salt thereof increases the period of cancer sensitivity and/or delays development of cancer resistance.

In particular, provided herein are methods of treating cancer in an individual comprising administering to the individual (a) a compound of formula (I) or a pharmaceutically acceptable salt thereof and (b) a cytotoxic agent (e.g., targeted therapy, chemotherapy, and/or radiotherapy). In certain embodiments, the respective amounts of the compound of formula (I) or a pharmaceutically acceptable salt thereof and the cytotoxic agent are effective to increase the period of cancer sensitivity and/or delay the development of cancer cell resistance to the cancer therapy agent. In certain embodiments, the respective amounts of the compound of formula (I) or a pharmaceutically acceptable salt thereof and the cytotoxic agent are effective to increase efficacy of a cancer treatment comprising the cancer therapy agent. For example, in certain embodiments, the respective amounts of the compound of formula (I) or a pharmaceutically acceptable salt thereof and the cytotoxic agent are effective to increase efficacy compared to a treatment (e.g., standard of care treatment) (e.g., standard of care treatment) comprising administering an effective amount of the cancer therapy agent without (in the absence of) the compound of formula (I) or a pharmaceutically acceptable salt thereof. In certain embodiments, the respective amounts of the compound of formula (I) or a pharmaceutically acceptable salt thereof and cytotoxic agent are effective to increase response (e.g., complete response) compared to a treatment (e.g., standard of care treatment) comprising administering an effective amount of cytotoxic agent without (in the absence of) the compound of formula (I) or a pharmaceutically acceptable salt thereof.

Also provided herein are methods of increasing efficacy of a cancer treatment comprising a cytotoxic agent in an individual comprising administering to the individual (a) an effective amount of a compound of formula (I) or a pharmaceutically acceptable salt thereof and (b) an effective amount of the cytotoxic agent.

Provided herein are methods of treating cancer in an individual wherein cancer treatment comprising administering to the individual (a) an effective amount of a compound of formula (I) or a pharmaceutically acceptable salt thereof and (b) an effective amount of a cytotoxic agent, wherein the cancer treatment has increased efficacy compared to a treatment (e.g., standard of care treatment) comprising administering an effective amount of cytotoxic agent without (in the absence of) the compound of formula (I) or a pharmaceutically acceptable salt thereof.

In addition, provided herein are methods of delaying and/or preventing development of cancer resistant to a cancer therapy agent in an individual, comprising administering to the individual (a) an effective amount of a compound of formula (I) or a pharmaceutically acceptable salt thereof and (b) an effective amount of the cytotoxic agent.

Provided herein are methods of treating an individual with cancer who has an increased likelihood of developing resistance to a cancer therapy agent comprising administering to the individual (a) an effective amount of a compound of formula (I) or a pharmaceutically acceptable salt thereof and (b) an effective amount of the cytotoxic agent.

Further provided herein are methods of increasing sensitivity to a cancer therapy agent in an individual with cancer comprising administering to the individual (a) an effective amount of a compound of formula (I) or a pharmaceutically acceptable salt thereof and (b) an effective amount of the cytotoxic agent.

Provided herein are also methods of extending the period of a cancer therapy agent sensitivity in an individual with cancer comprising administering to the individual (a) an effective amount of a compound of formula (I) or a pharmaceutically acceptable salt thereof and (b) an effective amount of the cytotoxic agent.

Provided herein are methods of extending the duration of response to a cytotoxic agent in an individual with cancer comprising administering to the individual (a) an effective amount of a compound of formula (I) or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di-4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

In certain embodiments of any of the methods, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

EXEMPLIFICATION

As depicted in the Examples below, in certain exemplary embodiments, compounds are prepared according to the following general procedures, wherein $R^1$, $R^2$, $R^3$, and $R^4$ are as defined for formula I and its alternative embodiments; X is halogen; A, B and D are independently selected from carbon and heteroatom, in one example carbon or nitrogen; R is $C_{1-6}$ alkyl; and M is —C(O)H, —CN, —C(O)OH or —C(O)O($C_{1-6}$ alkyl). It will be appreciated that, although the general methods depict the synthesis of certain compounds of the present invention, the following general methods, and other methods known to one of ordinary skill in the art, can be applied to all compounds and subclasses and species of each of these compounds, as described herein.

Scheme 1 (method A)
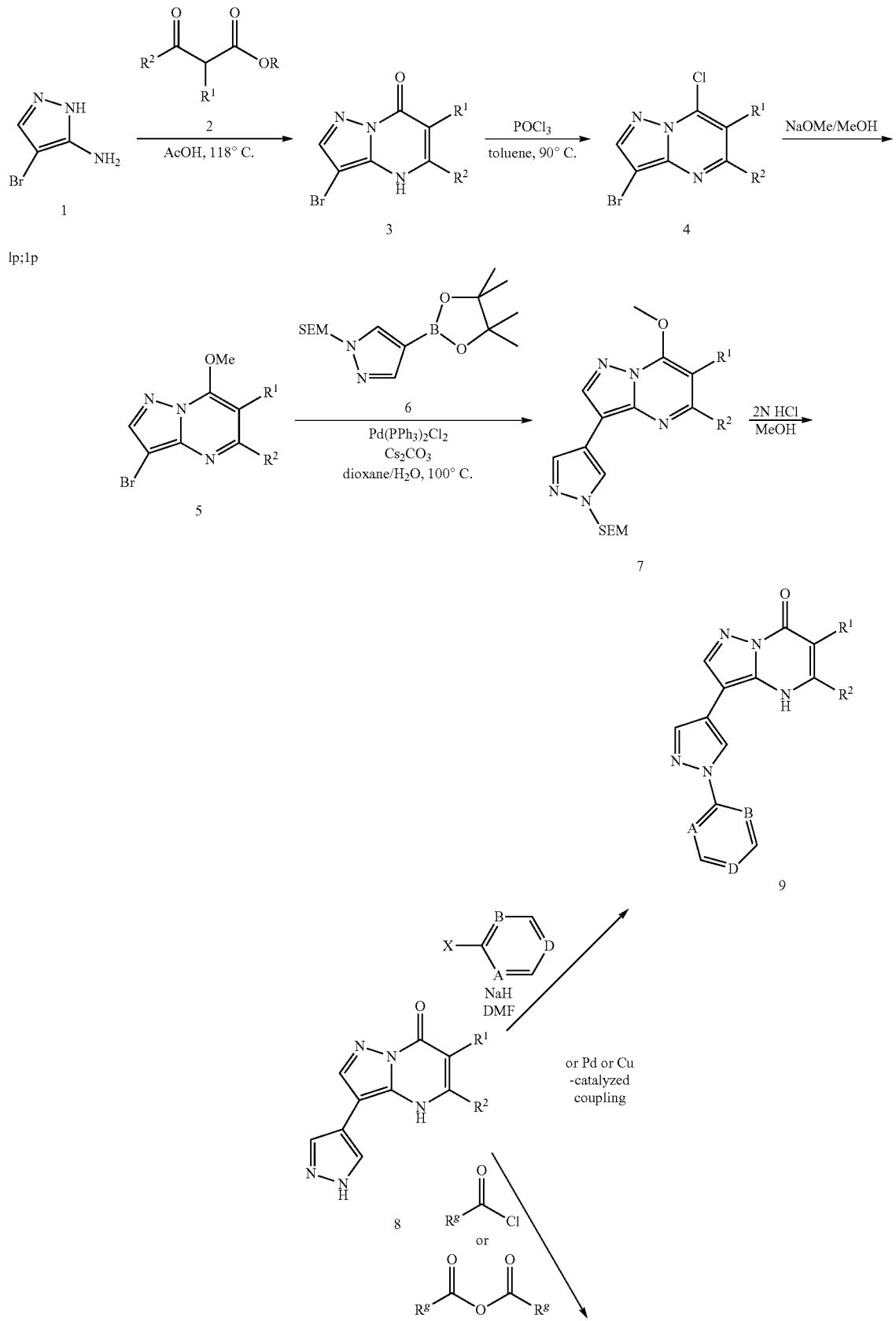

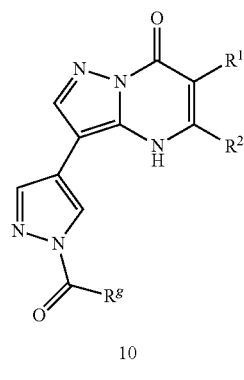

10

The general synthesis of targets 9 and 10 are illustrated in Scheme 1. 4-bromo-1H-pyrazol-5-amine (1) is condensed with β-ketoester 2 in refluxing acetic acid to give intermediate 3. This is followed by reaction with phosphorus oxychloride that leads to intermediate 4, which when treated with sodium methoxide in methanol forms bromide 5. Suzuki coupling of bromide 5 with a SEM-protected-pyrazole boronate ester (6) provides intermediate 7. After deprotection of SEM-group, the resulting pyrazole 8 is further coupled with a heteroaryl halide to give target 9. Intermediate 8 can also react with an acid chloride or anhydride to give target 10.

Scheme 3 (alternative synthesis of 9, method B)

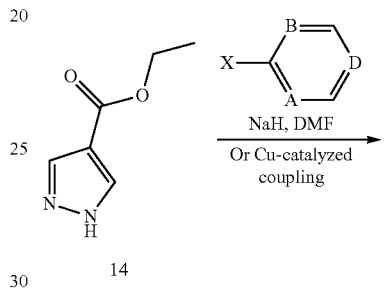

14

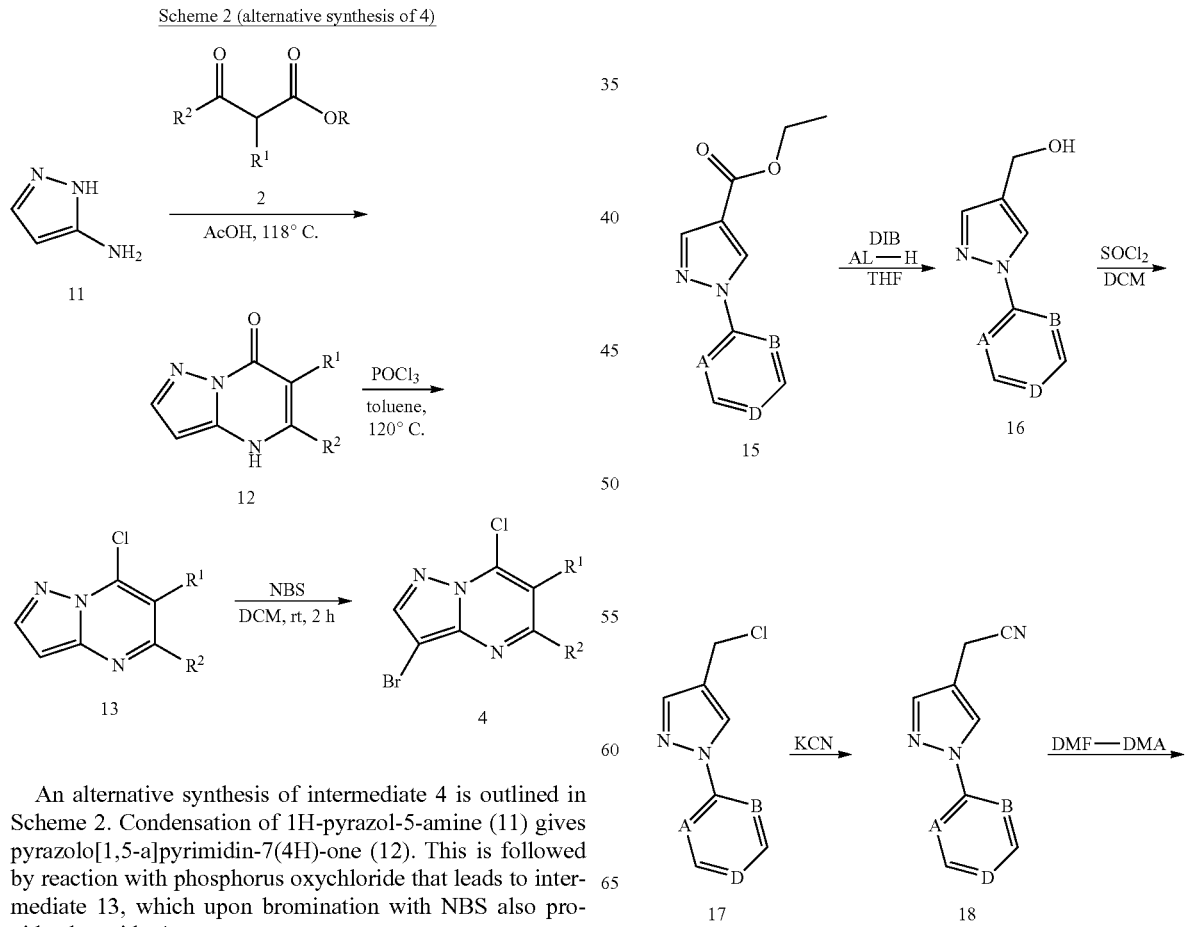

An alternative synthesis of intermediate 4 is outlined in Scheme 2. Condensation of 1H-pyrazol-5-amine (11) gives pyrazolo[1,5-a]pyrimidin-7(4H)-one (12). This is followed by reaction with phosphorus oxychloride that leads to intermediate 13, which upon bromination with NBS also provides bromide 4.

Scheme 4 (Method C)

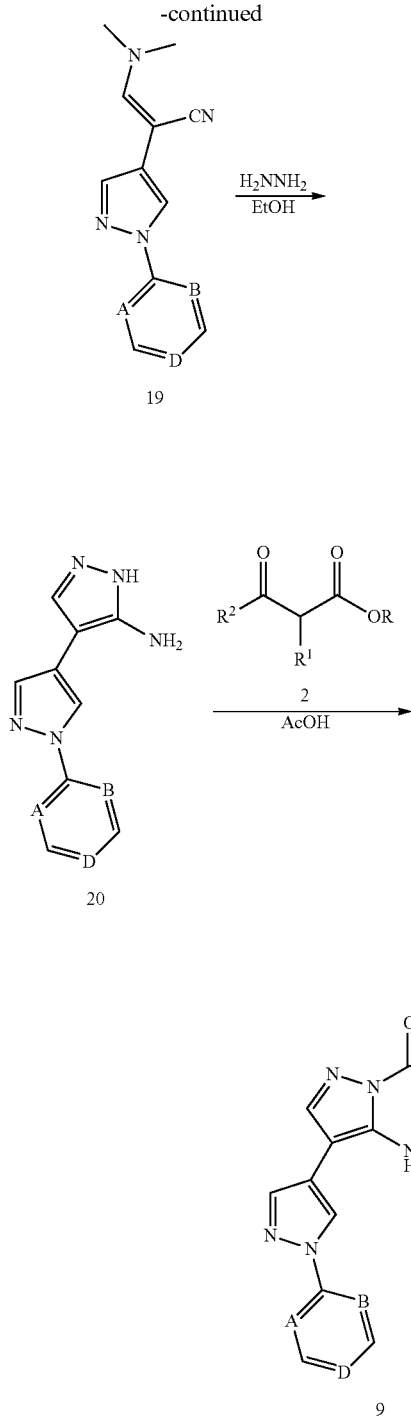
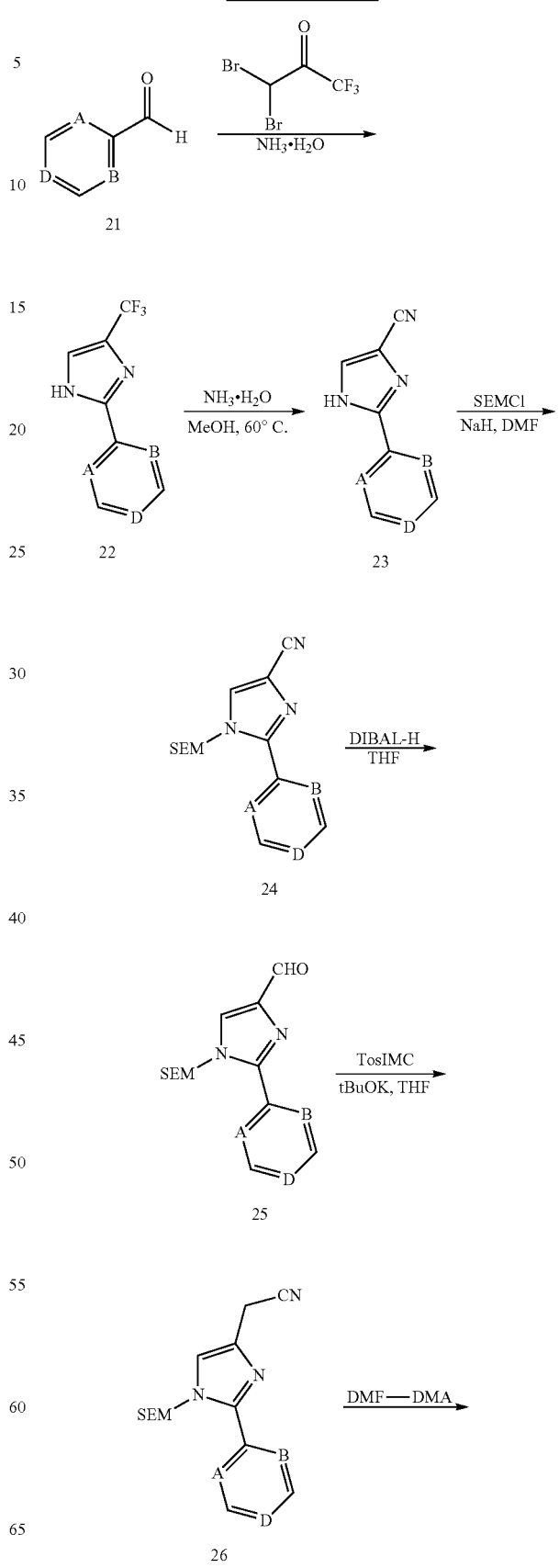

An alternative synthesis (method B) of target 9 is outlined in Scheme 3. 1H-pyrazole-4-carboxylate is coupled to an heteroaryl halide either under basic, or Cu-catalyzed, conditions. Then ethyl ester 15 is reduced with DIBAL-H to give primary alcohol 16, which is transformed to chloride 16 with thionyl chloride. Displacement of chloride with potassium cyanide gives 18. When treated with N,N-dimethylformamide dimethylacetal (DMF-DMA), intermediate 19 is formed. Reaction with hydrazine gives amino-pyrazole 20, which can be transformed to target 9 upon condensation with β-ketoester 2.

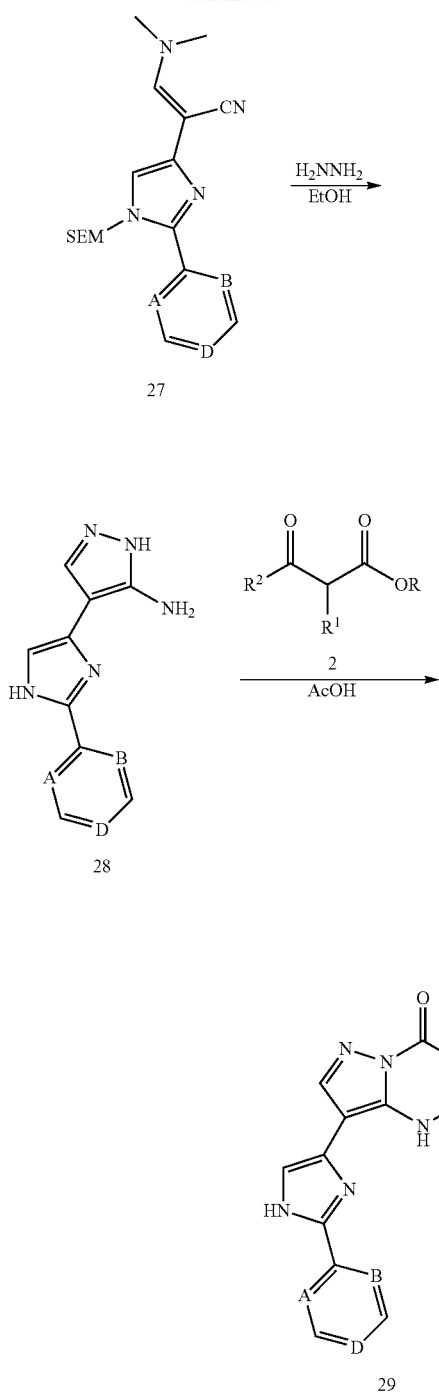

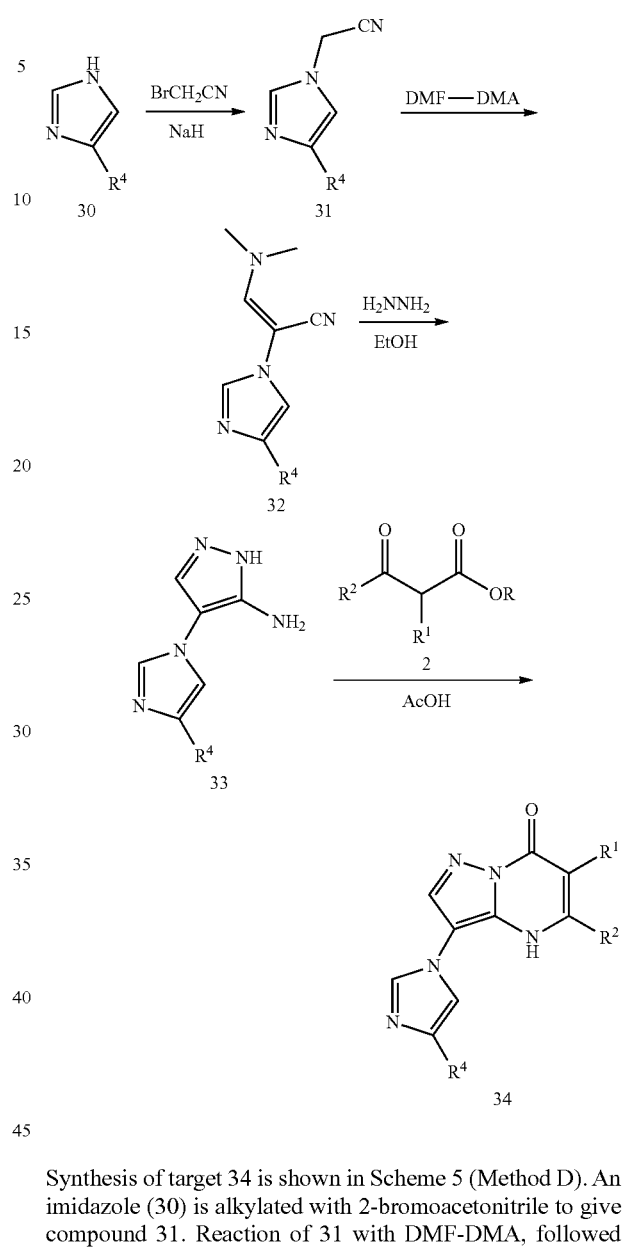

Synthesis of target 29 is shown in Scheme 4 (method C). An aldehyde (21) is condensed with 3,3-dibromo-1,1,1-trifluoropropan-2-one to give imidazole 22, which upon treatment with ammonium hydroxide leads to compound nitrile 23. Protection with SEM group, followed by reduction of nitrile with DIBAL-H provides aldehyde 25. When the aldehyde is treated with TosMIC in the presence of potassium tert-butoxide, nitrile 26 is formed. Reaction of 26 with DMF-DMA, followed condensation with hydrazine, results in amino-pyrazole 28. Subsequent reaction of compound 28 with β-ketoester 2 then provides target 29.

Synthesis of target 34 is shown in Scheme 5 (Method D). An imidazole (30) is alkylated with 2-bromoacetonitrile to give compound 31. Reaction of 31 with DMF-DMA, followed condensation with hydrazine, provides amino-pyrazole 33. Subsequent reaction of compound 33 with β-ketoester 2 then furnishes target 34.

Scheme 6 (Method E)

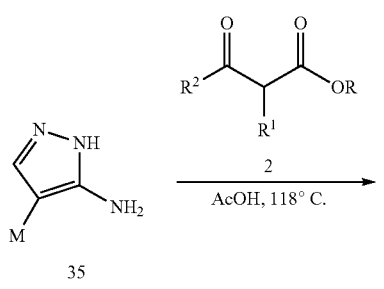

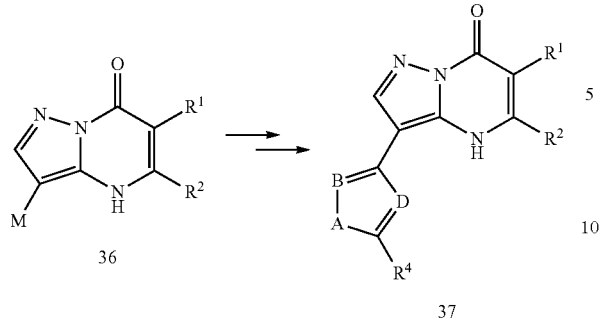

Similarly, an amino-pyrazole 35, in which the R group is an aldehyde or nitrile or ethyl, can also be condensed with β-ketoester 2 to give compound 36. The R group can then be further transformed into a variety of other 5-membered heterocyclyls.

Scheme 7 (Method F)

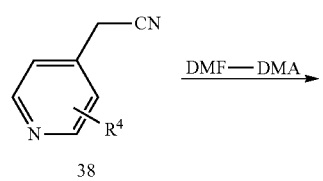

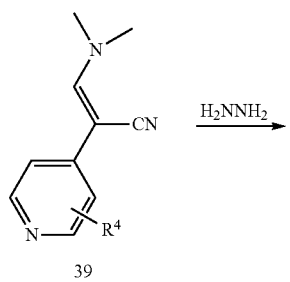

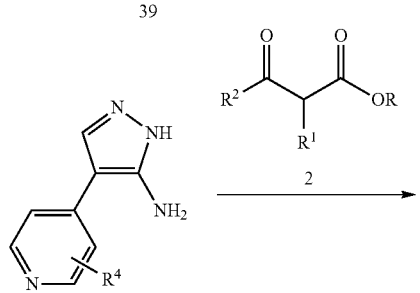

A general synthetic scheme for target 41 with a 6-membered heterocyclyl is described in Scheme 7. Reaction of nitrile 38 with DMF-DMA, followed by condensation with hydrazine, provides aminopyrazole 40. Subsequent reaction of aminopyrazole 40 with a β-ketoester 2 then furnishes target 41.

In one embodiment the invention provides a method for preparing a compound of formula (I) comprising:

a) coupling a compound of formula 100 or a salt thereof:

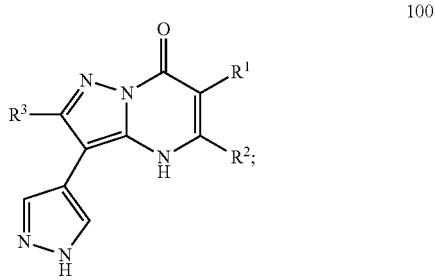

with a compound of formula R⁴—X, wherein X is a halogen;

b) acylating a compound of formula 100 or a salt thereof with a compound of formula R⁴—X, wherein X is suitable leaving group;

c) treating a compound of formula 101 or a salt thereof with a compound of formula 102 in the presence of a suitable acid to provide a compound of formula (I):

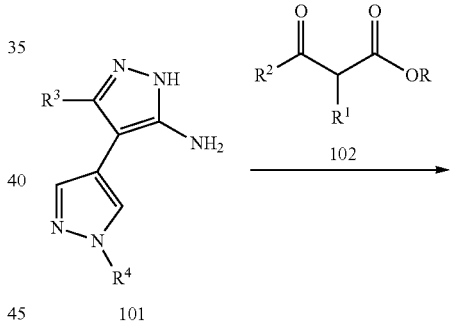

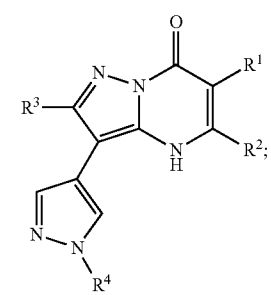

d) treating a compound of formula 103 or a salt thereof with a compound of formula 102 in the presence of a suitable acid to provide a compound of formula (I):

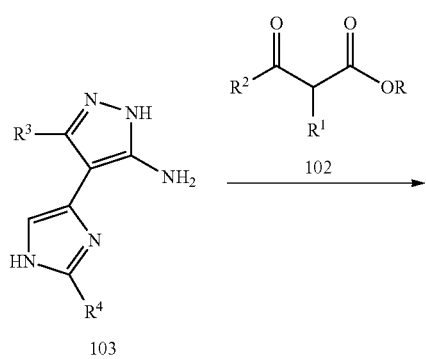

103

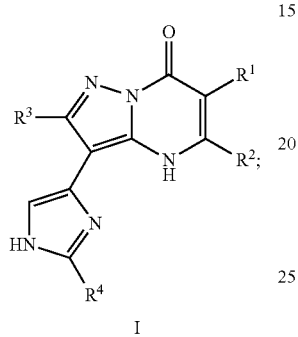

I e) treating a compound of formula 104 or a salt thereof with a compound of formula 102 in the presence of a suitable acid to provide a compound of formula (I):

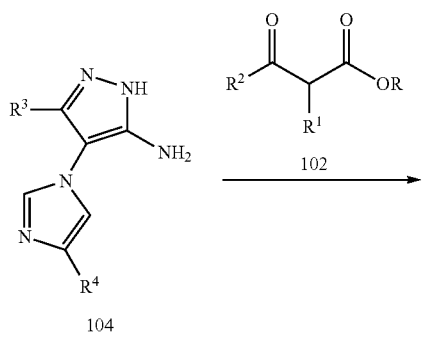

104

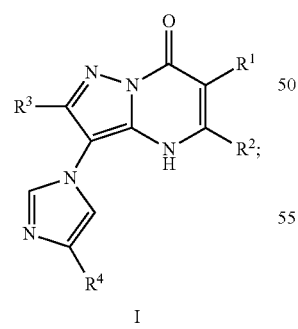

I or f) treating a compound of formula 105 or a salt thereof wherein M is —C(O)H, —CN, —C(O)OH or —C(O)O(C$_{1-6}$ alkyl), with a compound of formula 102 in the presence of a suitable acid to provide a compound of formula (I):

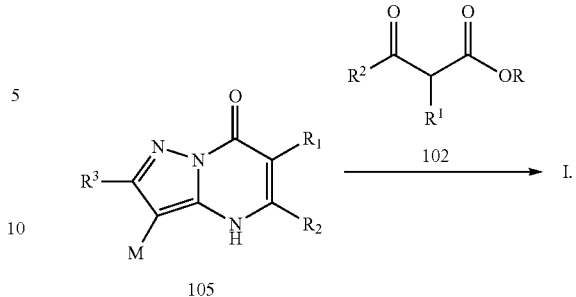

105

Another aspect includes compounds of formulae 101-105 and salts thereof that are useful for preparing compounds of formula (I).

Embodiments are illustrated by the following examples.

EXAMPLES

Example 1

Step 1

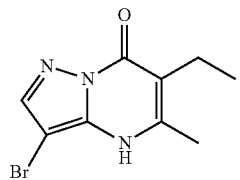

3-bromo-6-ethyl-5-methylpyrazolo[1,5-a]pyrimidin-7(4H)-one

A mixture of 4-bromo-1H-pyrazol-5-amine (16.1 g, 100.0 mmol) and ethyl 2-ethyl-3-oxobutanoate (19.0 g, 120.0 mmol) in AcOH (300 mL) was heated at reflux for 4 h. After evaporation of the solvent, the residue was washed with MTBE (200 mL×3). The resulting solid was collected by filtration and dried to give the crude title compound (17.0 g, 67% yield). It was used directly for next step without further purification. LCMS (ESI) m/z: 255.9 [M+H$^+$].

Step 2

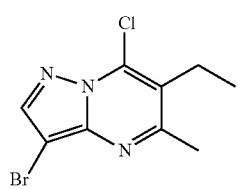

3-bromo-7-chloro-6-ethyl-5-methylpyrazolo[1,5-a]pyrimidine

POCl$_3$ (60.8 g, 400.0 mmol) was added dropwise to a stirred and cooled (0° C.) mixture of 3-bromo-6-ethyl-5-methylpyrazolo[1,5-a]pyrimidin-7(4H)-one (25.6 g, 100.0 mmol) and DIPEA (51.6 g, 400.0 mmol) in toluene (500 mL). After addition, the mixture was allowed to warm to 90° C. and stirring continued for 4 h, at which time LC-MS showed completion of the conversion. The solvent was removed under reduced pressure and the residue was adjusted to pH=9 by adding aqueous NaHCO$_3$. The resulting mixture was extracted with EtOAc (300 mL×3). The combined organic layers were dried (Na$_2$SO$_4$) and evaporated. The residue was purified by flash chromatography (PE/EtOAc=10:1) to give the title compound (15.0 g, 55% yield) as yellow solid. LCMS (ESI) m/z: 273.9 [M+H$^+$].

Step 3

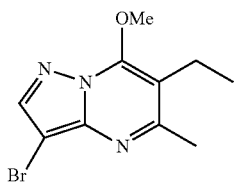

3-bromo-6-ethyl-7-methoxy-5-methylpyrazolo[1,5-a]pyrimidine

NaOMe (2.70 g, 50.0 mmol) was added portionwise to a stirred solution of 3-bromo-7-chloro-6-ethyl-5-methylpyrazolo[1,5-a]pyrimidine (2.74 g, 10.0 mmol) in methanol (50 mL). After addition, the reaction mixture was stirred at room temperature for 4 h, at which time LC-MS showed completion of the reaction. The solvent was evaporated under reduced pressure, and the residue was diluted with water (50 mL). The resulting mixture was extracted with EtOAc (100 mL×3). The combined organic layers were dried and concentrated to give the crude title compound (2.40 g, 89% yield). This crude was used in the next step without further purification. LCMS (ESI) m/z: 269.9 [M+H$^+$].

Step 4

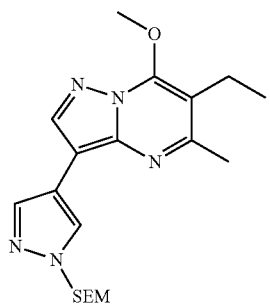 [SMILES: CCc1c(C)nc2c(-c3cnn(COCC[Si](C)(C)C)c3)cnn2c1OC]

6-ethyl-7-methoxy-5-methyl-3-(1-((2-(trimethylsilyl)ethoxy)methyl)-1H-pyrazol-4-yl)pyrazolo[1,5-a]pyrimidine A mixture of 3-bromo-6-ethyl-7-methoxy-5-methylpyrazolo[1,5-a]pyrimidine (2.70 g, 10.0 mmol), 4-(4,4,5,5-tetramethyl-1,3,2-dioxaborolan-2-yl)-1-((2-(trimethylsilyl)ethoxy)methyl)-1H-pyrazole (4.86 g, 15.0 mmol), Pd(PPh$_3$)$_2$Cl$_2$ (0.50 g, 0.7 mmol) and Cs$_2$CO$_3$(6.50 g, 20.0 mmol) in dioxane/H$_2$O (50 mL/10 mL) was heated at reflux for 10 h under nitrogen protection. The organic solvent was removed under reduced pressure, and the residue was extracted with EtOAC (50 mL×3). The combined organic layers were dried and evaporated. The residue was purified by flash column (PE/EtOAc=10:1) to give the title compound (1.30 g, 34% yield) as yellow oil. LCMS (ESI) m/z: 388.0 [M+H$^+$].

Step 5

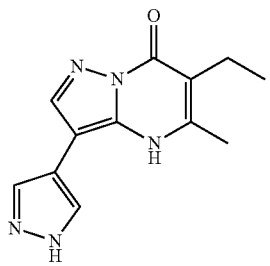 [SMILES: CCc1c(C)[nH]c2c(-c3cn[nH]c3)cnn2c1=O]

6-ethyl-5-methyl-3-(1H-pyrazol-4-yl)pyrazolo[1,5-a]pyrimidin-7(4H)-one

A mixture of 6-ethyl-7-methoxy-5-methyl-3-(1-((2-(trimethylsilyl)ethoxy)methyl)-1H-pyrazol-4-yl)pyrazolo[1,5-a]pyrimidine (3.87 g, 10.0 mmol) in MeOH (50 mL) and HCl (2 N, 10 mL, 20.0 mmol) was heated at reflux for 2 h. The solvent was removed under reduced pressure, and the residue was diluted by addition of saturated aqueous NaHCO$_3$. The resulting mixture was extracted with EtOAc (100 mL×3). The combined organic layers were dried and evaporated. The residue was purified by flash column (DCM/MeOH=10:1) to give the title compound (1.90 g, 78% yield) as a yellow solid. LCMS (ESI) m/z: 243.9 [M+H$^+$].

Step 6

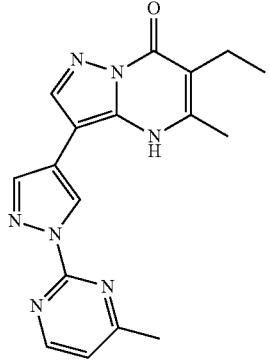 [SMILES: CCc1c(C)[nH]c2c(-c3cnn(-c4nccc(C)n4)c3)cnn2c1=O]

6-ethyl-5-methyl-3-(1-(4-methylpyrimidin-2-yl)-1H-pyrazol-4-yl[1,5-a]pyrimidin-7(4H)-one NaH (60%, 40 mg, 1.0 mmol) was added to a stirred and cooled (0° C.) solution of 6-ethyl-5-methyl-3-(1H-pyrazol-4-yl)pyrazolo[1,5-a]pyrimidin-7(4H)-one (122 mg, 0.5 mmol) in DMF (5 ml). Stirring was continued for 1 h at room temperature before 2-chloro-4-methylpyrimidine (128 mg, 1.0 mmol) was added. The reaction mixture was then stirred at room temperature for 12 h and quenched by addition of saturated aqueous NH$_4$Cl (0.1 mL). The solvent was evaporated, and the residue was purified by preparative HPLC to afford the title compound (22 mg, 13% yield) as a yellow solid. $^1$H NMR (400 MHz, DMSO-d$_6$): δ 11.50 (d, J=2.0 Hz, 1H), 9.06 (d, J=0.8 Hz, 1H), 8.70 (d, J=4.8 Hz, 1H), 8.22 (d, J=0.8 Hz, 1H), 8.19 (s, 1H), 7.35 (d, J=4.8 Hz, 1H), 2.54 (s, 3H), 2.46-2.48 (m, 2H), 2.41 (s, 3H), 1.02 (t, J=7.6 Hz, 3H). LCMS (Method C): Rt=0.711 min, m/z: 335.9 [M+H$^+$].

Example 2

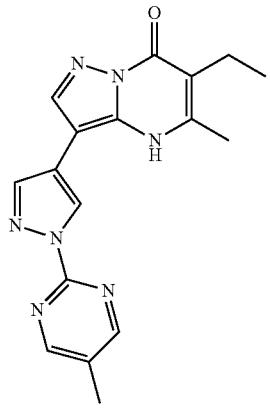 [SMILES: CCc1c(C)[nH]c2c(-c3cnn(-c4ncc(C)cn4)c3)cnn2c1=O]

6-ethyl-5-methyl-3-(1-(5-methylpyrimidin-2-yl)-1H-pyrazol-4-yl)pyrazolo[1,5-a]pyrimidin-7(4H)-one In a similar procedure as shown in Example 1, the title compound was prepared in 15% yield from 2-chloro-5-methylpyrimidine. NMR (400 MHz, DMSO-d$_6$): δ 11.43 (s, 1H), 9.06 (s, 1H), 8.70 (s, 2H), 8.19 (s, 2H), 2.45-2.47 (m, 2H), 2.40 (s, 3H), 2.29 (s, 3H), 1.02-0.98 (m, 3H). LCMS (Method C): RT=0.721 min, m/z: 335.9 [M+H$^+$].

Example 3

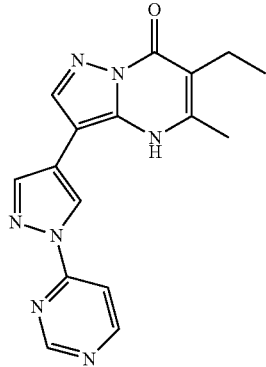 [SMILES: CCc1c(C)[nH]c2c(-c3cnn(-c4ccncn4)c3)cnn2c1=O]

6-ethyl-5-methyl-3-(1-(pyrimidin-4-yl)-1H-pyrazol-4-yl)pyrazolo[1,5-a]pyrimidin-7(4H)-one In a similar procedure as shown in Example 1, the title compound was prepared in 19% yield from 4-chloropyrimidine. $^1$H NMR (400 MHz, DMSO-d$_6$): δ 9.18 (s, 1H), 9.11 (s, 1H), 8.87 (d, J=5.2 Hz, 1H), 8.37 (s, 1H), 8.22 (s, 1H), 7.95 (d, J=5.2 Hz, 1H), 2.48-2.45 (m, 2H), 2.42 (s, 3H), 1.03 (t, J=6.8 Hz, 3H). LCMS (Method C): RT=0.713 min, m/z: 321.8, 665.1 [M+H$^+$, 2M+1].

Example 4

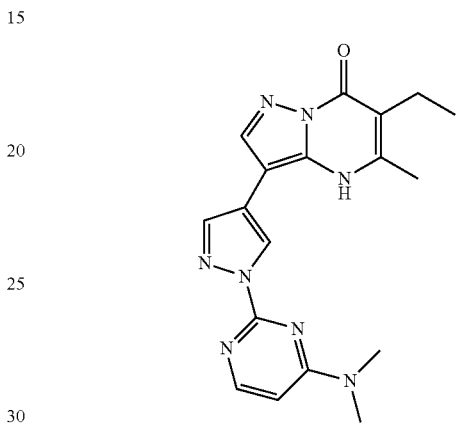

3-(1-(4-(dimethylamino)pyrimidin-2-yl)-1H-pyrazol-4-yl)-6-ethyl-5-methylpyrazolo[1,5-a]pyrimidin-7(4H)-one In a similar procedure as shown in Example 1, the title compound was prepared in 22% yield from 2-chloro-4-dimethylaminopyridimine. $^1$H NMR (400 MHz, DMSO-d$_6$): δ 11.44-11.48 (m, 1H), 8.96 (s, 1H), 8.08-8.19 (m, 3H), 6.60 (d, J=6.0 Hz, 1H), 3.06 (s, 6H), 2.47-2.45 (m, 2H), 2.39 (s, 3H), 1.02 (t, J=7.2 Hz, 3H). LCMS (Method C): RT=0.671 min, m/z: 364.9 [M+H$^+$].

Example 5

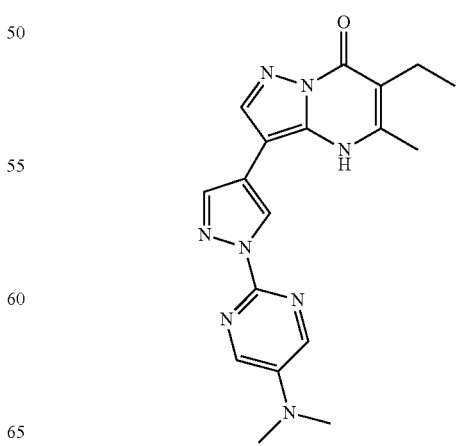

3-(1-(5-(dimethylamino)pyrimidin-2-yl)-1H-pyrazol-4-yl)-6-ethyl-5-methylpyrazolo[1,5-a]pyrimidin-7(4H)-one In a similar procedure as shown in Example 1, the title compound was prepared in 15% yield from 2-chloro-5-dimethylaminopyridimine $^1$H NMR (400 MHz, DMSO-d$_6$): δ 11.43 (s, 1H), 8.90 (d, J=0.4 Hz, 1H), 8.32 (s, 2H), 8.14 (s, 1H), 8.09 (d, J=0.8 Hz, 1H), 2.98 (s, 6H), 2.47-2.45 (m, 2H), 2.40 (s, 3H), 1.01 (t, J=7.6 Hz, 3H). LCMS (Method C): RT=0.729 min, m/z: 364.9 [M+H$^+$].

Example 6

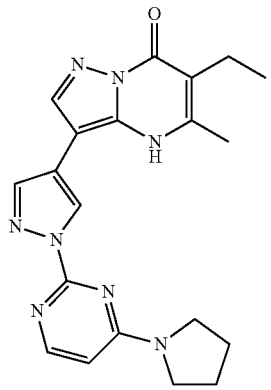 [SMILES: CCc1c(C)[nH]c2c(-c3cnn(-c4nccc(N5CCCC5)n4)c3)cnn2c1=O]

6-ethyl-5-methyl-3-(1-(4-(pyrrolidin-1-yl)pyrimidin-2-yl)-1H-pyrazol-4-yl)pyrazolo[1,5-a]pyrimidin-7(4H)-one In a similar procedure as shown in Example 1, the title compound was prepared in 10% yield from 2-chloro-4-(pyrrolidin-1-yl)pyrimidine. $^1$H NMR (400 MHz, DMSO-d$_6$): δ 11.50 (s, 1H), 8.94 (s, 1H), 8.13-8.12 (m, 3H), 6.43 (s, 1H), 3.63-3.59 (m, 4H), 2.47-2.45 (m, 2H), 2.40 (s, 3H), 1.99-1.93 (m, 4H), 1.01-1.00 (m, 3H). LCMS (Method C): RT=0.709 min, m/z: 390.9 [M+H$^+$].

Example 7

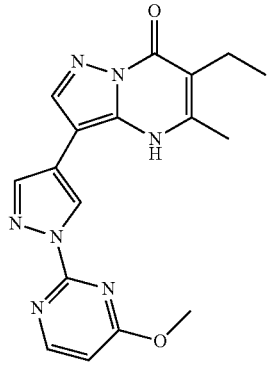 [SMILES: CCc1c(C)[nH]c2c(-c3cnn(-c4nccc(OC)n4)c3)cnn2c1=O]

6-ethyl-3-(1-(4-methoxypyrimidin-2-yl)-1H-pyrazol-4-yl)-5-methylpyrazolo[1,5-a]pyrimidin-7(4H)-one In a similar procedure as shown in Example 1, the title compound was prepared in 38% yield from 2-chloro-4-methoxypyrimidine. $^1$H NMR (400 MHz, DMSO-d$_6$): δ 9.05 (d, J=0.4 Hz, 1H), 8.55 (d, J=5.6 Hz, 1H), 8.22 (s, 1H), 8.17 (s, 1H), 6.88 (d, J=5.6 Hz, 1H), 4.03 (s, 3H), 2.45 (q, J=1.6 Hz, 2H), 2.41 (s, 3H), 1.02 (t, J=7.2 Hz, 3H). LCMS (Method C): RT=0.724 min, m/z: 351.8 [M+H$^+$].

Example 8

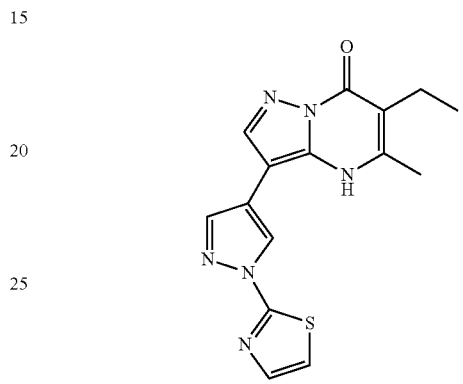

6-ethyl-5-methyl-3-(1-(thiazol-2-yl)-1H-pyrazol-4-yl)pyrazolo[1,5-a]pyrimidin-7(4H)-one In a similar procedure as shown in Example 1, the title compound was prepared in 10% yield from 2-bromothiazole. $^1$H NMR (400 MHz, DMSO-d$_6$): δ11.44 (s, 1H), 9.02 (d, J=0.4 Hz, 1H), 8.24 (d, J=0.4 Hz, 1H), 8.20 (s, 1H), 7.66 (d, J=3.6 Hz, 1H), 7.54 (d, J=3.6 Hz, 1H), 2.49-2.48 (m, 2H), 2.48 (s, 3H), 1.03 (t, J=7.2 Hz, 3H). LCMS (Method C): RT=0.756 min, m/z: 326.9 [M+H$^+$].

Example 9

Step 1

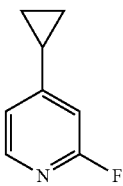

4-cyclopropyl-2-fluoropyridine

A mixture of 4-bromo-2-fluoropyridine (500 mg, 2.81 mmol), cyclopropylboronic acid (295 mg, 3.47 mmol), Pd(dppf)Cl$_2$ (223 mg, 0.30 mmol) and Cs$_2$CO$_3$ (1.86 g, 5.72 mmol) in dioxane/H$_2$O (16 mL/4 mL) was heated at 120° C. for 30 min under microwave conditions (with nitrogen protection). After being cooled, the mixture was filtered. The filtrate was evaporated and the residue was purified by flash chromatography on silica gel to give the title compound (100 mg, 26% yield) as an oil, which was used in the next step without purification.

Step 2

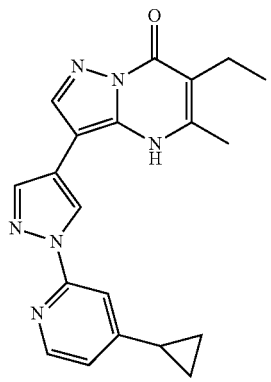 [SMILES: CCc1c(C)[nH]c2c(-c3cnn(-c4cc(C5CC5)ccn4)c3)cnn2c1=O]

3-(1-(4-cyclopropylpyridin-2-yl)-1H-pyrazol-4-yl)-6-ethyl-5-methylpyrazolo[1,5-a]pyrimidin-7(4H)-one In a similar procedure as shown in Example 1, the title compound was prepared in 6.5% yield from 4-cyclopropyl-2-fluoropyridine. $^1$H NMR (400 MHz, DMSO-d$_6$): δ 9.06 (d, J=0.8 Hz, 1H), 8.31 (d, J=5.6 Hz, 1H), 8.19-8.18 (m, 2H), 7.70 (d, J=1.2 Hz, 1H), 7.04 (dd, J=1.6, 5.2 Hz, 1H), 2.52-2.51 (m, 2H), 2.43 (s, 3H), 2.14-2.07 (m, 1H), 1.15-1.13 (m, 2H), 1.05 (t, J=7.2 Hz, 3H), 0.90-0.89 (m, 2H). LCMS (Method C): RT=0.816 min, m/z: 360.9 [M+H+].

Example 10

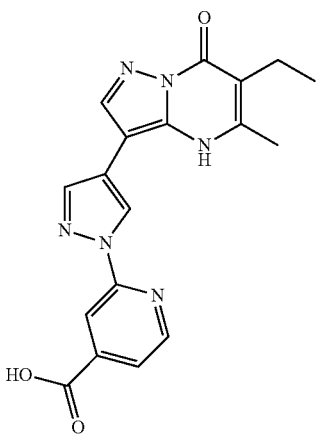 [SMILES: CCc1c(C)[nH]c2c(-c3cnn(-c4cc(C(=O)O)ccn4)c3)cnn2c1=O]

2-(4-(6-ethyl-5-methyl-7-oxo-4,7-dihydropyrazolo[1,5-a]pyrimidin-3-yl)-1H-pyrazol-1-yl)isonicotinic acid In a similar procedure as shown in Example 1, the title compound was prepared in 6.6% yield from 2-fluoroisonicotinic acid. $^1$H NMR (400 MHz, DMSO-d$_6$): δ 11.50 (br. s, 1H), 9.15 (s, 1H) 8.68 (d, J=5.2 Hz, 1H), 8.36 (s, 1H), 8.28-8.22 (m, 3H), 7.77 (d, J=4.8 Hz, 1H), 2.51-2.50 (m, 2H), 2.44 (s, 3H), 1.05 (m, 3H). LCMS (Method C): RT=0.736 min, m/z: 364.9 [M+H+].

Example 11

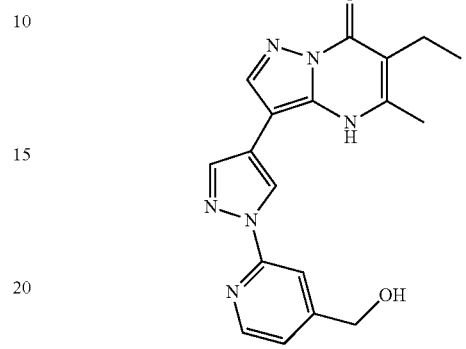

6-ethyl-3-(1-(4-(hydroxymethyl)pyridin-2-yl)-1H-pyrazol-4-yl)-5-methylpyrazolo[1,5-a]pyrimidin-7(4H)-one Borane (1 M in THF, 0.2 mL, 0.2 mmol) was added dropwise to a stirred and cooled (0° C.) solution of 2-(4-(6-ethyl-5-methyl-7-oxo-4,7-dihydropyrazolo[1,5-a]pyrimidin-3-yl)-1H-pyrazol-1-yl)isonicotinic acid (40 mg, 0.11 mmol) in THF (5 mL). After addition, the reaction mixture was warmed to room temperature and stirring continued for 48 h, at which time LC-MS showed the completion of reaction. The reaction was quenched by addition of MeOH (5 mL) and then evaporated. The residue was purified by preparative HPLC to give the title compound (7 mg, 18.2% yield) as a white solid. $^1$H NMR (400 MHz, DMSO-d$_6$) δ 11.52 (br. s, 1H), 9.10 (s, 1H), 8.43 (d, J=4.8 Hz, 1H), 8.21 (d, J=8.8 Hz, 2H), 7.97 (s, 1H), 7.28 (d, J=4.8 Hz, 1H), 5.61 (t, J=6.0 Hz, 1H), 4.65 (d, J=5.6 Hz, 2H), 2.52-2.50 (m, 2H), 2.44 (s, 3H), 1.05 (t, J=7.2 Hz, 3H). LCMS (Method C): RT=0.716 min, m/z: 350.9 [M+H+].

Example 12

Step 1

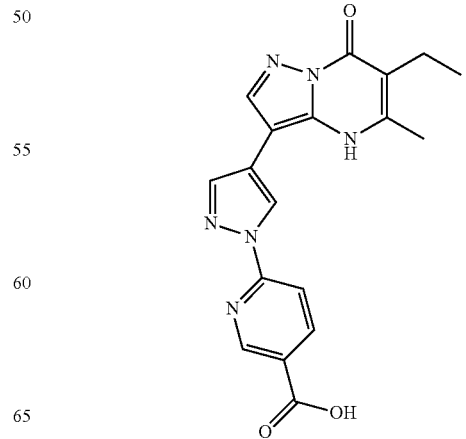

6-(4-(6-ethyl-5-methyl-7-oxo-4,7-dihydropyrazolo pyrimidin-3-yl)-1H-pyrazol-1-yl)nicotinic acid In a similar procedure as shown in Example 1, the crude title compound was prepared in 34% yield from 6-fluoronicotinic acid. The crude material was applied to next step without further purification.

Step 2

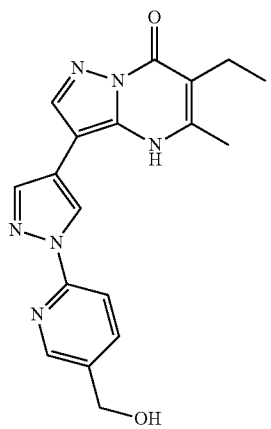 [SMILES: CCc1c(C)[nH]c2c(-c3cnn(-c4ccc(CO)cn4)c3)cnn2c1=O]

6-ethyl-3-(1-(5-(hydroxymethyl)pyridin-2-yl)-1H-pyrazol-4-yl)-5-methylpyrazolo[1,5-a]pyrimidin-7(4H)-one In a similar procedure as shown in Example 11, the title compound was prepared in 8% yield from 6-(4-(6-ethyl-5-methyl-7-oxo-4,7-dihydropyrazolo[1,5-a]pyrimidin-3-yl)-1H-pyrazol-1-yl)nicotinic acid. $^1$H NMR (400 MHz, DMSO-d$_6$): δ 9.06 (s, 1H), 8.41 (s, 1H), 8.18 (s, 1H), 8.15 (s, 1H), 7.92 (d, J=1.2 Hz, 2H), 5.37 (d, J=5.6 Hz, 1H), 4.55 (d, J=5.2 Hz, 1H), 2.48-2.45 (m, 2H), 2.40 (s, 3H), 1.02 (t, J=7.6 Hz, 3H). LCMS (Method C): RT=0.709 min, m/z: 350.8 [M+H$^+$].

Example 13

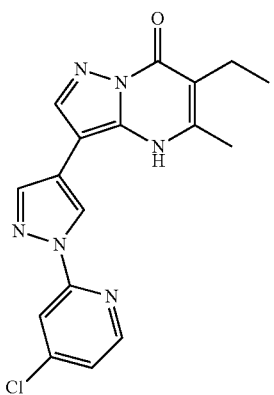 [SMILES: CCc1c(C)[nH]c2c(-c3cnn(-c4cc(Cl)ccn4)c3)cnn2c1=O]

3-(1-(4-chloropyridin-2-yl)-1H-pyrazol-4-yl)-6-ethyl-5-methylpyrazolo[1,5-a]pyrimidin-7(4H)-one A mixture of 6-ethyl-5-methyl-3-(1H-pyrazol-4-yl)pyrazolo[1,5-a]pyrimidin-7(4H)-one (100 mg, 0.41 mmol), 2-bromo-4-chloropyridine (117 mg, 0.62 mmol), Pd$_2$(dba)$_3$ (38 mg, 0.04 mmol), Xantphos (47 mg, 0.08 mmol) and Cs$_2$CO$_3$ (268 mg, 0.82 mmol) in dioxane (4 mL) was sealed in a microwave vial, purged with nitrogen and irradiated at 140° C. for 1 h under microwave conditions. After cooling, the reaction mixture was partitioned between ethyl acetate and water. The organic layer was washed with brine, dried over Na$_2$SO$_4$ and evaporated. The residue was purified by preparative HPLC to give the title compound (40 mg, 28% yield) as a white solid. $^1$H NMR (400 MHz, DMSO-d6): δ 11.49 (br. s, 1H), 9.09 (s, 1H), 8.49 (d, J=5.2 Hz, 1H), 8.27 (s, 1H), 8.22 (s, 1H), 7.98 (s, 1H), 7.50 (d, J=4.4 Hz, 1H), 2.50-2.48 (m, 2H), 2.44 (s, 3H), 1.05 (t, J=7.2 Hz, 3H). LCMS (Method C): RT=0.805 min, m/z: 354.8, 709.1 [M+H$^+$, 2M+1].

Example 14

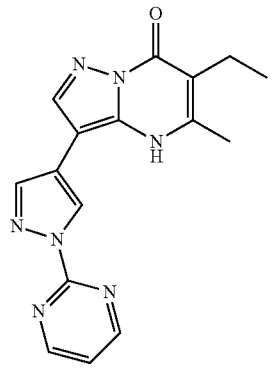 [SMILES: CCc1c(C)[nH]c2c(-c3cnn(-c4ncccn4)c3)cnn2c1=O]

6-ethyl-5-methyl-3-(1-(pyrimidin-2-yl)-1H-pyrazol-4-yl)pyrazolo[1,5-a]pyrimidin-7(4H)-one A mixture of 6-ethyl-5-methyl-3-(1H-pyrazol-4-yl)pyrazolo[1,5-a]pyrimidin-7(4H)-one (120 mg, 0.49 mmol), 2-chloropyrimidine (84 mg, 0.74 mmol), CuI (47 mg, 0.25 mmol), N,N-dimethylethylenediamine (22 mg, 0.25 mmol) and Cs$_2$CO$_3$ (241 mg, 0.74 mmol) in dioxane (6 mL) was stirred at 110° C. for 12 h under nitrogen atmosphere. After cooling, the reaction mixture was partitioned between ethyl acetate and water. The organic layer was washed with ammonia (5%, 5 mL×2), brine (10 mL×2), dried (Na$_2$SO$_4$) and evaporated. The residue was purified by preparative HPLC to afford the title compound (31 mg, 20% yield) as a white solid. $^1$H NMR (400 MHz, DMSO-d$_6$) δ 11.47-11.44 (m, 1H), 9.12 (s, 1H), 8.89 (d, J=4.8 Hz, 2H), 8.26 (s, 1H), 8.20 (s, 1H), 7.48 (t, J=4.8 Hz, 1H), 2.48-2.47 (m, 2H), 2.42 (s, 3H), 1.03 (t, J=7.2 Hz, 3H). LCMS (Method C): RT=0.690 min, m/z: 321.8, 665.1 [M+H$^+$, 2M+1].

Example 15

Step 1

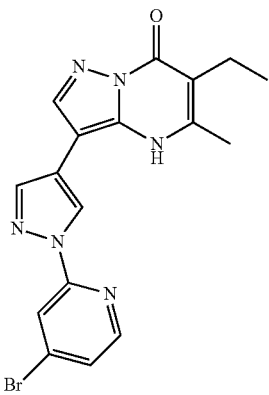

3-(1-(4-bromopyridin-2-yl)-1H-pyrazol-4-yl)-6-ethyl-5-methylpyrazolo[1,5-a]pyrimidin-7(4H)-one A solution of 6-ethyl-5-methyl-3-(1H-pyrazol-4-yl)pyrazolo[1,5-a]pyrimidin-7(4H)-one (400 mg, 1.65 mmol) in DMF (5 mL) was added dropwise to a cooled (0° C.) suspension of NaH (60%, 99 mg, 2.47 mmol) in DMF (3 mL). Stirring was continued for 30 min, and then 4-bromo-2-fluoropyridine (432 mg, 2.47 mmol) was added in portions. After addition, the resultant mixture was stirred at room temperature for 8 h, and then poured in water (20 mL). After filtration, the solid cake was dried to give the title compound (480 mg, 73% yield) as a white solid. This was used directly into the next step with further purification.

Step 2

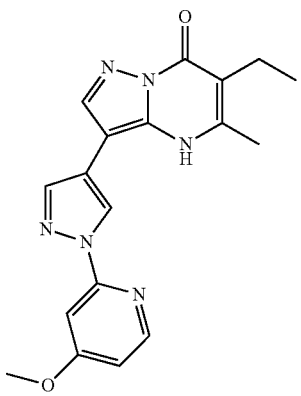 [SMILES: CCc1c(C)[nH]c2c(-c3cnn(-c4cc(OC)ccn4)c3)cnn2c1=O]

6-ethyl-3-(1-(4-methoxypyridin-2-yl)-1H-pyrazol-4-yl)-5-methylpyrazolo[1,5-a]pyrimidin-7(4H)-one NaOMe (33 mg, 0.61 mmol) was added to a stirred solution of 3-(1-(4-bromopyridin-2-yl)-1H-pyrazol-4-yl)-6-ethyl-5-methylpyrazolo[1,5-a]pyrimidin-7(4H)-one (80 mg, 0.20 mmol) in DMF (3 mL). The mixture was heated at 135° C. for 12 h and then quenched by addition of saturated aqueous NH$_4$Cl (1 mL). The mixture was filtered and the filtrate was evaporated. The residue was purified by preparative HPLC to give the title compound (10 mg, 14% yield) as a white solid. $^1$H NMR (400 MHz, CD$_3$OD): δ 8.89 (s, 1H), 8.28 (s, 1H), 8.06 (s, 1H), 8.37 (s, 2H), 7.54 (s, 1H), 6.92 (s, 1H), 3.98 (s, 3H), 2.70-2.60 (m, 2H), 2.51 (s, 3H), 1.17 (t, J=6.8 Hz, 3H). LCMS (Method C): RT=0.757 min, m/z: 350.9, 701.1 [M+H$^+$, 2M+1].

Example 16

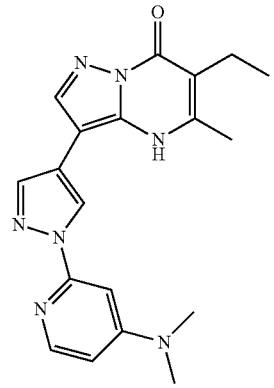 [SMILES: CCc1c(C)[nH]c2c(-c3cnn(-c4cc(N(C)C)ccn4)c3)cnn2c1=O]

3-(1-(4-(dimethylamino)pyridin-2-yl)-1H-pyrazol-4-yl)-6-ethyl-5-methylpyrazolo[1,5-a]pyrimidin-7(4H)-one A mixture of 3-(1-(4-bromopyridin-2-yl)-1H-pyrazol-4-yl)-6-ethyl-5-methylpyrazolo[1,5-a]pyrimidin-7(4H)-one (300 mg, 0.75 mmol) and dimethylamine hydrochloride (916 mg, 11.30 mmol) in DMF (10.0 mL) was treated with DIPEA (1.46 g, 11.31 mmol) and then heated at 150° C. for 30 min under microwave conditions. The resulting mixture was filtered and the filtrate was evaporated. The residue was purified by preparative HPLC to give the title compound (22.8 mg, 8.4% yield) as a white solid. $^1$H NMR (400 MHz, DMSO-d$_6$): δ 8.97 (s, 1H), 8.27 (s, 1H), 6.59 (dd, J=2.4, 6.0 Hz, 1H), 3.03 (s, 6H), 2.48 (t, J=1.6 Hz, 2H), 2.38 (s, 3H), 1.02 (t, J=7.2 Hz, 3H). LCMS (Method C): RT=0.668 min, m/z: 364.1 [M+H$^+$].

Example 17

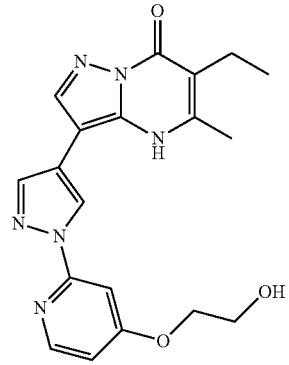 [SMILES: CCc1c(C)[nH]c2c(-c3cnn(-c4cc(OCCO)ccn4)c3)cnn2c1=O]

6-ethyl-3-(1-(4-(2-hydroxyethoxy)pyridin-2-yl)-1H-pyrazol-4-yl)-5-methylpyrazolo[1,5-a]pyrimidin-7(4H)-one NaH (60% dispersion in mineral oil, 24 mg, 0.6 mmol) was added to a stirred solution of ethane-1,2-diol (25 mg, 0.4 mmol) in DMF (2 ml). The mixture was stirred for 30 min at room temperature, then 3-(1-(4-bromopyridin-2-yl)-1H-pyrazol-4-yl)-6-ethyl-5-methylpyrazolo[1,5-a]pyrimidin-7(4H)-one (80 mg, 0.2 mmol) was added. The reaction mixture was then heated at 100° C. for 1 h. After cooling, the mixture was quenched by addition of saturated aqueous NH₄Cl (0.2 mL). The solvent was evaporated and the residue was purified by preparative HPLC to give the title compound (13 mg, 17.0% yield) as a white solid. ¹H NMR (400 MHz, DMSO-d₆): δ 11.59 (s, 1H), 9.16 (s, 1H), 8.31 (d, J=6.0 Hz, 1H), 8.24 (s, 1H), 8.21 (s, 1H), 7.51 (d, J=2.0 Hz, 1H), 7.00-6.98 (m, 1H), 4.22 (t, J=4.8 Hz, 2H), 3.77 (t, J=4.8 Hz, 2H), 2.51-2.50 (m, 2H), 2.45 (s, 3H), 1.04 (t, J=7.4 Hz, 3H). LCMS (Method C): RT=0.719 min, m/z: 380.9 [M+H⁺].

Example 18

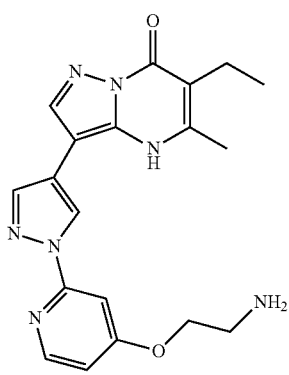 [SMILES: CCc1c(C)[nH]c2c(-c3cnn(-c4cc(OCCN)ccn4)c3)cnn2c1=O]

3-(1-(4-(2-aminoethoxy)pyridin-2-yl)-1H-pyrazol-4-yl)-6-ethyl-5-methylpyrazolo[1,5-a]pyrimidin-7(4H)-one NaH (60%, 24 mg, 0.60 mmol) was added to a stirred solution of tert-butyl (2-hydroxyethyl) carbamate (80 mg, 0.50 mmol) in DMF (2 ml). The mixture was stirred for 30 min at room temperature, then 3-(1-(4-bromopyridin-2-yl)-1H-pyrazol-4-yl)-6-ethyl-5-methylpyrazolo[1,5-a]pyrimidin-7(4H)-one (100 mg, 0.25 mmol) was added. The reaction mixture was then heated at 100° C. for 1 h. After evaporation of the solvent, the residue was diluted with HCl (2 M in EtOAc, 2 mL) and stirred for 2 h. The mixture was concentrated and the residue was purified by preparative HPLC to give the title compound (18 mg, 18.7% yield) as oil. ¹H NMR (400 MHz, DMSO-d6): δ 11.52 (br. s, 1H), 9.10 (s, 1H), 8.37 (d, J=5.6 Hz, 1H), 8.23-8.21 (m, 5H), 7.51 (d, J=3.2 Hz, 1H), 7.02-7.00 (m, 1H), 4.40 (d, J=5.2 Hz, 1H), 3.27 (q, J=5.2 Hz, 1H), 2.50-2.48 (m, 2H), 2.45 (s, 3H), 1.05 (t, J=7.6 Hz, 3H). LCMS (Method C): RT=0.668 min, m/z: 379.9 [M+H⁺].

Example 19

Step 1

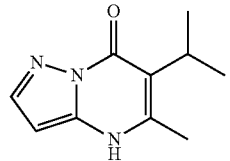

6-isopropyl-5-methylpyrazolo[1,5-a]pyrimidin-7(4H)-one

A mixture of 1H-pyrazol-5-amine (5.0 g, 60.2 mmol) and 2-acetyl-3-methylbutanoate (9.1 g, 52.8 mmol) in AcOH (50 mL) was heated at 140° C. for 5 h. After evaporation of the solvent, the residue was washed with a mixture of PE and EtOAc (200 mL, 5:1) to give the crude title compound (4.1 g, 36% yield) as a white solid. LCMS (ESI) m/z: 192.0 [M+H⁺].

Step 2

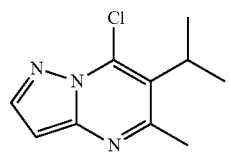

7-chloro-6-isopropyl-5-methylpyrazolo[1,5-a]pyrimidine

POCl₃ (3.2 g, 21.3 mmol) was added dropwise to a stirred and cooled (0° C.) mixture of 6-isopropyl-5-methylpyrazolo[1,5-a]pyrimidin-7(4H)-one (1.0 g, 5.2 mmol) and DIPEA (2.7, 21.3 mmol) in toluene (15 mL). After addition, the mixture was allowed to warm to 120° C. and stirring continued for 12 h, at which time LC-MS showed complete conversion. The solvent was removed under reduced pressure and the residue was adjusted to pH=9 by adding aqueous NaHCO₃. The resulting mixture was extracted with EtOAc (30 ml 3). The combined organic layers were dried over Na₂SO₄ and evaporated. The residue was purified by flash chromatography (PE/EtOAc=15:1) to give the title compound (0.9 g, 82% yield) as a yellow oil. LCMS (ESI) m/z: 210.0 [M+H⁺].

Step 3

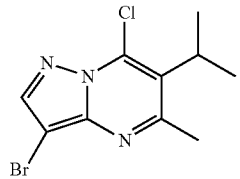

3-bromo-7-chloro-6-isopropyl-5-methylpyrazolo[1,5-a]pyrimidine

NBS (710 mg, 4.0 mmol) in CH₃CN (10 mL) was added in portions to a stirred solution of 7-chloro-6-isopropyl-5-methylpyrazolo[1,5-a]pyrimidine (800 mg, 3.8 mmol) in DCM (10 mL) over a period of 30 min at room temperature. After addition, the mixture was stirred for another 1 h at room temperature, at which time TLC showed the complete conversion. The solvent was evaporated and the residue was purified by silica gel chromatography eluted with PE/EtOAc (20:1) to give the title compound (900 mg, 82% yield) as a yellow oil. LCMS (ESI) m/z: 287.9, 289.9 [M+H⁺].

Step 4

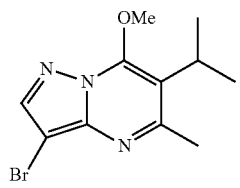 [SMILES: COc1c(C(C)C)c(C)nc2c(Br)cnn12]

3-bromo-6-isopropyl-7-methoxy-5-methylpyrazolo[1,5-a]pyrimidine

NaOMe (810 mg, 15.0 mmol) was added portionwise to a stirred solution of 3-bromo-7-chloro-6-isopropyl-5-methylpyrazolo[1,5-a]pyrimidine (900 mg, 3.1 mmol) in methanol (10 mL). After addition, the reaction mixture was stirred at room temperature for 4 h, at which time LCMS showed completion of the reaction. The solvent was evaporated under reduced pressure, and the residue was diluted with water (50 mL). The resulting mixture was extracted with EtOAc (30 mL×3). The combined organic layers were dried and concentrated to give the title compound (800 mg, 90% yield) as a yellow oil. This crude was used in the next step without further purification. LCMS (ESI) m/z: 284.0, 286.0 [M+H⁺].

Step 5

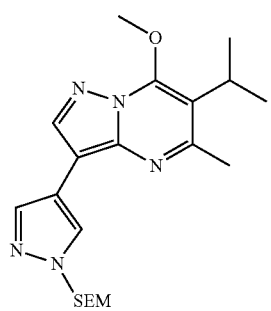

6-isopropyl-7-methoxy-5-methyl-3-(1-((2-(trimethylsilyl)ethoxy)methyl)-1H-pyrazol-4-yl)pyrazolo[1,5-a]pyrimidine A mixture of 3-bromo-6-isopropyl-7-methoxy-5-methyl-pyrazolo[1,5-a]pyrimidine (800 mg, 2.8 mmol), 4-(4,4,5,5-tetramethyl-1,3,2-dioxaborolan-2-yl)-1-((2-(trimethylsilyl)ethoxy)methyl)-1H-pyrazole (1.40 g, 4.2 mmol), Pd(PPh₃)₂Cl₂ (50 mg, 0.1 mmol) and Cs₂CO₃ (2.00 g, 6.2 mmol) in dioxane/H₂O (20 mL/40 mL) was heated at reflux for 12 h under nitrogen protection. The organic solvent was removed under reduced pressure, and the residue was extracted with EtOAC (20 mL×3). The combined organic layers were dried and evaporated. The residue was purified by flash column (PE/EtOAc=10:1) over silica gel to give the title compound (300 mg, 27% yield) as yellow oil. LCMS (ESI) m/z: 402.0 [M+H⁺].

Step 6

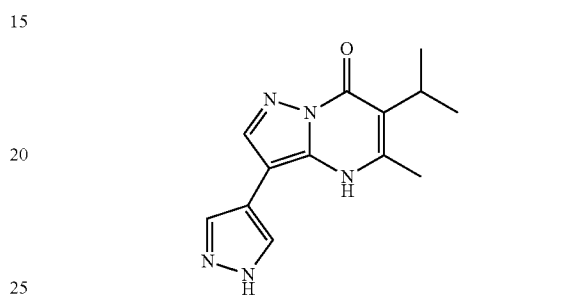

6-isopropyl-5-methyl-3-(1H-pyrazol-4-yl)pyrazolo[1,5-a]pyrimidin-7(4H)-one

A mixture of 6-isopropyl-7-methoxy-5-methyl-3-(1-((2-(trimethylsilyl)ethoxy)methyl)-1H-pyrazol-4-yl)pyrazolo[1,5-a]pyrimidine (300 mg, 0.8 mmol) in MeOH (20 mL) and HCl (2 N, 2 mL, 4.0 mmol) was heated at reflux for 2 h. The solvent was removed under reduced pressure, and the residue was diluted with addition of saturated aqueous NaHCO₃. The resulting mixture was extracted with EtOAc (20 mL×3). The combined organic layers were dried and evaporated. The residue was purified by flash column (DCM/MeOH=10:1) to the title compound (120 mg, 65% yield) as a yellow solid. LCMS (ESI) m/z: 258.0 [M+H⁺].

Step 7

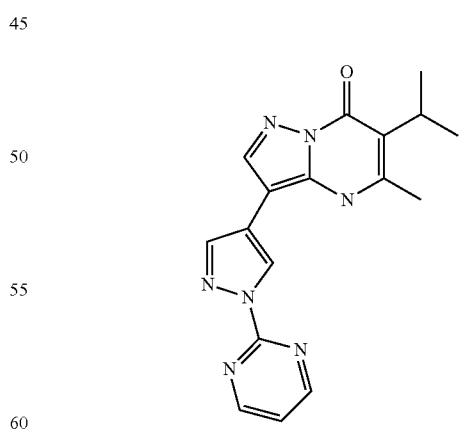

6-isopropyl-5-methyl-3-(1-(pyrimidin-2-yl)-1H-pyrazol-4-yl)pyrazolo[1,5-a]pyrimidin-7(4H)-one In a similar procedure as shown in Example 1, the title compound was prepared in 13% yield from 2-chloropyrimidine. ¹H NMR (400 MHz, DMSO-d₆): δ 11.40 (br. s, 1H), 9.13 (s, 1H), 8.90 (d, J=4.4 Hz, 2H), 8.27 (s, 1H), 8.21 (s, 1H), 7.49 (d, J=4.0 Hz, 1H), 3.06-3.03 (m, 1H), 2.46 (s, 3H), 1.31 (d, J=6.8 Hz, 6H). LCMS (Method C): RT=0.746 min, m/z: 335.9 [M+H⁺].

Example 20

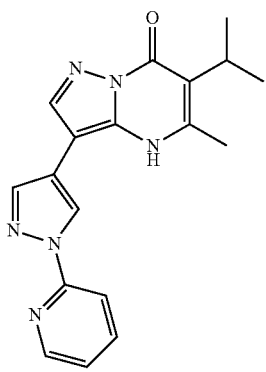 [SMILES: Cc1[nH]c2c(-c3cnn(-c4ccccn4)c3)cnn2c(=O)c1C(C)C]

6-isopropyl-5-methyl-3-(1-(pyridin-2-yl)-1H-pyrazol-4-yl)pyrazolo[1,5-a]pyrimidin-7(4H)-one In a similar procedure as shown in Example 1, the title compound was prepared in 80% yield from 2-fluoropyridine. ¹H NMR (400 MHz, DMSO-d₆): δ 11.33 (s, 1H), 9.07 (s, 1H), 8.49 (d, J=4.0 Hz, 1H), 8.16 (d, J=10.4 Hz, 2H), 8.01-7.93 (m, 2H), 7.37-7.34 (m, 1H), 3.08-3.01 (m, 1H), 2.43 (s, 3H), 1.28 (d, J=6.8 Hz, 6H). LCMS (Method C): RT=0.806 min, m/z: 334.9 [M+H⁺].

Example 21

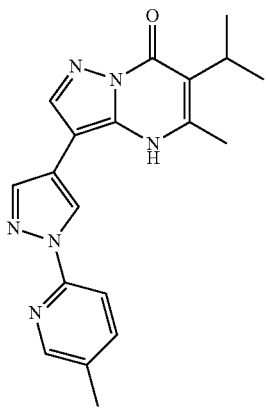 [SMILES: Cc1ccc(-n2cc(-c3cnn4c(=O)c(C(C)C)c(C)[nH]c34)cn2)nc1]

6-isopropyl-5-methyl-3-(1-(5-methylpyridin-2-yl)-1H-pyrazol-4-yl)pyrazolo[1,5-a]pyrimidin-7(4H)-one In a similar procedure as shown in Example 1, the title compound was prepared in 3% yield from 2-fluoro-5-methylpyridine. ¹H NMR (400 MHz, DMSO-d₆): δ 11.35 (br. s, 1H), 9.05 (s, 1H), 8.34 (s, 1H), 8.17-8.16 (m, 2H), 7.89-7.82 (m, 2H), 3.08-3.01 (m, 1H), 2.45 (s, 3H), 2.35 (s, 3H), 1.31 (d, J=6.8 Hz, 6H). LCMS (Method C): RT=0.824 min, m/z: 348.9 [M+H⁺].

Example 22

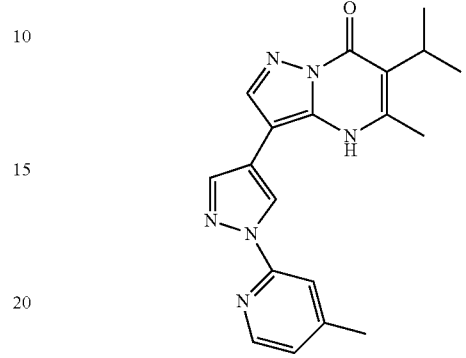

6-isopropyl-5-methyl-3-(1-(4-methylpyridin-2-yl)-1H-pyrazol-4-yl)pyrazolo[1,5-a]pyrimidin-7(4H)-one In a similar procedure as shown in Example 1, the title compound was prepared in 6% yield from 2-fluoro-4-methylpyridine. ¹H NMR (400 MHz, DMSO-d₆): δ 11.41 (br. s, 1H), 9.08 (s, 1H), 8.36 (d, J=5.2 Hz, 1H), 8.20 (d, J=8.0 Hz, 2H), 7.83 (s, 1H), 7.64-7.53 (m, 1H), 7.21 (d, J=5.2 Hz, 1H), 3.08-3.01 (m, 1H), 2.51 (s, 3H), 2.44 (s, 3H), 1.31 (d, J=6.8 Hz, 6H). LCMS (Method C): RT=0.825 min, m/z: 348.9 [M+H⁺].

Example 23

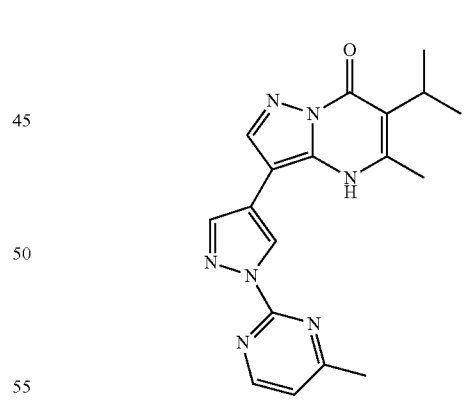

6-isopropyl-5-methyl-3-(1-(4-methylpyrimidin-2-yl)-1H-pyrazol-4-yl)pyrazolo[1,5-a]pyrimidin-7(4H)-one In a similar procedure as shown in Example 1, the title compound was prepared in 8% yield from 2-chloro-4-methylpyrimidine. ¹H NMR (400 MHz, DMSO-d₆): δ 11.41 (br. s, 1H), 9.07 (d, J=0.8 Hz, 1H), 8.72 (d, J=5.2 Hz, 1H), 8.24 (d, J=0.8 Hz, 1H), 8.20 (s, 1H), 7.37 (d, J=5.2 Hz, 1H), 3.08-3.00 (m, 1H), 2.57 (s, 3H), 2.46 (s, 3H), 1.31 (d, J=7.2 Hz, 6H). LCMS (Method C): RT=0.753 min, m/z: 349.8 [M+H⁺].

Example 24

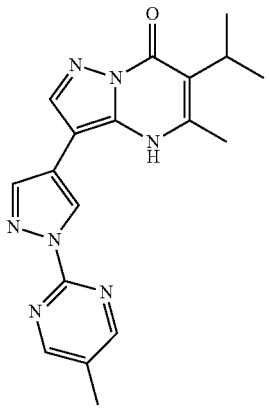 [SMILES: Cc1cnc(-n2cc(-c3cnn4c(=O)c(C(C)C)c(C)[nH]c34)cn2)nc1]

6-isopropyl-5-methyl-3-(1-(5-methylpyrimidin-2-yl)-1H-pyrazol-4-yl)pyrazolo[1,5-a]pyrimidin-7(4H)-one In a similar procedure as shown in Example 1, the title compound was prepared in 4% yield from 2-chloro-5-methylpyrimidine. ¹H NMR (400 MHz, DMSO-d₆): δ 11.38 (br. s, 1H), 9.09 (s, 1H), 8.74 (s, 2H), 8.23-8.20 (m, 2H), 3.06-3.03 (m, 1H), 2.46 (s, 3H), 2.33 (s, 3H), 1.31 (d, J=6.8 Hz, 6H). LCMS (Method C): RT=0.760 min, m/z: 349.9 [M+H⁺].

Example 25

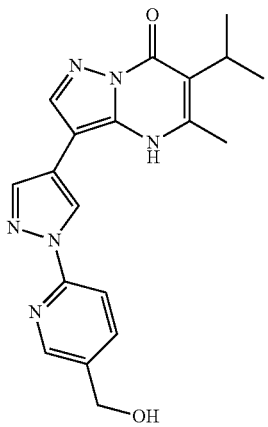 [SMILES: Cc1[nH]c2c(-c3cnn(-c4ccc(CO)cn4)c3)cnn2c(=O)c1C(C)C]

3-(1-(5-(hydroxymethyl)pyridin-2-yl)-1H-pyrazol-4-yl)-6-isopropyl-5-methylpyrazolo[1,5-a]pyrimidin-7(4H)-one In a similar procedure as shown in Example 12, the title compound was prepared in 29% yield from 6-fluoronicotinic acid (2 steps). ¹H NMR (400 MHz, DMSO-d₆): δ 11.37 (br. s, 1H), 9.08 (s, 1H), 8.44 (s, 1H), 8.18 (d, J=8.0 Hz, 2H), 7.94-7.93 (m, 2H), 5.40 (br. s, 1H), 4.58 (s, 2H), 3.09-3.00 (m, 1H), 2.45 (s, 3H), 1.32 (d, J=6.8 Hz, 6H). LCMS (Method C): RT=0.760 min, m/z: 364.9 [M+H⁺].

Example 26

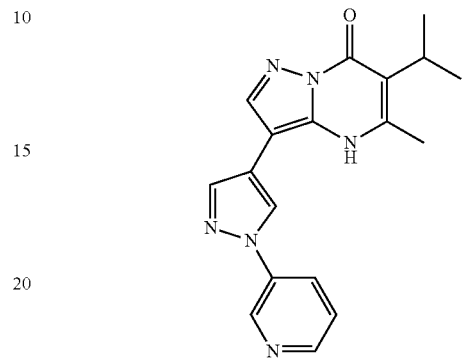

6-isopropyl-5-methyl-3-(1-(pyridin-3-yl)-1H-pyrazol-4-yl)pyrazolo[1,5-a]pyrimidin-7(4H)-one A mixture of 6-isopropyl-5-methyl-3-(1H-pyrazol-4-yl)pyrazolo[1,5-a]pyrimidin-7(4H)-one (257 mg, 1.00 mmol), 3-bromopyridine (316 mg, 2.00 mmol), CuI (10 mg, 0.05 mmol), L-proline (12 mg, 0.10 mmol) and K₂CO₃ (138 mg, 1.00 mmol) in DMSO (5 mL) was heated at 120° C. for 12 h under nitrogen atmosphere. After cooling, the mixture was filtered and the filtrate was evaporated. The residue was purified by preparative HPLC to give the title compound (130 mg, 37% yield) as a white solid. ¹H NMR (400 MHz, DMSO-d₆): δ 11.40 (br. s, 1H), 9.15 (s, 1H), 8.90 (s, 1H), 8.54 (d, J=4.0 Hz, 1H), 8.26-8.24 (m, 1H), 8.17 (s, 1H), 8.07 (s, 1H), 7.61-7.58 (m, 1H), 3.08-3.01 (m, 1H), 2.45 (s, 3H), 1.32 (d, J=6.8 Hz, 6H). LCMS (Method C): RT=0.723 min, m/z: 334.9 [M+H⁺].

Example 27

Step 1

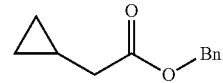 [SMILES: O=C(CC1CC1)OCc1ccccc1]

Benzyl 2-cyclopropylacetate

K₂CO₃ (110.4 g, 0.80 mol) was added portionwise to a stirred solution of 2-cyclopropylacetic acid (40.0 g, 0.40 mol) in DMF (200 mL), followed by BnBr (75.2 g, 0.44 mol). After addition, the resulting mixture was stirred at room temperature for 16 h. The solvent was evaporated under reduced pressure, and the residue was diluted with EtOAc (1000 mL). This solution was then washed with HCl (aq. 1 N, 100 mL×3), dried and evaporated to give the crude title compound (65.0 g, 86% yield) as a colorless oil. This crude was used into next step without further purification.

Step 2

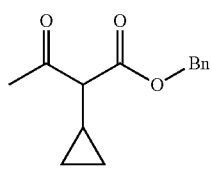

Benzyl 2-cyclopropyl-3-oxobutanoate

LiHMDS (1 M in THF, 410.5 mL, 410.5 mmol) was added dropwise to a stirred and cooled (−78° C.) solution of benzyl 2-cyclopropylacetate (65.0 g, 342.1 mmol) in THF (600 mL). Stirring at −78° C. continued for 20 min before acetyl chloride (410.5 mmol) was added dropwise. The resulting mixture was stirred at −78° C. for additional 2 h, at which time TLC (PE/EtOAc=10:1) showed complete conversion. The mixture was quenched by addition of saturated aqueous NH$_4$Cl (200 mL), and then extracted with EtOAc (300 mL×3). The combined organic layers were dried and evaporated. The residue was purified by flash chromatography (PE/EtOAc=100:1) to give the title compound (30.0 g, 38% yield) as a colorless oil. $^1$H NMR (400 MHz, CDCl$_3$): δ 7.32-7.17 (m, 5H), 5.12 (s, 2H), 2.60 (d, J=10.4 Hz, 1H), 2.18 (s, 3H), 1.30-1.22 (m, 1H), 0.66-0.57 (m, 2H), 0.28-0.18 (m, 2H).

Step 3

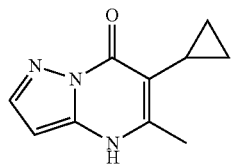

6-cyclopropyl-5-methylpyrazolo[1,5-a]pyrimidin-7 (4H)-one

A mixture of 1H-pyrazol-5-amine (11.3 g, 136.0 mmol) and benzyl 2-cyclopropyl-3-oxobutanoate (30.0 g, 129.3 mmol) in AcOH (80 mL) was heated at 130° C. for 2 h. After evaporation of the solvent, the residue was washed with a mixture of PE and EtOAc (200 mL, 10:1) to give the crude title compound (24.0 g, 98% yield) as a gray solid. This crude was used in the next step without further purification.

Step 4

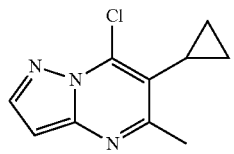

7-chloro-6-cyclopropyl-5-methylpyrazolo[1,5-a] pyrimidine

A suspension of 6-cyclopropyl-5-methylpyrazolo[1,5-a] pyrimidin-7(4H)-one (20.5 g, 106 mmol) in POCl$_3$ (110.0 g, 720 mmol) was heated at 130° C. for 2 h. After completion of reaction, excess POCl$_3$ was removed under reduced pressure, and the residue was poured into ice-water. The solution was adjusted to pH=9 by adding aqueous Na$_2$CO$_3$ and then extracted with EtOAc (200 mL×3). The combined organic layers were dried (Na$_2$SO$_4$) and evaporated. The residue was purified by flash chromatography (PE/EtOAc=50:1-20:1) over silica gel to give the title compound (10.0 g, 44% yield) as a yellow oil.

Step 5

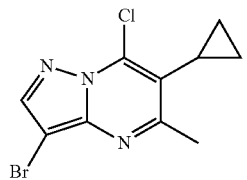

3-bromo-7-chloro-6-cyclopropyl-5-methylpyrazolo [1,5-a]pyrimidine

NBS (8.9 g, 50.0 mmol) in CH$_3$CN (50 mL) was added in portions to a stirred solution of 7-chloro-6-cyclopropyl-5-methylpyrazolo[1,5-a]pyrimidine (10.0 g, 48.3 mmol) in DCM (80 mL) over a period of 30 min at room temperature. After addition, the mixture was stirred for another 1 h at room temperature, at which time TLC showed the complete conversion. The solvent was evaporated; the residue was purified by silica gel chromatography eluted with PE/EtOAc (50:1-20:1) to give the title compound (12.5 g, 91% yield) as a yellow oil. $^1$H NMR (400 MHz, CDCl$_3$): δ 8.08 (s, 1H), 2.78 (s, 3H), 1.83 (m, 1H), 1.26-1.19 (m, 2H), 0.80-0.79 (m, 2H).

Step 6

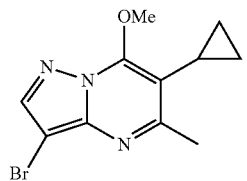 [SMILES: COc1c(C2CC2)c(C)nc2c(Br)cnn12]

3-bromo-6-cyclopropyl-7-methoxy-5-methylpyrazolo[1,5-a]pyrimidine

NaOMe (7.6 g, 141.0 mmol) was added portionwise to a stirred solution of 3-bromo-7-chloro-6-cyclopropyl-5-methylpyrazolo[1,5-a]pyrimidine (10.0 g, 35.0 mmol) in methanol (80 mL). After addition, the reaction mixture was stirred at room temperature for 4 h, at which time LCMS showed completion of reaction. The solvent was evaporated under reduced pressure, and the residue was diluted with water (100 mL). The resulting mixture was extracted with EtOAc (80 mL×3). The combined organic layers were dried and concentrated to give the title compound (10.0 g, 100% yield) as an yellow oil. ¹H NMR (400 MHz, CDCl₃): δ 7.98 (s, 1H), 4.33 (s, 3H), 2.72 (s, 3H), 1.72-1.66 (m, 1H), 1.16-1.06 (m, 2H), 0.78-0.69 (m, 2H).

Step 7

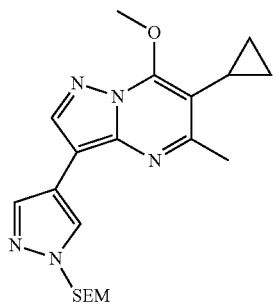 [SMILES: COc1c(C2CC2)c(C)nc2c(-c3cnn(COCC[Si](C)(C)C)c3)cnn12]

6-cyclopropyl-7-methoxy-5-methyl-3-(1-((2-(trimethylsilyl)ethoxy)methyl)-1H-pyrazol-4-yl)pyrazolo[1,5-a]pyrimidine A mixture of 3-bromo-6-cyclopropyl-7-methoxy-5-methylpyrazolo[1,5-a]pyrimidine (6.6 g, 23.4 mmol), 4-(4,4,5,5-tetramethyl-1,3,2-dioxaborolan-2-yl)-1-((2-(trimethylsilyl)ethoxy)methyl)-1H-pyrazole (11.4 g, 35.2 mmol), Pd(PPh₃)₂Cl₂ (1.6 g, 2.4 mmol) and Na₂CO₃ (5.0 g, 46.8 mmol) in dioxane/H₂O (125 mL/25 mL) was heated at 120° C. for 16 h under nitrogen protection. After cooling, the mixture was filtered through a short pad of Celite and then extracted with EtOAC (100 mL×3). The combined organic layers were dried and evaporated. The residue was purified by flash column (PE/EtOAc=10:1-3:1) over silica gel to give the title compound (3.8 g, 41% yield) as an yellow oil. ¹H NMR (400 MHz, CDCl₃): δ 8.19 (s, 1H), 8.17 (s, 1H), 7.99 (s, 1H), 5.49 (s, 2H), 4.36 (s, 3H), 3.66-3.58 (m, 2H), 2.74 (s, 3H), 1.75-1.68 (m, 1H), 1.15-1.09 (m, 2H), 0.98-0.91 (m, 2H), 0.79-0.73 (m, 2H), −0.01-−0.02 (s, 9H).

Step 8

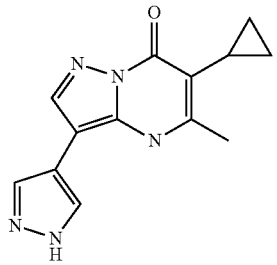 [SMILES: Cc1[nH]c2c(-c3cn[nH]c3)cnn2c(=O)c1C1CC1]

6-cyclopropyl-5-methyl-3-(1H-pyrazol-4-yl)pyrazolo[1,5-a]pyrimidin-7(4H)-one

A mixture of 6-cyclopropyl-7-methoxy-5-methyl-3-(1-((2-(trimethylsilyl)ethoxy)methyl)-1H-pyrazol-4-yl)pyrazolo[1,5-a]pyrimidine (2.8 g, 7.0 mmol) in MeOH (40 mL) and HCl (6 N, 6 mL, 36.0 mmol) was heated at reflux for 2 h. The solvent was removed under reduced pressure, and the residue was diluted by addition of saturated aqueous Na₂CO₃. The resulting mixture was extracted with CH₂Cl₂ (80 mL×3). The combined organic layers were dried and evaporated. The residue was purified by flash column (DCM/MeOH=9:1) to give the title compound (1.3 g, 73% yield) as a yellow solid. LCMS (ESI) m/z: 256.0 [M+H⁺].

Step 9

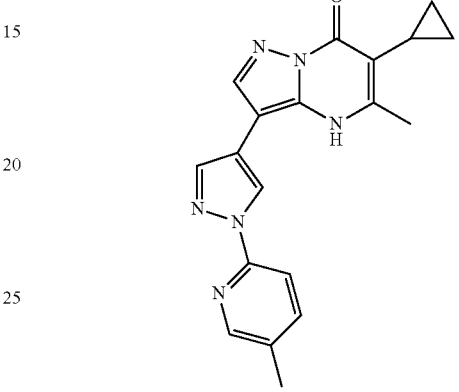

6-cyclopropyl-5-methyl-3-(1-(5-methylpyridin-2-yl)-1H-pyrazol-4-yl)pyrazolo[1,5-a]pyrimidin-7(4H)-one In a similar procedure as shown in Example 26, the title compound was prepared in 23% yield from 2-bromo-5-methylpyridine. ¹H NMR (400 MHz, DMSO-d₆): δ 9.05 (s, 1H), 8.34 (s, 1H), 8.18-8.16 (m, 2H), 7.86-7.82 (m, 2H), 2.53 (s, 3H), 2.35 (s, 3H), 1.55-1.45 (m, 1H), 0.90-0.86 (m, 2H), 0.68-0.58 (m, 2H). LCMS (Method C): RT=0.803 min, m/z: 345.8 [M+H⁺].

Example 28

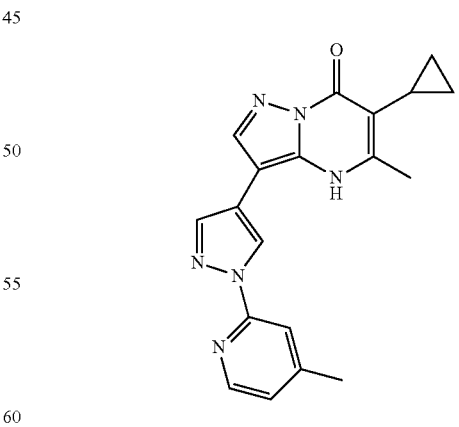

6-cyclopropyl-5-methyl-3-(1-(4-methylpyridin-2-yl)-1H-pyrazol-4-yl)pyrazolo[1,5-a]pyrimidin-7(6H)-one In a similar procedure as shown in Example 26, the title compound was prepared in 13% yield from 2-bromo-4- methylpyridine. ¹H NMR (400 MHz, DMSO-d₆): δ 11.56 (br. s, 1H), 9.07 (br. s., 1H), 8.36 (d, J=4.0 Hz, 1H), 8.19 (d, J=0.4 Hz, 2H), 7.82 (s, 1H), 7.20 (d, J=4.8 Hz, 1H), 2.52 (s, 3H), 2.43 (s, 3H), 1.50-1.48 (m, 1H), 0.88-0.86 (m, 2H), 0.65-0.63 (m, 2H). LCMS (Method C): RT=0.797 min, m/z: 346.9 [M+H⁺].

Example 29

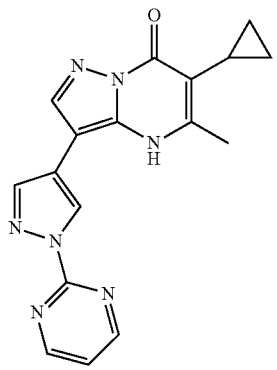 [SMILES: Cc1[nH]c2c(-c3cnn(-c4ncccn4)c3)cnn2c(=O)c1C1CC1]

6-cyclopropyl-5-methyl-3-(1-(pyrimidin-2-yl)-1H-pyrazol-4-yl)pyrazolo[1,5-a]pyrimidin-7(6H)-one In a similar procedure as shown in Example 1, the title compound was prepared in 34% yield from 2-chloropyrimidine. ¹H NMR (400 MHz, DMSO-d₆): δ 11.53 (br. s, 1H), 9.13 (s, 1H), 8.89 (d, J=4.8 Hz, 1H), 8.27 (s, 1H), 8.20 (s, 1H), 7.50 (t, J=4.8 Hz, 1H), 2.53 (s, 3H), 1.52-1.47 (m, 1H), 0.90-0.85 (m, 2H), 0.66-0.64 (m, 2H). LCMS (Method C): RT=0.724 min, m/z: 339.9 [M+H⁺].

Example 30

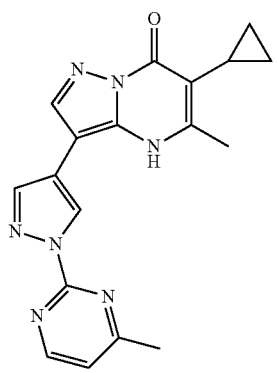 [SMILES: Cc1ccnc(-n2cc(-c3cnn4c(=O)c(C5CC5)c(C)[nH]c34)cn2)n1]

6-cyclopropyl-5-methyl-3-(1-(4-methylpyrimidin-2-yl)-1H-pyrazol-4-yl)pyrazolo[1,5-a]pyrimidin-7(6H)-one In a similar procedure as shown in Example 1, the title compound was prepared in 29% yield from 2-chloro-4-methylpyrimidine. ¹H NMR (400 MHz, DMSO-d₆): δ 9.05 (s, 1H), 8.71 (d, J=5.0 Hz, 1H), 8.25 (d, J=0.8 Hz, 1H), 8.16 (s, 1H), 7.35 (d, J=4.8 Hz, 1H), 2.56 (s, 3H), 2.49 (s, 3H), 1.53-1.46 (m, 1H), 0.88-0.83 (m, 2H), 0.66-0.65 (m, 2H). LCMS (Method C): RT=0.738 min, m/z: 347.9 [M+H⁺].

Example 31

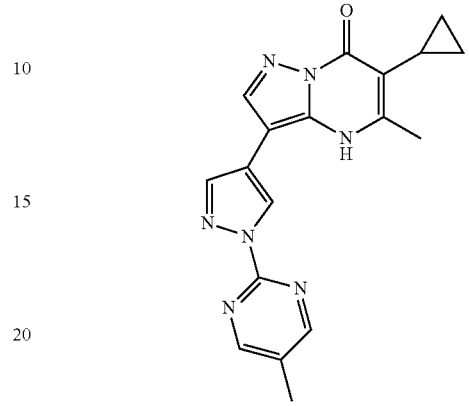

6-cyclopropyl-5-methyl-3-(1-(5-methylpyrimidin-2-yl)-1H-pyrazol-4-yl)pyrazolo[1,5-a]pyrimidin-7(6H)-one In a similar procedure as shown in Example 1, the title compound was prepared in 26% yield from 2-chloro-5-methylpyrimidine. ¹H NMR (400 MHz, DMSO-d₆): δ 11.52 (br. s, 1H), 9.10 (s, 1H), 8.74 (s, 2H), 8.23 (s, 1H), 8.19 (s, 1H), 2.53 (s, 3H), 2.33 (s, 3H), 1.52-1.47 (m, 1H), 0.90-0.85 (m, 2H), 0.66-0.64 (m, 2H). LCMS (Method C): RT=0.743 min, m/z: 347.9 [M+H⁺].

Example 32

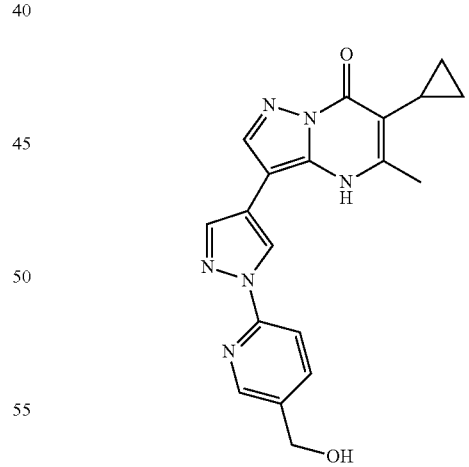

6-cyclopropyl-3-(1-(5-(hydroxymethyl)pyridin-2-yl)-1H-pyrazol-4-yl)-5-methylpyrazolo[1,5-a]pyrimidin-7(6H)-one In a similar procedure as shown in Example 11, the title compound was prepared in 11% yield from 6-fluoronicotinic acid (2 steps). ¹H NMR (400 MHz, DMSO-d₆): δ 11.51 (br. s, 1H), 9.08-9.05 (m, 1H), 8.41 (s, 1H), 8.16-8.13 (m, 2H), 7.91-7.90 (m, 2H), 5.38-5.35 (m, 1H), 4.55 (d, J=5.6 Hz, 2H), 2.50 (s, 3H), 1.48-1.46 (m, 1H), 0.88-0.82 (m, 2H), 0.62-0.59 (m, 2H). LCMS (Method C): RT=0.724 min, m/z: 362.9 [M+H⁺].

Example 33

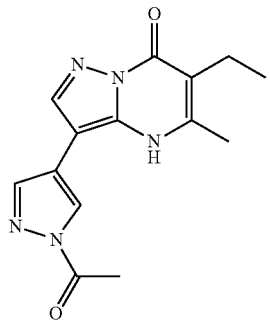 [SMILES: CCc1c(C)[nH]c2c(-c3cnn(C(C)=O)c3)cnn2c1=O]

3-(1-acetyl-1H-pyrazol-4-yl)-6-ethyl-5-methylpyrazolo[1,5-a]pyrimidin-7(4H)-one

Ac₂O (102 mg, 1.0 mmol) was added to a stirred and cooled (0° C.) solution of 6-ethyl-5-methyl-3-(1H-pyrazol-4-yl)pyrazolo[1,5-a]pyrimidin-7(4H)-one (120 mg, 0.49 mmol) in pyridine (5 ml). After addition, the mixture was stirred at 0° C. for 1 h then concentrated. The residue was purified by preparative HPLC to give the title compound (30 mg, 21% yield) as a yellow solid. ¹H NMR (400 MHz, DMSO-d₆): δ 11.40 (s, 1H), 8.95 (d, J=0.4 Hz, 1H), 8.32 (s, 1H), 8.24 (s, 1H), 2.69 (s, 3H), 2.51 (q, J=1.6 Hz, 2H), 2.44 (s, 3H), 1.05 (t, J=7.2 Hz, 3H). LCMS (Method C): RT=0.703 min, m/z: 285.8 [M+H⁺].

Example 34

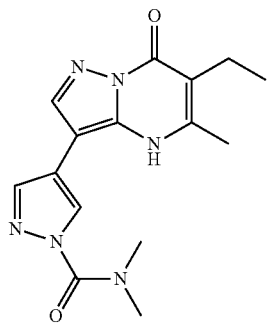 [SMILES: CCc1c(C)[nH]c2c(-c3cnn(C(=O)N(C)C)c3)cnn2c1=O]

4-(6-ethyl-5-methyl-7-oxo-4,7-dihydropyrazolo[1,5-a]pyrimidin-3-yl)-N,N-dimethyl-1H-pyrazole-1-carboxamide In a similar procedure as shown in Example 33, the title compound was prepared in 84% yield from dimethylcarbamic chloride. ¹H NMR (400 MHz, DMSO-d₆): δ 11.44 (s, 1H), 8.69 (s, 1H), 814 (s, 2H), 3.13 (s, 6H), 2.47-2.50 (m, 2H), 2.40 (s, 3H), 1.01 (t, J=7.2 Hz, 3H). LCMS (Method C): RT=0.700 min, m/z: 314.9 [M+H⁺].

Example 35

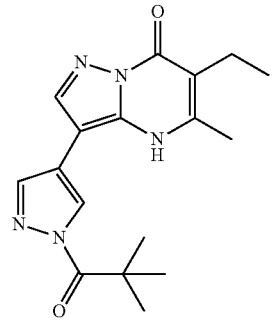 [SMILES: CCc1c(C)[nH]c2c(-c3cnn(C(=O)C(C)(C)C)c3)cnn2c1=O]

6-ethyl-5-methyl-3-(1-pivaloyl-1H-pyrazol-4-yl)pyrazolo[1,5-a]pyrimidin-7(4H)-one In a similar procedure as shown in Example 33, the title compound was prepared in 23.9% yield from pivaloyl chloride. ¹H NMR (400 MHz, DMSO-d₆): δ 11.45 (s, 1H), 8.85 (d, J=0.4 Hz, 1H), 8.28 (s, 1H), 8.20 (s, 1H), 2.50 (q, J=1.6 Hz, 2H), 2.43 (s, 3H), 1.49 (s, 9H), 1.05 (t, J=7.2 Hz, 3H). LCMS (Method C): RT=0.848 min, m/z: 327.9 [M+H⁺].

Example 36

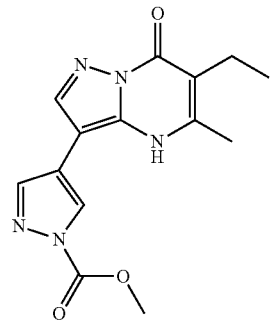 [SMILES: CCc1c(C)[nH]c2c(-c3cnn(C(=O)OC)c3)cnn2c1=O]

Methyl 4-(6-ethyl-5-methyl-7-oxo-4,7-dihydropyrazolo[1,5-a]pyrimidin-3-yl)-1H-pyrazole-1-carboxylate In a similar procedure as shown in Example 33, the title compound was prepared in 4.1% yield from methyl chloroformate. ¹H NMR (400 MHz, DMSO-d₆): δ 11.40 (s, 1H), 8.86 (s, 1H), 8.30 (s, 1H), 8.22 (s, 1H), 4.03 (s, 3H), 2.50 (q, J=1.6 Hz, 2H), 2.44 (s, 3H), 1.05 (t, J=7.6 Hz, 3H). LCMS (Method C): RT=0.687 min, m/z: 301.8 [M+H⁺].

Method B

Example 37

Step 1

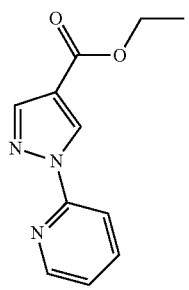

Ethyl 1-(pyridin-2-yl)-1H-pyrazole-4-carboxylate

A solution of ethyl 1H-pyrazole-4-carboxylate (1.2 g, 8.6 mmol) in DMF (5 mL) was added dropwise to a stirred and cooled (0° C.) suspension of NaH (60%, 410 mg, 10.3 mmol) in DMF (5 mL). Stirring continued for 30 min at 0° C. before 2-fluoropyridine (915 mg, 9.4 mmol) was added. After addition, the ice batch was removed and the reaction mixture was heated at 80° C. for 3 h. After being cooled, the mixture was quenched by addition of saturated aqueous NH₄Cl and then extracted with EtOAc (40 mL×3). The combined organic layers were dried and evaporated. The residue was purified by silica gel flash chromatography (PE/EtOAc=5:1) to give the title compound (1.2 g, 65% yield) as a yellow oil.

Step 2

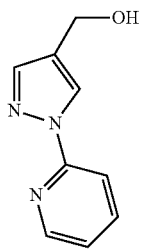 [SMILES: OCc1cnn(-c2ccccn2)c1]

(1-(pyridin-2-yl)-1H-pyrazol-4-yl)methanol

DIBAL-H (1 M in THF, 11.0 mL, 11.0 mmol) was added dropwise to a stirred and cooled (0° C.) solution of ethyl 1-(pyridin-2-yl)-1H-pyrazole-4-carboxylate (1.2 g, 5.5 mmol) in THF (20 mL). After addition, stirring at 0° C. continued for 3 h before the reaction mixture was quenched by addition of 1 M NH₄Cl (20 mL). The mixture was then extracted with EtOAc (40 mL×3). The combined organic layers were dried and evaporated to afford the crude title compound (0.9 g, 93% yield) as a colorless oil. This crude was used in the next step without further purification.

Step 3

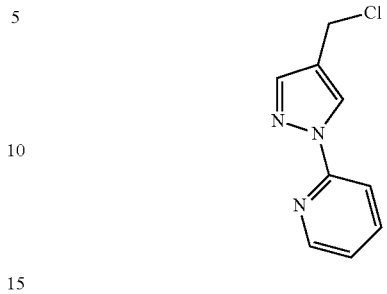

2-(4-(chloromethyl)-1H-pyrazol-1-yl)pyridine

To a solution of (1-(pyridin-2-yl)-1H-pyrazol-4-yl)methanol (0.9 g, 5.1 mmol) in DCM (10 mL) was added sulfurous dichloride (1.84 g, 15.3 mmol) at room temperature. After addition, the reaction mixture was stirred for 2 h and then concentrated. The residue was diluted with EtOAc (30 mL) and adjusted to pH=9 by addition of 1 M aqueous K₂CO₃. The organic layer was separated and the aqueous layer was extracted with EtOAc (30 mL×3). The combined organic layers were dried and evaporated. The residue was purified by flash chromatography (PE/EtOAc=5:1) to give the title compound (0.9 g, 90% yield) as yellow oil.

Step 4

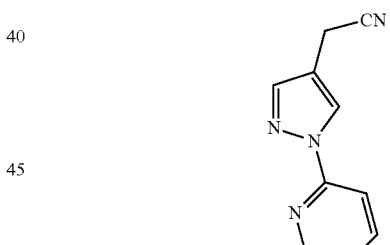

2-(1-(pyridin-2-yl)-1H-pyrazol-4-yl)acetonitrile

KCN (1.0 g, 15.4 mmol) was added in portions to a stirred solution of 2-(4-(chloromethyl)-1H-pyrazol-1-yl)pyridine (0.9 g, 4.6 mmol) in DMSO/H₂O (10 mL/3 mL). The resulting mixture was heated at 50° C. for 5 h, at which time TLC showed complete conversion. The reaction mixture was cooled and diluted with EtOAc (50 mL). The organic layer was separated and the aqueous layer was extracted with EtOAc (30 mL×3). The combined organic layers were dried, concentrated to afford the crude title compound (0.8 g, 93% yield) as yellow oil. It was used in the next step without further purification.

Step 5

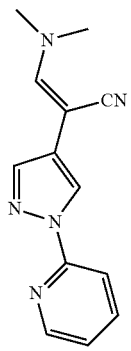 [SMILES: CN(C)/C=C(\C#N)c1cnn(-c2ccccn2)c1]

3-(dimethylamino)-2-(1-(pyridin-2-yl)-1H-pyrazol-4-yl)acrylonitrile

A mixture of 2-(1-(pyridin-2-yl)-1H-pyrazol-4-yl)acetonitrile (0.8 g, 4.3 mmol) in DMF-DMA (2.0 mL) was heated at 140° C. for 30 min under microwave irradiation. The mixture was concentrated to afford the crude title compound, which was used in the next step without further purification.

Step 6

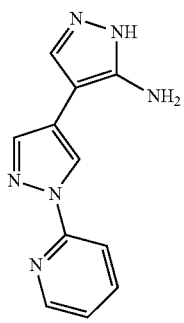 [SMILES: Nc1[nH]ncc1-c1cnn(-c2ccccn2)c1]

1'-(pyridin-2-yl)-1H,1'H-[4,4'-bipyrazol]-5-amine

Concentrated HCl (15 mL) was added slowly to a stirred solution of hydrazine monohydrate (2.0 mL) in EtOH (20 mL), followed by 3-(dimethylamino)-2-(1-(pyridin-2-yl)-1H-pyrazol-4-yl) and acrylonitrile (11.1 g, 4.6 mmol). The resultant yellow solution was heated at reflux for 2 h. After cooling, the mixture was adjusted to pH=9 by addition of 1 M aqueous $K_2CO_3$. The resulting mixture was then extracted with EtOAc (40 mL×3). The combined organic layers were dried and evaporated. The residue was purified by silica gel chromatography (DCM/MeOH=10:1) to give the title compound (1.0 g, 96% yield) as a yellow oil. LCMS (Method C): RT=0.427 min, m/z: 226.8 [M+H$^+$].

Step 7

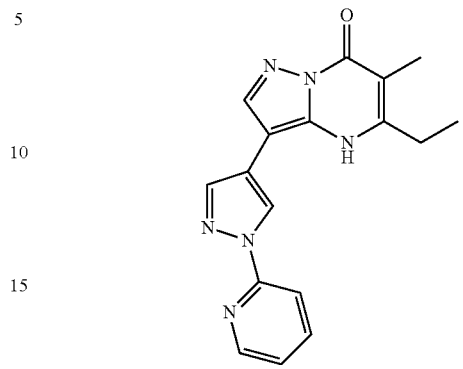

5-ethyl-6-methyl-3-(1-(pyridin-2-yl)-1H-pyrazol-4-yl)pyrazolo[1,5-a]pyrimidin-7(4H)-one A mixture of 1'-(pyridin-2-yl)-1H,1'H-[4,4'-bipyrazol]-5-amine (150 mg, 0.66 mmol) and ethyl 2-methyl-3-oxopentanoate (209 mg, 1.32 mmol) in AcOH (10 mL) was heated at 160° C. for 1 h. After evaporation of the solvent, the crude product was purified by preparative HPLC to give the title compound (10.6 mg, 5% yield) as a white solid. $^1$H NMR (400 MHz, DMSO-d$_6$): δ 11.49 (br. s, 1H), 9.10 (s, 1H), 8.51 (d, J=4.8 Hz, 1H), 8.22-8.19 (m, 2H), 8.01-7.96 (m, 2H), 7.37 (t, J=5.6 Hz, 1H), 2.75 (q, J=7.6 Hz, 2H), 2.03 (s, 1H), 1.22 (t, J=7.2 Hz, 3H). LCMS (Method C): RT=0.754 min, m/z: 320.8 [M+H$^+$].

Example 38

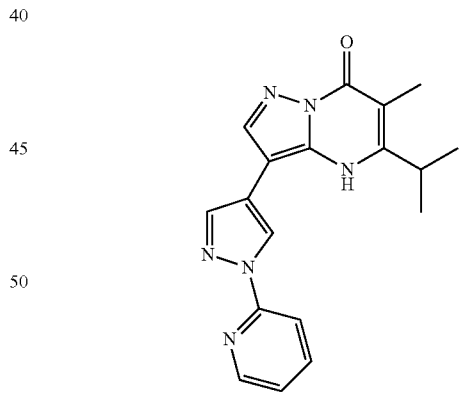

5-isopropyl-6-methyl-3-(1-(pyridin-2-yl)-1H-pyrazol-4-yl)pyrazolo[1,5-a]pyrimidin-7(4H)-one In a similar procedure as shown in Example 37, the title compound was prepared in 7% yield from ethyl 2,4-dimethyl-3-oxopentanoate. $^1$H NMR (400 MHz, DMSO-d$_6$): δ 10.90 (br. s, 1H), 8.97 (s, 1H), 8.50 (d, J=4.4 Hz, 1H), 8.16-7.90 (m, 4H), 7.35 (s, 1H), 2.46-2.44 (m, 1H), 2.07 (s, 3H), 1.40-1.20 (m, 6H). LCMS (Method C): RT=0.782 min, m/z: 334.9 [M+H$^+$].

Example 39

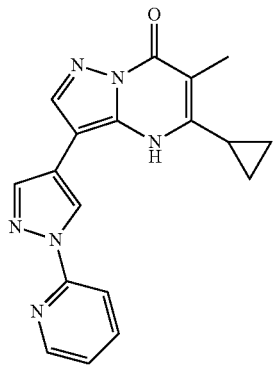 [SMILES: Cc1c(C2CC2)[nH]c2c(-c3cnn(-c4ccccn4)c3)cnn2c1=O]

5-cyclopropyl-6-methyl-3-(1-(pyridin-2-yl)-1H-pyrazol-4-yl)pyrazolo[1,5-a]pyrimidin-7(4H)-one In a similar procedure as shown in Example 37, the title compound was prepared in 4% yield from ethyl 3-cyclopropyl-2-methyl-3-oxopropanoate. $^1$H NMR (400 MHz, DMSO-$d_6$): δ 11.16 (br. s, 1H), 9.01 (s, 1H), 8.51 (d, J=4.4 Hz, 1H), 8.18-8.15 (m, 2H), 8.02-7.95 (m, 2H), 7.36 (s, 1H), 2.19-2.14 (m, 4H), 1.04-0.99 (m, 4H). LCMS (Method C): RT=0.761 min, m/z: 332.9 [M+H$^+$].

Example 40

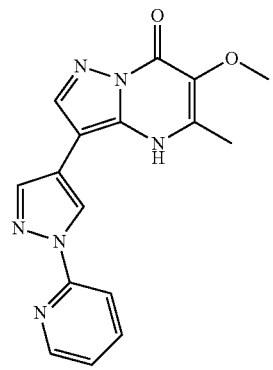 [SMILES: COc1c(C)[nH]c2c(-c3cnn(-c4ccccn4)c3)cnn2c1=O]

6-methoxy-5-methyl-3-(1-(pyridin-2-yl)-1H-pyrazol-4-yl)pyrazolo[1,5-a]pyrimidin-7(4H)-one In a similar procedure as shown in Example 37, the title compound was prepared in 12% yield from ethyl 2-methoxy-3-oxobutanoate. $^1$H NMR (400 MHz, DMSO-$d_6$): δ 11.58 (br. s, 1H), 9.10 (d, J=0.8 Hz, 1H), 8.48-8.45 (m, 1H), 8.23-8.20 (m, 2H), 8.00-7.94 (m, 2H), 7.37-7.34 (m, 1H), 3.71 (s, 3H), 2.39 (s, 3H). LCMS (Method C): RT=0.717 min, m/z: 322.8 [M+H$^+$].

Example 41

Step 1

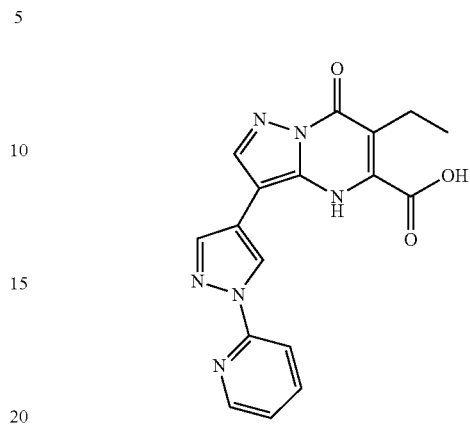

6-ethyl-7-oxo-3-(1-(pyridin-2-yl)-1H-pyrazol-4-yl)-4,7-dihydropyrazolo[1,5-a]pyrimidine-5-carboxylic acid A mixture of F-(pyridin-2-yl)-1H,1'H-[4,4'-bipyrazol]-5-amine (300 mg, 1.33 mmol), TsOH (228 mg, 1.33 mmol) and dimethyl 2-ethyl-3-oxosuccinate (299 mg, 1.59 mmol) in butan-1-ol (10 mL) was heated at reflux for 2 h. The solid was collected by filtration to give the crude title compound (200 mg, 43% yield), which was used in the next step without purification.

Step 2

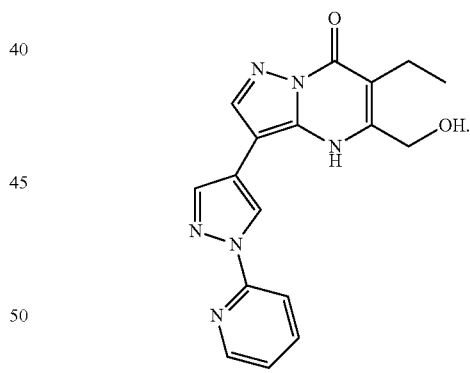

6-ethyl-5-(hydroxymethyl)-3-(1-(pyridin-2-yl)-1H-pyrazol-4-yl)pyrazolo[1,5-a]pyrimidin-7(4H)-one Broane (1 M in THF, 5.4 mL, 5.4 mmol) was added dropwise to a stirred suspension of 6-ethyl-7-oxo-3-(1-(pyridin-2-yl)-1H-pyrazol-4-yl)-4,7-dihydropyrazolo[1,5-a]pyrimidine-5-carboxylic acid (105 mg, 0.3 mmol) in THF (10 mL). The resulting mixture was heated at reflux for 16 h and then quenched by addition of MeOH (1 mL). The solvent was evaporated and the residue was purified by preparative HPLC to give the title compound (8.2 mg, 9% yield) as a white solid. $^1$H NMR (400 MHz, DMSO-$d_6$): δ 11.35 (br. s, 1H), 9.11 (s, 1H), 8.51 (d, J=4.4 Hz, 1H), 8.25-8.22 (m, 2H), 8.04-7.97 (m, 2H), 7.38 (t, J=5.2 Hz, 1H), 5.68 (br. s, 1H), 4.59 (s, 2H), 2.54 (q, J=7.2 Hz, 2H), 1.08 (t, J=7.2 Hz, 3H). LCMS (Method A): RT=1.121 min, m/z: 337.1 [M+H$^+$].

Example 42

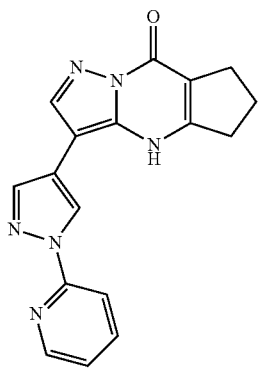 [SMILES: O=c1c2c([nH]c3c(-c4cnn(-c5ccccn5)c4)cnn13)CCC2]

3-(1-(pyridin-2-yl)-1H-pyrazol-4-yl)-6,7-dihydro-4H-cyclopenta[d]pyrazolo[1,5-a]pyrimidin-8(5H)-one The mixture of 4-[1-(2-pyridyl)pyrazol-4-yl]-1H-pyrazol-5-amine (50 mg, 0.221 mmol) and ethyl 2-oxocyclopentanecarboxylate (41 mg, 0.265 mmol) in acetic acid (2 mL) was heated at 120° C. for 2 h. The reaction mixture was then cooled to room temperature. The precipitate was collected by filtration, washed with EtOH, then EtOAc, and dried to give the title compound (38 mg, 54% yield) as an off-white solid. $^1$H NMR (400 MHz, DMSO-d6) δ 12.14 (s, 1H), 9.12 (d, J=1.0 Hz, 1H), 8.52 (ddd, J=4.9, 1.8, 0.9 Hz, 1H), 8.31-8.19 (m, 2H), 8.09-7.90 (m, 2H), 7.44-7.32 (m, 1H), 3.10-2.95 (m, 2H), 2.72 (t, J=7.3 Hz, 2H), 2.12 (p, J=7.7 Hz, 2H). LCMS (ESI) (Method D): RT=4.47 min, m/z 319.1 [M+H$^+$].

Example 43

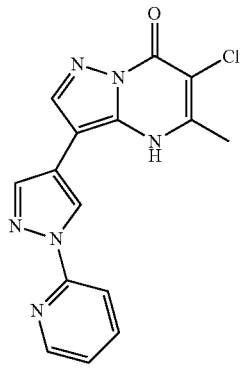 [SMILES: Cc1[nH]c2c(-c3cnn(-c4ccccn4)c3)cnn2c(=O)c1Cl]

6-chloro-5-methyl-3-[1-(2-pyridyl)pyrazol-4-yl]-4H-pyrazolo[1,5-a]pyrimidin-7-one In a similar procedure as shown in Example 42, this compound was prepared in 66% yield. $^1$H NMR (400 MHz, DMSO-d$_6$) δ 12.18 (s, 1H), 9.12 (d, J=0.9 Hz, 1H), 8.52 (ddd, J=4.8, 1.8, 0.9 Hz, 1H), 8.30 (s, 1H), 8.22 (d, J=0.8 Hz, 1H), 8.08-7.94 (m, 2H), 7.43-7.33 (m, 1H), 2.56 (s, 3H). LCMS (Method A): RT=4.38 min, m/z: 327 [M+H$^+$].

Example 44

Step 1

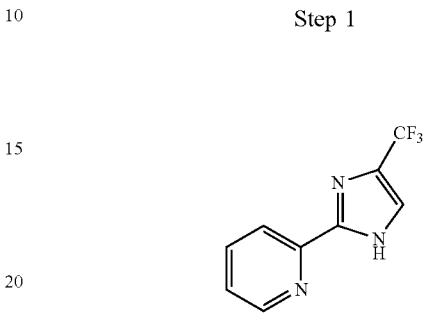

2-(4-(trifluoromethyl)-1H-imidazol-2-yl)pyridine 3,3-dibromo-1,1,1-trifluoropropan-2-one (59.0 g, 0.22 mol) was added in portions to a stirred solution of sodium acetate (36.8 g, 0.44 mol) in water (100 mL). The resulting mixture was heated at 100° C. for 30 min and cooled to room temperature, then a solution of picolinaldehyde (20.0 g. 0.20 mol) in ammonium hydroxide (35%, 200 mL) and MeOH (600 mL) was added dropwise. Stirring at room temperature continued for 12 h and the mixture was concentrated. The solid was collected by filtration and washed with water to give the crude title compound (23.0 g, 55%) as brown solid. It was used directly in next step without further purification. LCMS (Method C): RT=0.605 min, m/z: 213.7 [M+H$^+$].

Step 2

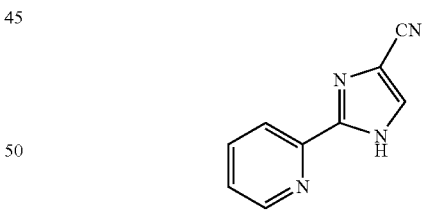

2-(pyridin-2-yl)-1H-imidazole-4-carbonitrile

A solution of 2-(4-(trifluoromethyl)-1H-imidazol-2-yl)pyridine (21.0 g, 100 mmol) in MeOH (800 mL) and NH$_4$OH (5%, 1000 mL) was heated to 60° C. for 10 h. The solvent was evaporated. The solid was collected, washed with water and dried to give the crude title compound (8.7 g, 51% yield) as brown solid. It was used directly for next step without further purification. LCMS (Method C): RT=0.390 min, m/z: 170.7 [M+H$^+$].

Step 3

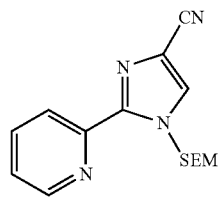 [SMILES: C[Si](C)(C)CCOCn1cc(C#N)nc1-c1ccccn1]

2-(pyridin-2-yl)-1-(2-(trimethylsilyl)ethoxy)methyl)-1H-imidazole-4-carbonitrile A solution of 2-(pyridin-2-yl)-1H-imidazole-4-carbonitrile (6.8 g, 40 mmol) in DMF (50 mL) was added dropwise to a stirred and cooled (0° C.) suspension of NaH (60%, 3.2 g, 80 mmol) in DMF (50 mL) Stirring continued for 30 min, then SEMCl (10.0 g, 60 mmol) was added. The reaction mixture was stirred at room temperature for 5 h, and quenched by addition of saturated aqueous NH$_4$Cl (20 mL) The resultant solution was extracted with EtOAc (200 mL×3). The combined organic layers were dried, and evaporated. The residue was purified by silica gel chromatography (PE/EtOAc=5:1) to give the title compound (7.7 g, 64% yield) as a yellow oil. LCMS (Method C): RT=0.958 min, m/z: 300.8 [M+H$^+$].

Step 4

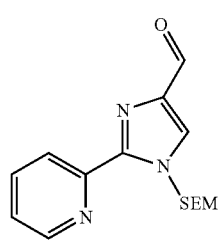 [SMILES: C[Si](C)(C)CCOCn1cc(C=O)nc1-c1ccccn1]

2-(pyridin-2-yl)-1-(2-(trimethylsilyl)ethoxy)methyl)-1H-imidazole-4-carbaldehyde DIBAL-H (1 M, 15.0 mL, 15.0 mmol) was added dropwise to a stirred and cooled (−78° C.) solution of 2-(pyridin-2-yl)-1-((2-(trimethylsilyl)ethoxy)methyl)-1H-imidazole-4-carbonitrile (3.0 g, 10 mmol) in THF (50 mL). After addition, the mixture was stirred for 30 min at −45° C. and 1 h at 0° C. EtOH (5 mL) was added and the mixture was stirred for 1 h at 0° C. The solvent was evaporated and the residue was purified by silica gel chromatography (PE/EtOAc=2:1) to give the title compound (1.7 g, 57% yield) as a yellow solid. LCMS (Method C): RT=0.896 min, m/z: 303.8 [M+H$^+$].

Step 5

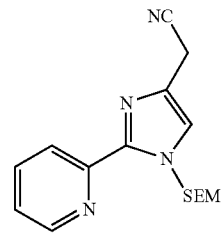 [SMILES: C[Si](C)(C)CCOCn1cc(CC#N)nc1-c1ccccn1]

2-(2-(pyridin-2-yl)-1((2-(trimethylsilyl)ethoxy)methyl)-1H-imidazol-4-yl)acetonitrile tBuOK (1 M in THF, 22.0 mL, 22.0 mmol), followed by a solution of 2-(pyridin-2-yl)-1-((2-(trimethylsilyl)ethoxy)methyl)-1H-imidazole-4-carbaldehyde (3.0 g, 10 mmol) in THF (5 mL) was added in portions to a stirred and cooled (−78° C.) solution of TosMIC (2.2 g, 11.0 mmol) in THF (20 mL). After addition, the reaction mixture was stirred for 45 min at −55° C., quenched by addition of MeOH (50 mL) and then heated at reflux for 2.5 h. The solvent was evaporated and the residue was diluted with AcOH (10 mL). The mixture was extracted with EtOAc (80 mL×3). The combined organic layers were dried and evaporated. The residue was purified by silica gel chromatography (PE/EtOAc=2:1) to give the title compound (1.3 g, 42% yield) as a yellow oil. LCMS (Method A): RT=0.725 min, m/z: 314.9 [M+H$^+$].

Step 6

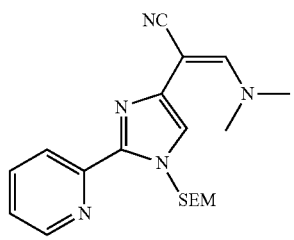 [SMILES: CN(C)/C=C(/C#N)c1cn(COCC[Si](C)(C)C)c(-c2ccccn2)n1]

3-(dimethylamino)-2-(2-(pyridin-2-yl)-1-((2-(trimethylsilyl)ethoxy)methyl)-1H-imidazol-4-yl)acrylonitrile 2-(2-(pyridin-2-yl)-1-((2-(trimethylsilyl)ethoxy)methyl)-1H-imidazol-4-yl)acetonitrile (625 mg, 2.0 mmol) in DMF-DMA (5 mL) was heated at reflux for 12 h and then concentrated to give the crude title compound (738 mg, 100% yield). This crude was used directly in the next step. LCMS (Method C): RT=0.706 min, m/z: 369.9 [M+H$^+$].

Step 7

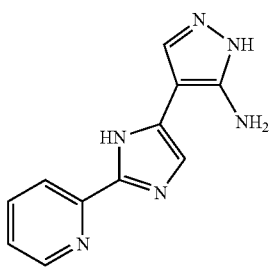 [SMILES: Nc1[nH]ncc1-c1cnc(-c2ccccn2)[nH]1]

4-(2-(pyridin-2-yl)-1H-imidazol-5-yl)-1H-pyrazol-5-amine

Concentrated HCl (0.2 mL) was added slowly to a stirred solution of hydrazine monohydrate (0.2 mL) in EtOH (10 mL), followed by 3-(dimethylamino)-2-(2-(pyridin-2-yl)-1-((2-trimethyl silyl)ethoxy)methyl)-1H-imidazol-4-yl)acrylonitrile (369 mg, 1 mmol). The resultant solution was heated at reflux for 2 h. After cooling, the mixture was adjusted to pH=9 by addition of 1 M aqueous $K_2CO_3$. The resulting mixture was then extracted with EtOAc (10 mL×3). The combined organic layers were dried and evaporated to give the crude title compound (110 mg, 49% yield) as an yellow oil. This crude was used in next step without further purification. LCMS (Method C): RT=0.200 min, m/z: 226.7 [M+H$^+$].

Step 8

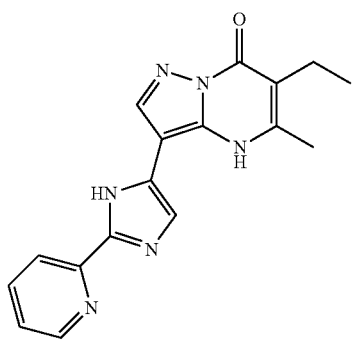 [SMILES: CCc1c(C)[nH]c2c(-c3cnc(-c4ccccn4)[nH]3)cnn2c1=O]

6-ethyl-5-methyl-3-(2-(pyridin-2-yl)-1H-imidazol-5-yl)pyrazolo[1,5-a]pyrimidin-7(4H)-one A mixture of 4-(2-(pyridin-2-yl)-1H-imidazol-5-yl)-1H-pyrazol-5-amine (150 mg, 0.66 mmol) and ethyl 2-ethyl-3-oxobutanoate (209 mg, 1.32 mmol) in AcOH (10 mL) was heated at 160° C. for 1 h. The solvent was evaporated and the residue was purified by preparative HPLC to give the title compound (10.6 mg, 5% yield) as a white solid. $^1$H NMR (400 MHz, DMSO-d$_6$): δ12.99 (br. s., 1H), 8.61-8.59 (m, 1H), 8.21-8.17 (m, 2H), 8.11 (s, 0.3H), 7.93-7.89 (m, 1H), 7.62 (s, 1H), 7.39-7.35 (m, 1H), 2.48-2.47 (m, 2H), 2.46 (s, 3H), 1.03 (t, J=7.2 Hz, 2H). LCMS (Method A): RT=0.932 min, m/z: 321.0 [M+H$^+$].

Example 45

Step 1

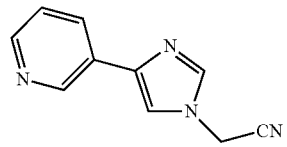

2-(4-(pyridin-3-yl)-1H-imidazol-1-yl)acetonitrile

A solution of 3-(1H-imidazol-4-yl)pyridine (8.0 g, 55.0 mmol) in tetrahydrofuran (100 mL) was added to a stirred and cooled (0° C.) suspension of NaH (60% dispersion in mineral oil, 3.0 g, 75.0 mmol) in THF (50 mL). Stirring continued for 30 min, and 2-bromoacetonitrile (6.5 g, 55.0 mmol) was added. After addition, the reaction mixture was stirred for 1 h at room temperature and then concentrated by evaporation. The residue was purified by silica gel chromatography (DCM/MeOH=10:1) to give the tile compound (7.5 g, 80% yield).

Step 2

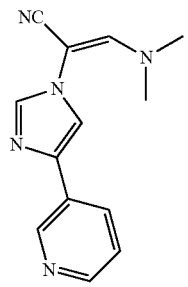 [SMILES: CN(C)/C=C(/C#N)n1cnc(-c2cccnc2)c1]

3-(dimethylamino)-2-(4-(pyridin-3-yl)-1H-imidazol-1-yl)acrylonitrile

A mixture of 2-(4-(pyridin-3-yl)-1H-imidazol-1-yl)acetonitrile (6.0 g, 35.2 mmol) in DMF-DMA (15 mL) was heated at 140° C. for 30 min under microwave irradiation and concentrated to give the crude title compound (6.0 g, 71% yield), which was used directly in the next step.

Step 3

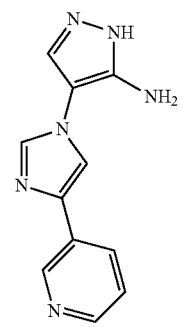 [SMILES: Nc1[nH]ncc1-n1cnc(-c2cccnc2)c1]

4-(4-(pyridin-3-yl)-1H-imidazol-1-yl)-1H-pyrazol-5-amine

Concentrated HCl (20 mL) was added slowly to a stirred solution of hydrazine monohydrate (2.0 mL) in EtOH (100 mL), followed by 3-(dimethylamino)-2-(4-(pyridin-3-yl)-1H-imidazol-1-yl)acrylonitrile (6.0 g, 25.1 mmol). The resultant solution was heated at reflux for 2 h. After cooling, the mixture was adjusted to pH=9 by addition of 1 M aqueous K$_2$CO$_3$. The resulting mixture was then extracted with EtOAc (100 mL×3). The combined organic layers were dried and concentrated by evaporation. The residue was purified by flash chromatography (DCM/MeOH=5:1) to give the title compound (4.8 g, 85% yield) as a yellow oil.

Step 4

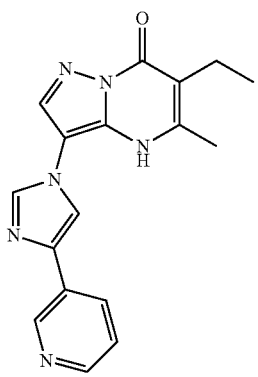

6-ethyl-5-methyl-3-(4-(pyridin-3-yl)-1H-imidazol-1-yl)pyrazolo[1,5-a]pyrimidin-7(4H)-one A mixture of 4-(4-(pyridin-3-yl)-1H-imidazol-1-yl)-1H-pyrazol-5-amine (4.8 g, 28.5 mmol) and ethyl 2-ethyl-3-oxobutanoate (5.9 g, 34 mmol) in AcOH (100 mL) was heated at reflux for 2 h. The solvent was evaporated and the residue was purified by preparative HPLC to give the title compound (623 mg, 9.2% yield) as a white solid. $^1$H NMR (400 MHz, DMSO-d$_6$): δ 9.04-9.03 (m, 1H), 8.43-8.41 (m, 1H), 8.17-8.13 (m, 3H), 8.01 (s, 1H), 7.42-7.39 (m, 1H), 2.50-2.48 (m, 2H), 2.29 (s, 3H), 1.02 (t, J=7.2 Hz, 6H). LCMS (Method A): RT=0.933 min, m/z: 320.9 [M+H$^+$].

Example 46

Step 1

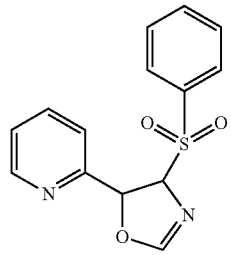

4-(phenylsulfonyl)-5-(pyridin-2-yl)-4,5-dihydrooxazole

KCN (2.7 g, 41.5 mmol) was added portionwise to a stirred solution of picolinaldehyde (10.0 g, 93.5 mmol) and 1-((isocyanomethyl)sulfonyl)-4-methylbenzene (18.0 g, 92.3 mmol) in ethanol (100 mL). The resulting mixture was stirred for 2 h at room temperature and then filtered. The solid was collected to give the crude title compound (20.0 g, 72% yield).

Step 2

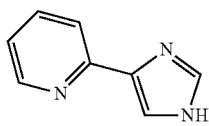 [SMILES: c1ccc(-c2c[nH]cn2)nc1]

2-(1H-imidazol-4-yl)pyridine

A solution of 4-(phenylsulfonyl)-5-(pyridin-2-yl)-4,5-dihydrooxazole (20.0 g, 65.8 mmol) and ammonia (70 mL, 7 N in methanol) was heated at 100° C. for 20 h. The solvent was evaporated and the residue was purified by silica gel chromatography (DCM/MeOH=10:1) to give the title compound (7.5 g, 79% yield) as a white solid.

Step 3

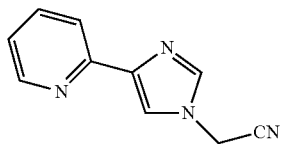 [SMILES: N#CCn1cnc(-c2ccccn2)c1]

2-(4-(pyridin-2-yl)-1H-imidazol-1-yl)acetonitrile

A solution of 2-(1H-imidazol-4-yl)pyridine (7.5 g, 51.7 mmol) in tetrahydrofuran (80 mL) was added to a stirred and cooled (0° C.) suspension of NaH (60%, 2.5 g, 62.5 mmol) in THF (20 mL). Stirring continued for 30 min, and 2-bromoacetonitrile (6.2 g, 51.7 mmol) was added. After addition, the reaction mixture was stirred for 1 h at room temperature and then evaporated to dryness. The residue was purified by silica gel chromatography (DCM/MeOH=10:1) to give the tile compound (10.0 g, 105% yield) as a yellow oil.

Step 4

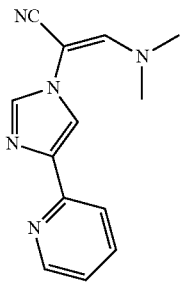

3-(dimethylamino)-2-(4-(pyridin-2-yl)-1H-imidazol-1-yl)acrylonitrile

A mixture of 2-(4-(pyridin-2-yl)-1H-imidazol-1-yl)acetonitrile (10.0 g, 54.3 mmol) in DMF-DMA (15 mL) was heated at 140° C. for 30 min under microwave conditions. The solvent was evaporated to give the crude title compound (11.0 g, 100%). It was used in the next step directly. LCMS (Method C): RT=1.85 min, m/z: 240.1 [M+H$^+$].

Step 5

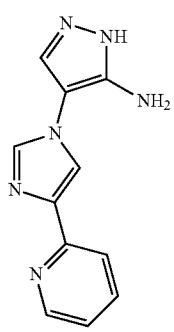 [SMILES: Nc1[nH]ncc1-n1cnc(-c2ccccn2)c1]

4-(4-(pyridin-2-yl)-1H-imidazol-1-yl)-1H-pyrazol-5-amine

Concentrated HCl (15 mL) was added slowly to a stirred solution of hydrazine monohydrate (6.0 mL) in EtOH (100 mL), followed by 3-(dimethylamino)-2-(4-(pyridin-2-yl)-1H-imidazol-1-yl)acrylonitrile (11.0 g, 46.0 mmol). The resultant solution was heated at reflux for 2 h. After cooling, the mixture was adjusted to pH=9 by addition of 1 M aqueous K$_2$CO$_3$. The resulting mixture was then extracted with EtOAc (200 mL×3). The combined organic layers were dried and evaporated. The residue was purified by flash chromatography (DCM/MeOH=10:1) to give the title compound (7.0 g, 67% yield) as a yellow oil. LCMS (Method C): RT=0.479 min, m/z: 226.8 [M+H$^+$].

Step 6

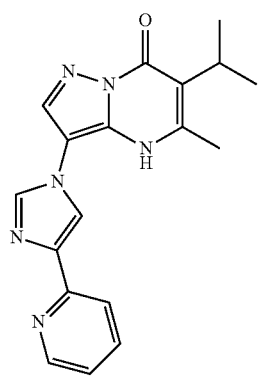 [SMILES: Cc1[nH]c2c(-n3cnc(-c4ccccn4)c3)cnn2c(=O)c1C(C)C]

6-isopropyl-5-methyl-3-(4-(pyridin-2-yl)-1H-imidazol-1-yl)pyrazolo[1,5-a]pyrimidin-7(4H)-one A mixture of 4-(4-(pyridin-2-yl)-1H-imidazol-1-yl)-1H-pyrazol-5-amine (600 mg, 2.6 mmol) and ethyl 2-acetyl-3-methylbutanoate (600 mg, 3.5 mmol) in AcOH (6 mL) was heated at reflux for 2 h. The solvent was evaporated and the residue was purified by preparative HPLC to give the title compound (100 mg, 11% yield) as a white solid. $^1$H NMR (400 MHz, DMSO-d$_6$): δ 12.04 (br. s., 1H), 8.50 (d, J=4.8 Hz, 1H), 8.10 (s, 1H), 7.94-7.81 (m, 4H), 7.22 (s, 1H), 3.04-2.97 (m, 1H), 2.33 (s, 3H), 1.28 (d, J=6.8 Hz, 6H). LCMS (Method C): RT=0.657 min, m/z: 335.0 [M+H$^+$].

Example 47

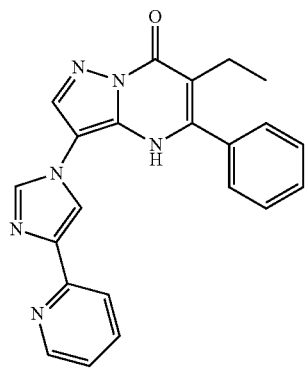 [SMILES: CCc1c(-c2ccccc2)[nH]c2c(-n3cnc(-c4ccccn4)c3)cnn2c1=O]

6-ethyl-5-phenyl-3-(4-(pyridin-2-yl)-1H-imidazol-1-yl)pyrazolo[1,5-a]pyrimidin-7(4H)-one In a similar procedure as shown in Example 46, the title compound was prepared in 7.5% yield from ethyl 2-benzylbutanoate. $^1$H NMR (400 MHz, DMSO-d$_6$): δ 12.66 (br. s., 1H), 8.05 (d, J=4.0 Hz, 1H), 8.22 (s, 1H), 7.94-7.82 (m, 3H), 7.82-7.78 (m, 1H), 7.55-7.50 (m, 5H), 7.22-7.19 (m, 1H), 2.31 (q, J=6.8 Hz, 2H), 1.00 (t, J=7.2 Hz, 3H). LCMS (Method C): RT=0.710 min, m/z: 382.9 [M+H$^+$].

Example 48

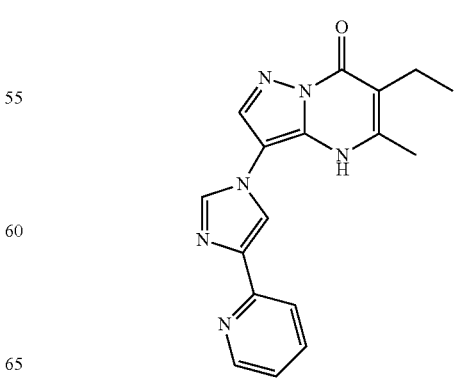

6-Ethyl-5-methyl-3-(4-(pyridin-2-yl)-1H-imidazol-1-yl)pyrazolo[1,5-a]pyrimidin-7(4H)-one In a similar procedure as shown in Example 46, the title compound was prepared in 16% yield from ethyl 2-ethyl-3-oxobutanoate. $^1$H NMR (300 MHz, CD$_3$OD): δ 8.54-8.52 (m, 1H), 8.35 (d, J=7.8 Hz, 1H), 8.11 (s, 1H), 8.06 (s, 2H), 8.00-7.98 (m, 1H), 7.92-7.89 (m, 1H), 7.33-7.29 (m, 1H), 6.18 (d, J=7.8 Hz, 1H). MS m/z: 279 [M+H$^+$].

Example 49

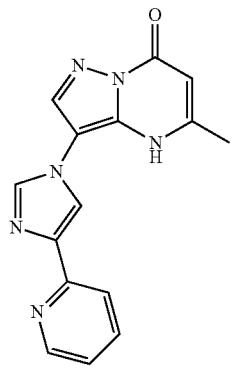 [SMILES: Cc1cc(=O)n2ncc(-n3cnc(-c4ccccn4)c3)c2[nH]1]

5-Methyl-3-(4-(pyridin-2-yl)-1H-imidazol-1-yl)pyrazolo[1,5-a]pyrimidin-7(4H)-one In a similar procedure as shown in Example 46, the title compound was prepared in 46% yield from ethyl 3-oxobutanoate. $^1$H NMR (300 MHz, CD$_3$OD): δ 8.59-8.57 (d, J=5.1 Hz, 1H), 8.23 (s, 1H), 8.11 (s, 1H), 8.04-8.02 (m, 2H), 7.96-7.94 (m, 1H), 7.39-7.37 (m, 1H), 5.91 (s, 1H), 2.44 (s, 3H). MS m/z: 293 [M+H$^+$].

Example 50

Step 1

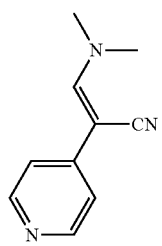

(Z)-3-(dimethylamino)-2-(4-pyridyl)prop-2-enenitrile

A mixture of 2-(4-pyridyl)acetonitrile (1.0 g, 8.46 mmol) in DMF-DMA (11.3 mL) and DMF was heated at 125° C. for 18 h. The reaction mixture was diluted with ice-water, extracted with EtOAc (6×). The combined organics were dried (Na$_2$SO$_4$), filtered and concentrated. The crude product was purified by silica flash chromatography (0-5% MeOH/DCM) to give the title compound (1.236 g, 84.3% yield) as a yellow solid. $^1$H NMR (400 MHz, DMSO-d$_6$) δ 8.38-8.27 (m, 2H), 7.80 (s, 1H), 7.32-7.22 (m, 2H), 3.26 (s, 6H). LCMS (ESI) m/z 174 [M+H$^+$].

Step 2

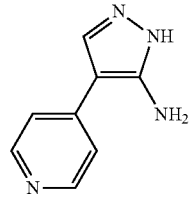 [SMILES: Nc1[nH]ncc1-c1ccncc1]

4-(4-pyridyl)-1H-pyrazol-5-amine

To a solution of (Z)-3-(dimethylamino)-2-(4-pyridyl)prop-2-enenitrile (1.235 g, 7.130 mmol) in EtOH (30 mL) was added hydrazine hydrate (80 mass % in water) (2.856 g, 71.30 mmol), followed by concentrated HCl solution until pH reached 3.0 (about 3.5 mL). The mixture was heated at 90° C. for 30 min. The reaction mixture was cooled to room temperature, neutralized with 1 M Na$_2$CO$_3$, extracted with EtOAc (3×). The combined organics were dried (Na$_2$SO$_4$), filtered and concentrated to give the title compound (1.0 g, 87.6% yield) as a yellow solid which was used in the next step without purification. LCMS (ESI) m/z 161 [M+H$^+$].

Step 3

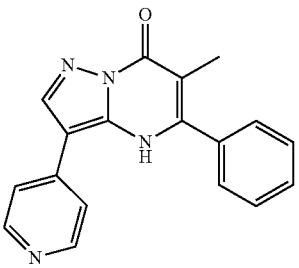 [SMILES: Cc1c(-c2ccccc2)[nH]c2c(-c3ccncc3)cnn2c1=O]

6-methyl-5-phenyl-3-(4-pyridyl)-4H-pyrazolo[1,5-a]pyrimidin-7-one

A mixture of 4-(4-pyridyl)-1H-pyrazol-5-amine (100 mg, 0.624 mmol), ethyl 2-methyl-3-oxo-3-phenyl-propanoate (193 mg, 0.936 mmol) and H$_2$SO$_4$ (191 mg, 1.87 mmol) in EtOH (2 mL) was heated at 80° C. for 24 h. The mixture was cooled to room temperature. A precipitate formed and was collected by filtration. The filter cake was washed with ether, dried under vacuum to give the title compound (112 mg, 59.4% yield) as a yellow solid. $^1$H NMR (400 MHz, DMSO-d6) δ 8.50 (s, 1H), 8.40 (d, J=6.35 Hz, 2H), 8.20 (s, 2H), 7.62-7.54 (m, 2H), 7.53-7.39 (m, 3H), 6.54 (s, 1H), 1.99 (s, 3H). LCMS (ESI) m/z 303 [M+H$^+$].

Example 51

Step 1

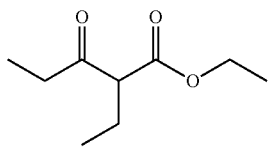

Ethyl 2-ethyl-3-oxopentanoate

A solution of ethyl 3-oxopentanoate (2.0 g, 14 mmol) in THF (20 mL) was cooled to 0° C. before addition of sodium hydride (60% dispersion in mineral oil, 0.64 g, 16.0 mmol). The resulting mixture was stirred at room temperature for 0.5 h before slow addition of bromoethane (1.7 g, 16 mmol). The mixture was stirred at room temperature for 1 h before being diluted with water (100 mL). The reaction mixture was extracted with ethyl acetate (100 mL) and the combined organics layer was dried over $Na_2SO_4$, filtered, and concentrated to afford crude ethyl 2-ethyl-3-oxopentanoate (1.2 g) as yellow oil.

Step 2

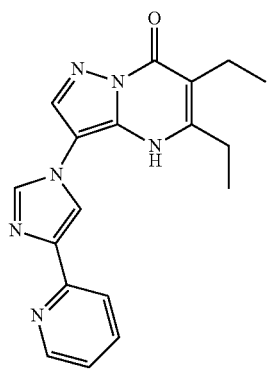 [SMILES: CCc1[nH]c2c(-n3cnc(-c4ccccn4)c3)cnn2c(=O)c1CC]

5,6-Diethyl-3-(4-(pyridin-2-yl)-1H-imidazol-1-yl)pyrazolo[1,5-a]pyrimidin-7(4H)-one In a similar procedure as shown in Example 46, the title compound was prepared in 4% yield from ethyl 2-ethyl-3-oxopentanoate. $^1$H NMR (300 MHz, CD3OD): δ 8.50 (d, J=3.9 Hz, 1H), 8.09 (s, 1H), 7.95-7.83 (m, 4H), 7.30 (s, 1H), 4.92 (s, 1H), 3.32-2.61 (m, 4H), 1.18 (t, J=7.2 Hz, 3H), 1.28 (t, J=7.5 Hz, 1H). MS m/z: 335 [M+H$^+$].

Example 52

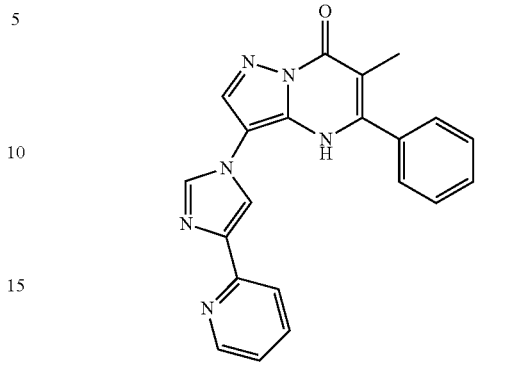

6-Methyl-5-phenyl-3-(4-(pyridin-2-yl)-1H-imidazol-1-yl)pyrazolo[1,5-a]pyrimidin-7(4H)-one In a similar procedure as shown in Example 46, the title compound was prepared in 6% yield from ethyl 2-methyl-3-oxo-3-phenylpropanoate. $^1$H NMR (300 MHz, DMSO-d$_6$): δ 8.52 (s, 1H), 8.25 (s, 1H), 7.82-7.99 (m, 4H), 7.55 (s, 5H), 7.23 (s, 1H), 1.94 (s, 3H). MS m/z: 369 [M+H$^+$].

Example 53

Step 1

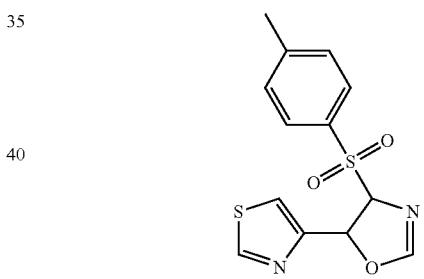

5-(Thiazol-4-yl)-4-tosyl-4,5-dihydrooxazole

To a solution of thiazole-4-carbaldehyde (3.2 g, 28.0 mmol) and 1-(isocyanomethylsulfonyl)-4-methylbenzene (5.0 g, 25.6 mmol) in ethanol (75 mL), was added finely powdered potassium cyanide (0.17 g, 2.6 mmol). The resulting mixture was stirred at room temperature for 2 h before the solids were collected by filtration. The solids were washed with ether (100 mL) and dried to afford 5-(thiazol-4-yl)-4-tosyl-4,5-dihydrooxazole as a yellow solid (5.5 g, 65% yield).

Step 2

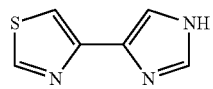

4-(1H-Imidazol-5-yl)thiazole

To a pressure tube was added 5-(thiazol-4-yl)-4-tosyl-4,5-dihydrooxazole (5.0 g, 16 mmol), aqueous ammonia (150 mL), and methanol (150 mmol). The resulting mixture was stirred at 120° C. for 20 h. After cooling to room temperature the mixture was concentrated and the residue was purified on silica gel (dichloromethane:methanol=10:1) to afford 4-(1H-imidazol-5-yl)thiazole as a solid (2.0 g, 86% yield). MS m/z: 152 [M+H$^+$].

Step 3

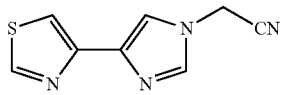 [SMILES: N#CCn1cnc(-c2cscn2)c1]

2-(4-(Thiazol-4-yl)-1H-imidazol-1-yl)acetonitrile

To a solution of 4-(1H-imidazol-5-yl)thiazole (1.5 g, 10.3 mmol) dissolved in THF (150 mL) was added sodium hydride (250 mg, 10.3 mmol) at 0° C. The mixture was stirred for 30 min before dropwise addition of 2-bromoacetonitrile (1.24 g, 10.3 mmol). The resulting mixture was stirred at room temperature for 3 h before being diluted with water, extracted with dichloromethane, dried over anhydrous sodium sulfate, filtered, and concentrated. The crude residue was purified on silica gel (dichloromethane:methanol=10:1) to afford 2-(4-(thiazol-4-yl)-1H-imidazol-1-yl)acetonitrile (1.0 g, 53% yield) as yellow solid. MS m/z: 191 [M+H$^+$].

Step 4

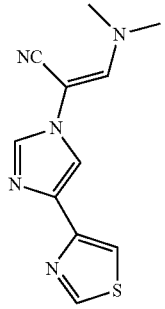 [SMILES: CN(C)/C=C(\C#N)n1cnc(-c2cscn2)c1]

(E)-3-(Dimethylamino)-2-(4-(thiazol-4-yl)-1H-imidazol-1-yl)acrylonitrile

A solution of 2-(4-(thiazol-4-yl)-1H-imidazol-1-yl)acetonitrile (200 mg, 1.1 mmol) and dimethylformamide dimethylacetal (260 mg, 2.2 mmol) in acetonitrile (10 mL) was heated to reflux for 2 h. The solvent was evaporated in vacuo and ethyl acetate was added to the mixture. The solids were collected via filtration to afford (E)-3-(dimethylamino)-2-(4-(thiazol-4-yl)-1H-imidazol-1-yl)acrylonitrile as an yellow solid (110 mg, 65% yield). MS m/z: 246 [M+H$^+$].

Step 5

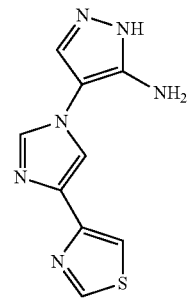 [SMILES: Nc1[nH]ncc1-n1cnc(-c2cscn2)c1]

4-(4-(Thiazol-4-yl)-1H-imidazol-1-yl)-1H-pyrazol-5-amine

To a solution of (E)-3-(dimethylamino)-2-(4-(thiazol-4-yl)-1H-imidazol-1-yl)acrylonitrile (100 mg, 0.41 mmol) and hydrazine hydrate (0.2 mL, 1 mmol) in ethanol (10 mL) at 0° C. was added aqueous hydrochloric acid until the pH=1-2. The reaction mixture was then heated to reflux for 2 h before cooling to room temperature and diluting with water. The mixture was extracted with ethyl acetate and the combined organics layer was washed with brine, dried over sodium sulfate, filtered, and concentrated. The crude residue was then purified on silica gel (dichloromethane:methanol=10:1) to afford 4-(4-(thiazol-4-yl)-1H-imidazol-1-yl)-1H-pyrazol-5-amine as off-white solid (60 mg, 58% yield). MS m/z: 233 [M+H$^+$].

Step 6

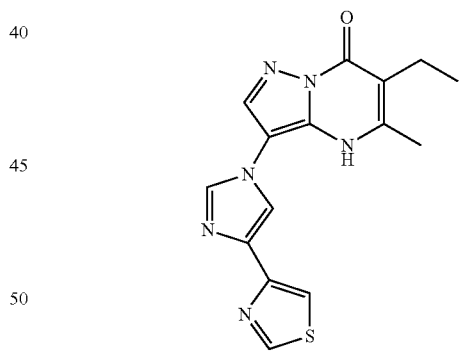

6-Ethyl-5-methyl-3-(4-(thiazol-4-yl)-1H-imidazol-1-yl)pyrazolo[1,5-a]pyrimidin-7(4H)-one A mixture of 4-(4-(thiazol-4-yl)-1H-imidazol-1-yl)-1H-pyrazol-5-amine (60 mg, 0.26 mmol) and ethyl 2-ethyl-3-oxobutanoate (61 mg, 0.38 mmol) in acetic acid (10 mL) was stirred at 150° C. for 2 h under microwave heating. The solution was then cooled to room temperature and concentrated. The crude residue was dissolved in water and extracted with ethyl acetate. The combined organics layer was washed with brine, dried over sodium sulfate, filtered, and concentrated. The crude residue was purified on silica gel (dichloromethane:methanol=10:1) to afford desired product as an off-white solid (30 mg, 30% yield). $^1$H NMR (300 MHz, CD$_3$OD): δ 9.05 (s, 1H), 8.10 (s, 1H), 7.94 (s, 1H), 7.80 (s, 1H), 7.69 (s, 1H), 2.63 (q, J=7.2 Hz, 2H), 2.41 (s, 3H), 1.15 (t, J=7.2 Hz, 3H). MS m/z: 327 [M+H$^+$].

Example 54

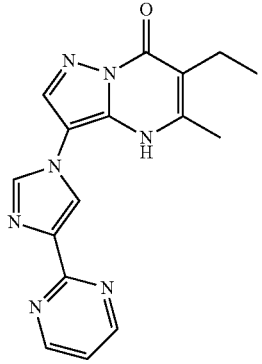 [SMILES: CCc1c(C)[nH]c2c(-n3cnc(-c4ncccn4)c3)cnn2c1=O]

6-ethyl-5-methyl-3-(4-(pyrimidin-2-yl)-1H-imidazol-1-yl)pyrazolo[1,5-a]pyrimidin-7(4H)-one This compound was prepared following a similar procedure as that shown in Example 53. $^1$H NMR (300 MHz, DMSO-d$_6$): δ 8.82-8.80 (m, 3H), 8.19-8.15 (m, 2H), 7.46 (s, 1H), 2.52-2.50 (q, J=7.5 Hz, 2H), 2.36 (s, 3H), 1.04-0.99 (t, J=7.5 Hz, 3H). MS m/z: 322 [M+H$^+$].

Example 55

Step 1

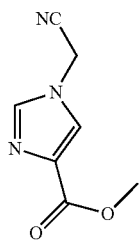

methyl 1-(cyanomethyl)-1H-imidazole-4-carboxylate

To a solution of methyl 1H-imidazole-4-carboxylate (3.78 g, 30 mmol) in anhydrous THF (60 mL) was added sodium hydride (0.72 g, 30 mmol). The solution was then stirred at room temperature for 1 h before addition of 2-bromoacetonitrile (4.2 g, 35 mmol). The reaction was stirred at room temperature for 2 h before being concentrated in vacuo. The crude residue was purified on silica gel (petroleum ether: ethyl acetate=3:1) to afford the desired product (2.48 g, 50% yield). MS m/z: 166 [M+H$^+$].

Step 2

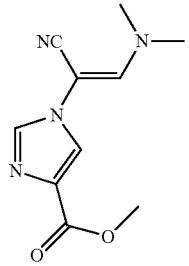 [SMILES: COC(=O)c1cn(/C(C#N)=C/N(C)C)cn1]

(E)-Methyl 1-(1-cyano-2-(dimethylamino)vinyl)-1H-imidazole-4-carboxylate

To a solution of methyl 1-(cyanomethyl)-1H-imidazole-4-carboxylate (2.48 g, 15 mmol) in anhydrous DMF (30 mL) was added dimethoxy-N,N-dimethylmethanamine (7.2 g, 60 mmol). The solution was then heated to 100° C. and stirred for 3 h. The reaction mixture was then cooled to room temperature and concentrated to afford the crude desired product (3.3 g, 100% yield).

Step 3

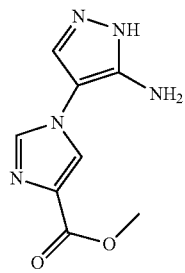

Methyl 1-(5-amino-1H-pyrazol-4-yl)-1H-imidazole-4-carboxylate

To a solution of (E)-methyl 1-(1-cyano-2-(dimethylamino)vinyl)-1H-imidazole-4-carboxylate (3.3 g, 15 mmol) in ethanol (50 mL) was added hydrazine monohydrate (10 mL). The reaction was then stirred at reflux for 2 h before concentration to dryness. The crude residue was purified on silica gel (dichloromethane:methanol=20:1) to afford the desired product (1.86 g, 60% yield). MS m/z: 208 [M+H$^+$].

Step 4

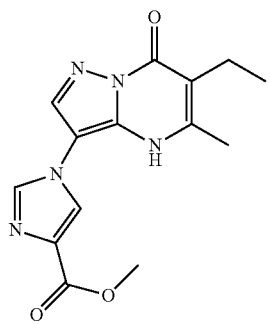 [SMILES: CCc1c(C)[nH]c2c(-n3cnc(C(=O)OC)c3)cnn2c1=O]

Methyl 1-(6-ethyl-5-methyl-7-oxo-4,7-dihydropyra-
zolo[1,5-a]pyrimidin-3-yl)-1H-imidazole-4-carboxy-
late To a solution of methyl 1-(5-amino-1H-pyrazol-4-yl)-1H-imidazole-4-carboxylate (1.86 g, 9 mmol) in acetic acid (20 mL) was added ethyl 2-ethyl-3-oxobutanoate (2.37 g, 15 mmol). The reaction was then heated to reflux and stirred for 4 h. The reaction mixture was cooled to room temperature and concentrated in vacuo. The crude residue was purified on silica gel (dichloromethane:methanol=15:1) to afford the desired product (1.35 g, 50% yield). MS m/z: 302 [M+H$^+$].

Step 5

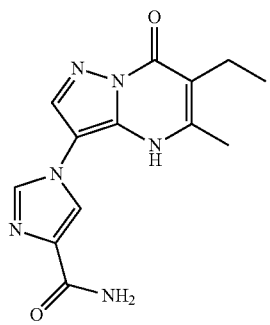 [SMILES: CCc1c(C)[nH]c2c(-n3cnc(C(N)=O)c3)cnn2c1=O]

1-(6-Ethyl-5-methyl-7-oxo-4,7-dihydropyrazolo[1,5-a]pyrimidin-3-yl)-1H-imidazole-4-carboxamide A solution of methyl 1-(6-ethyl-5-methyl-7-oxo-4,7-dihydropyrazolo[1,5-c]pyrimidin-3-yl)-1H-imidazole-4-carboxylate (301 mg, 1 mmol) dissolved in methanolic ammonia (7 M, 20 mL) was stirred at 150° C. for 12 h. The reaction mixture was cooled to room temperature and concentrated in vacuo. The crude residue was purified on silica gel (dichloromethane:methanol=10:1) to give the desired product (143 mg, 50% yield). $^1$H NMR (300 MHz, DMSO-d$_6$): δ 12.20 (s, 1H), 8.10 (s, 1H), 7.90 (s, 1H), 7.84 (s, 1H), 7.42 (s, 1H), 7.17 (s, 1H), 2.48 (q, J=7.2 Hz, 2H), 2.32 (s, 3H), 1.02 (t, J=7.2 Hz, 3H). MS m/z: 287 [M+H$^+$].

Example 56

Step 1

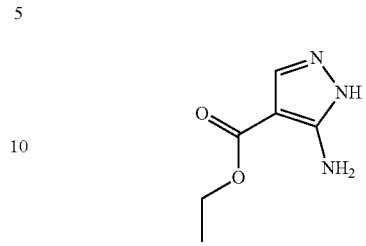

Ethyl 5-amino-1H-pyrazole-4-carboxylate

To a mixture of 2-cyano-3-ethoxy-acrylic acid ethyl ester (10 g, 59 mmol) in ethanol (100 mL) was added hydrazine hydrate (3.6 g, 71 mmol). The mixture was stirred at reflux for 3 h before being concentrated in vacuo to afford the crude product. This material was used in subsequent reactions without further purification. MS m/z: 156 [M+H$^+$].

Step 2

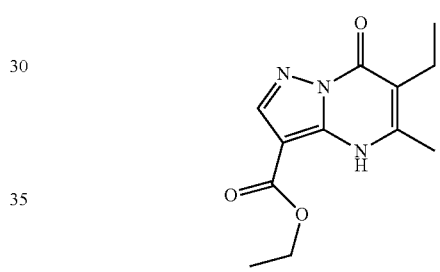

Ethyl 6-ethyl-5-methyl-7-oxo-4,7-dihydropyrazolo
[1,5-a]pyrimidine-3-carboxylate To a mixture of ethyl 5-amino-1H-pyrazole-4-carboxylate (100 mg, 0.65 mmol) in acetic acid (5 mL) was added 2-ethyl-3-oxo-butyric acid ethyl ester (102 mg, 0.65 mmol). The mixture was stirred at reflux for 12 h under nitrogen before cooling to room temperature. The solvent was removed in vacuo to afford a crude residue. The crude product was purified on silica gel (petroleum ether:ethyl acetate=8:5) to afford the desired product (110 mg, 70% yield). MS m/z: 250 [M+H$^+$].

Step 3

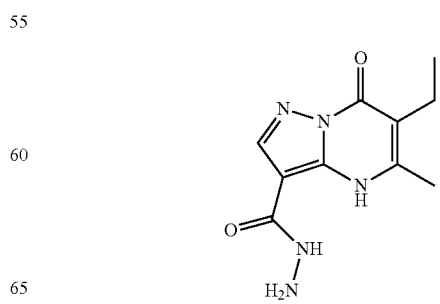

6-Ethyl-5-methyl-7-oxo-4,7-dihydropyrazolo[1,5-a]pyrimidine-3-carbohydrazide To a mixture of 6-ethyl-5-methyl-7-oxo-4,7-dihydropyrazolo[1,5-a]pyrimidine-3-carboxylic acid ethyl ester (100 mg, 0.4 mmol) in ethanol (10 mL) was added hydrazine hydrate (401 mg, 20 mmol). The mixture was stirred at reflux for 12 h before cooling the reaction to room temperature and concentrating. The crude residue was purified by HPLC to afford 6-ethyl-5- the desired product (30 mg, 32% yield). MS m/z: 236 [M+H$^+$].

Step 4

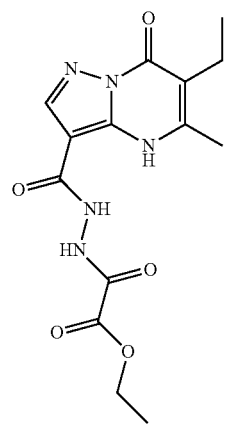 [SMILES: CCOC(=O)C(=O)NNC(=O)c1cnn2c(=O)c(CC)c(C)[nH]c12]

Ethyl 2-(2-(6-ethyl-5-methyl-7-oxo-4,7-dihydropyrazolo[1,5-a]pyrimidine-3-carbonyl)hydrazinyl)-2-oxoacetate To a mixture of 6-ethyl-5-methyl-7-oxo-4,7-dihydropyrazolo[1,5-a]pyrimidine-3-carbohydrazide (500 mg, 2.13 mmol) in dichloromethane:DMF (10 mL:10 mL) was added triethylamine (430 mg, 4.26 mmol). Then chloro-oxo-acetic acid ethyl ester (579 mg, 4.26 mmol) was added and the mixture was stirred at room temperature for 4 h. The solvent was evaporated and the crude residue was purified on silica gel (dichloromethane: methanol=15:1) to afford the desired product (700 mg, 82% yield) as a white solid. MS m/z: 336 [M+H$^+$].

Step 5

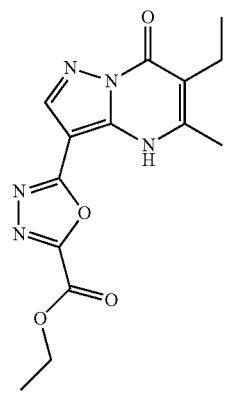 [SMILES: CCOC(=O)c1nnc(-c2cnn3c(=O)c(CC)c(C)[nH]c23)o1]

Ethyl 5-(6-ethyl-5-methyl-7-oxo-4,7-dihydropyrazolo[1,5-a]pyrimidin-3-yl)-1,3,4-oxadiazole-2-carboxylate To a solution of 2-(2-(6-ethyl-5-methyl-7-oxo-4,7-dihydropyrazolo[1,5-a]pyrimidine-3-carbonyl)hydrazinyl)-2-oxoacetate (100 mg, 0.3 mmol) in dichloromethane:DMF (5 mL:5 mL) was added 4-methylbenzene-1-sulfonyl chloride (171 mg, 0.9 mmol) and triethylamine (91 mg, 0.9 mmol). The mixture was stirred at room temperature for 5 h before the solution was concentrated. The crude residue was purified on silica gel (dichloromethane:methanol=25:1) to afford the desired product (50 mg, 52% yield) as a white solid. MS m/z: 318 [M+H$^+$].

Step 6

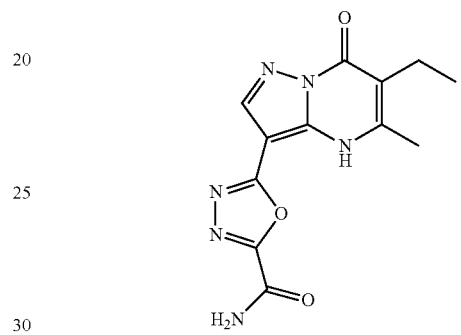

5-(6-Ethyl-5-methyl-7-oxo-4,7-dihydropyrazolo[1,5-a]pyrimidin-3-yl)-1,3,4-oxadiazole-2-carboxamide Ethyl 5-(6-ethyl-5-methyl-7-oxo-4,7-dihydro-pyrazolo[1,5-a]pyrimidin-3-yl)-1,3,4-oxadiazole-2-carboxylate (50 mg, 0.16 mmol) was dissolved in ammonium hydroxide (7 mL). The mixture was stirred at room temperature for 12 h before being concentrated. The crude residue was purified via HPLC to afford the desired product (15 mg, 33% yield) as a white solid. $^1$H NMR (300 MHz, DMSO-d$_6$): δ 12.03 (s, 1H), 8.63 (s, 1H), 8.40 (s, 1H), 8.29 (s, 1H), 4.05 (s, 1H), 2.53 (t, J=7.8 Hz, 2H), 2.44 (s, 3H), 1.05 (t, J=7.2 Hz, 3H). MS m/z: 289 [M+H$^+$].

Example 57

Step 1

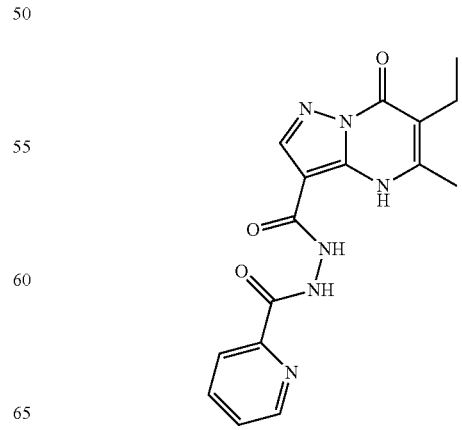

6-ethyl-5-methyl-7-oxo-N'-picolinoyl-4,7-dihydro-pyrazolo[1,5-a]pyrimidine-3-carbohydrazide To a mixture of pyridine-2-carboxylic acid (170 mg, 1.4 mmol) in DMF (10 mL) were added 1-(3-dimethylaminopropyl)-3-ethylcarbodiimide hydrochloride (480 mg, 2.5 mmol) and N-hydroxybenzotriazole (420 mg, 2.5 mmol). The mixture was stirred at room temperature for 1 h before addition of 6-ethyl-5-methyl-7-oxo-4,7-dihydropyrazolo[1,5-a]pyrimidine-3-carbohydrazide (300 mg, 1.3 mmol). The mixture was stirred at 40° C. for 12 h before being concentrated. The crude residue was purified via prep-TLC to give the desired product (85 mg, 18% yield). MS m/z: 341 [M+H$^+$].

Step 2

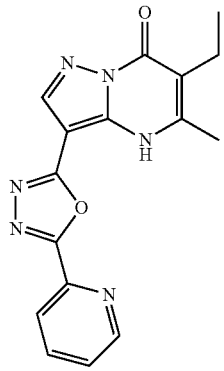 [SMILES: CCc1c(C)[nH]c2c(-c3nnc(-c4ccccn4)o3)cnn2c1=O]

6-Ethyl-5-methyl-3-(5-(pyridin-2-yl)-1,3,4-oxadiazol-2-yl)pyrazolo[1,5-a]pyrimidin-7(4H)-one To a solution of 6-ethyl-5-methyl-7-oxo-N'-picolinoyl-4,7-dihydropyrazolo[1,5-a]pyrimidine-3-carbohydrazide (78 mg, 0.23 mmol) in dichloromethane:DMF (5 mL:5 mL) was added 4-methylbenzene-1-sulfonyl chloride (130 mg, 0.69 mmol) and triethylamine (70 mg, 0.69 mmol). The mixture was stirred at room temperature for 5 h before being concentrated. The crude residue was purified by HPLC to afford the desired product (5 mg, 6% yield). $^1$H NMR (300 MHz, DMSO-d$_6$): δ 8.81 (d, J=5.6 Hz, 1H), 8.39 (s, 1H), 8.24 (d, J=7.9 Hz, 1H), 8.08 (t, J=9.0 Hz, 1H), 7.64 (dd, J=7.4, 4.8 Hz, 1H), 2.55 (t, J=7.5 Hz, 2H), 2.48 (s, 3H), 1.06 (t, J=7.3 Hz, 3H). MS m/z: 323 [M+H$^+$].

Example 58

Step 1

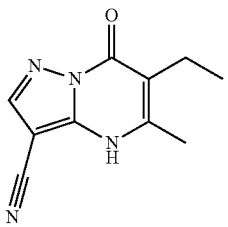

6-Ethyl-5-methyl-7-oxo-4,7-dihydropyrazolo[1,5-a]pyrimidine-3-carbonitrile

A mixture of 5-amino-1H-pyrazole-4-carbonitrile (4.0 g, 37 mmol) and ethyl 2-ethyl-3-oxobutanoate (5.8 g, 27 mmol) in acetic acid (40 mL) was stirred at 120° C. for 3 h. The mixture was concentrated, dissolved in water, and then 1N sodium hydroxide was added to the solution until a precipitate formed. The precipitate was collected via filtration and dried to afford the desired product (5.0 g, 67% yield). MS m/z: 203 [M+H$^+$].

Step 2

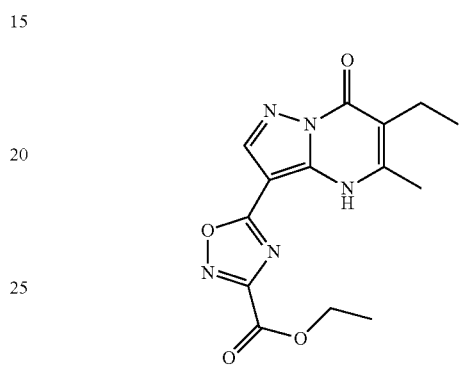

Ethyl 5-(6-ethyl-5-methyl-7-oxo-4,7-dihydropyrazolo[1,5-a]pyrimidin-3-yl)-1,2,4-oxadiazole-3-carboxylate To a mixture of 6-ethyl-5-methyl-7-oxo-4,7-dihydropyrazolo[1,5-a]pyrimidine-3-carbonitrile (0.5 g, 2.47 mmol) and (Z)-ethyl 2-chloro-2-(hydroxyimino)acetate (0.37 g, 2.47 mmol) in acetone (50 mL) was added triethylamine (0.5 g, 4.94 mmol). The mixture was stirred at 60° C. for 16 h, and then concentrated. The crude product was purified on silica gel (dichloromethane:methanol=3:1) to afford the desired product (230 mg, 30% yield) as a white solid. MS m/z: 318 [M+H$^+$].

Step 3

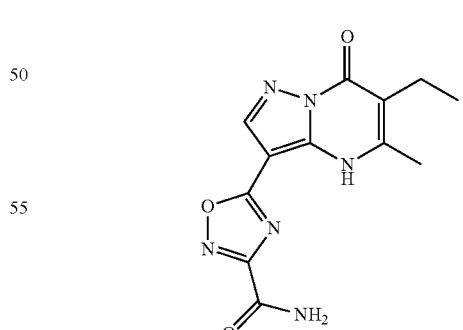

5-(6-Ethyl-5-methyl-7-oxo-4,7-dihydropyrazolo[1,5-a]pyrimidin-3-yl)-1,2,4-oxadiazole-3-carboxamide A mixture of 5-(6-ethyl-5-methyl-7-oxo-4,7-dihydropyrazolo[1,5-a]pyrimidin-3-yl)-1,2,4-oxadiazole-3-carboxylate (60 mg, 0.19 mmol) in ammonium hydroxide (5 mL) was stirred at 40° C. for 48 h before the mixture was concentrated. The crude residue was purified on silica gel (dichloromethane:methanol=3:1) to afford the desired product (8 mg, 14% yield) as a white solid. $^1$H NMR (300 MHz, CD$_3$OD) δ 8.21 (s, 1H), 2.73~2.66 (m, 2H), 2.27 (s, 3H), 1.15 (t, J=7.5 Hz, 3H). MS m/z: 289 [M+H$^+$].

Example 59

Step 1

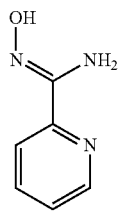

(Z)—N'-hydroxypicolinimidamide

To a solution of ammonium hydroxide (840 mg, 12 mmol) in methanol (50 mL) was added sodium bicarbonate (1.1 g, 13 mmol) and pyridine-2-carbonitrile (1 g, 9.6 mmol). The mixture heated to 60° C. for 2 h. The solvent was then evaporated and the crude residue was washed with water to afford the desired product (1 g, 77% yield). MS m/z: 138 [M+H$^+$].

Step 2

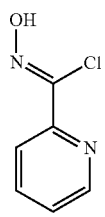

(Z)—N-hydroxypicolinimidoyl chloride (Z)—N'-hydroxypicolinamidine (170 mg, 1.24 mmol) was dissolved in a mixture of concentrated HCl (1 mL) and water (5 mL) at 0° C. To this solution was added sodium nitrite (85 mg, 1.24 mmol) dissolved in water (2 mL) and the mixture was stirred at 0° C. for 1 h. The pH of the reaction was adjusted with a saturated solution of sodium hydrogen carbonate until pH=3 was reached. The precipitate was filtered and washed with ice-cold water to afford the desired product (120 mg, 62% yield). MS m/z: 157 [M+H$^+$].

Step 3

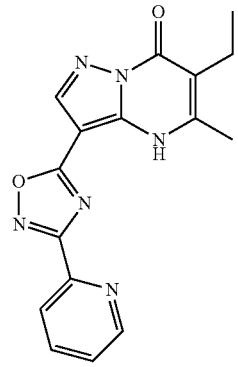 [SMILES: CCc1c(C)[nH]c2c(-c3nc(-c4ccccn4)no3)cnn2c1=O]

6-Ethyl-5-methyl-3-(3-(pyridin-2-yl)-1,2,4-oxadiazol-5-yl)pyrazolo[1,5-a]pyrimidin-7(4H)-one To a mixture of 6-ethyl-5-methyl-7-oxo-4,7-dihydropyrazolo[1,5-a]pyrimidine-3-carbonitrile (26 mg, 0.13 mmol) and (Z)—N-hydroxypicolinimidoyl chloride (20 mg, 0.13 mmol) in acetone (5 mL) was added triethylamine (2 mL). The mixture was heated to 70° C. and stirred for 2 h. The reaction was cooled to room temperature before concentration to dryness. The crude residue was purified via HPLC to afford the desired product (5 mg, 12% yield). $^1$H NMR (300 MHz, CD$_3$OD): δ 8.48 (d, J=4.5 Hz, 1H), 8.23 (d, J=8.1 Hz, 1H), 8.17 (s, 1H), 7.96 (t, J=8.6 Hz, 1H), 7.48 (dd, J=7.1, 4.5 Hz, 1H), 2.73 (q, J=7.4 Hz, 2H), 2.26 (s, 3H), 1.19 (t, J=7.4 Hz, 3H). MS m/z: 323 [M+H$^+$].

Example 60

Step 1

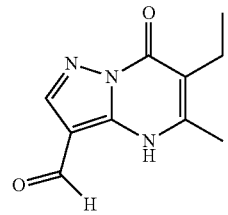

6-Ethyl-5-methyl-7-oxo-4,7-dihydropyrazolo[1,5-a]pyrimidine-3-carbaldehyde

To a round bottomed flask was added 6-ethyl-5-methyl-7-oxo-4,7-dihydropyrazolo[1,5-a]pyrimidine-3-carbonitrile (3.7 g, 18.3 mmol), water (8 mL), and formic acid (8 mL). This mixture was placed under an inert atmosphere before addition of Raney nickel (1.074 g, 18.3 mmol). The reaction was heated to 70° C. overnight before additional Raney nickel (1.074 g, 18.3 mmol) was added. The solution was heated to 70° C. for an additional 4 h before cooling to room temperature and filtering off the solids. The solids were washed with water and the filtrate was extracted with DCM. The combined organics layer was dried over Na$_2$SO$_4$, filtered, and concentrated. The crude residue was purified on silica gel (ethyl acetate:methanol) to afford the desired product (1.125 g, 30% yield) as a yellow solid. MS m/z: 206 [M+H⁺].

Step 2

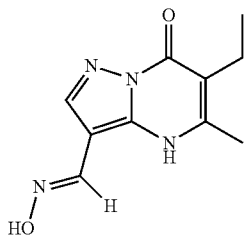 [SMILES: CCc1c(C)[nH]c2c(/C=N/O)cnn2c1=O]

(E)-6-Ethyl-5-methyl-7-oxo-4,7-dihydropyrazolo[1,5-a]pyrimidine-3-carbaldehyde oxime To a vial was added 6-ethyl-5-methyl-7-oxo-4,7-dihydropyrazolo[1,5-a]pyrimidine-3-carbaldehyde (400 mg, 1.95 mmol), hydroxylamine hydrochloride (271 mg, 3.90 mmol), and ethanol. To this solution was added 1 drop of concentrated HCl and the reaction was stirred overnight at room temperature. The precipitate was collected via filtration to afford the desired product (400 mg, 93% yield). MS m/z: 221 [M+H⁺].

Step 3

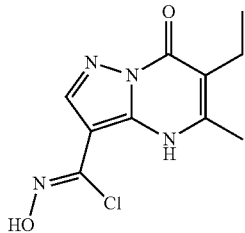 [SMILES: CCc1c(C)[nH]c2c(/C(Cl)=N/O)cnn2c1=O]

(Z)-6-Ethyl-N-hydroxy-5-methyl-7-oxo-4,7-dihydropyrazolo[1,5-a]pyrimidine-3-carbimidoyl chloride To a vial was added (E)-6-ethyl-5-methyl-7-oxo-4,7-dihydropyrazolo[1,5-a]pyrimidine-3-carbaldehyde oxime (140 mg, 0.63 mmol), dichloroethane, and N-chloro succinimide (102 mg, 0.76 mmol). The mixture was stirred at room temperature for 6 h before heating to 60° C. for 2 h. The solution was then cooled to room temperature and DMF was added. The reaction was stirred overnight at room temperature before diluting the reaction with water and extracting with DCM. The combined organics layer was dried over Na₂SO₄, filtered, and concentrated to crude product. This material was used in the subsequent reaction without further purification. MS m/z: 255 [M+H⁺].

Step 4

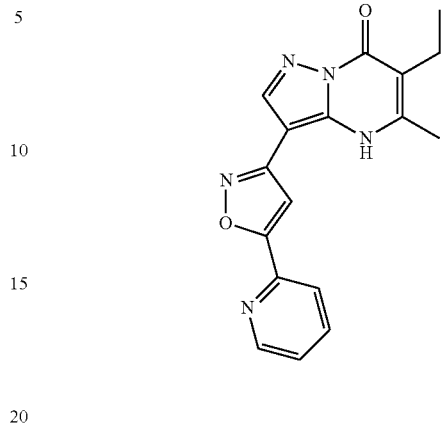

6-Ethyl-5-methyl-3-(5-(pyridin-2-yl)isoxazol-3-yl)pyrazolo[1,5-a]pyrimidin-7(4H)-one To a round bottomed flask was added (Z)-6-ethyl-N-hydroxy-5-methyl-7-oxo-4,7-dihydropyrazolo[1,5-a]pyrimidine-3-carbimidoyl chloride (162 mg, 0.64 mmol), ethyl acetate (20 mL), K₂CO₃ (176 mg, 1.27 mmol), and ethynylpyridine (193 uL, 1.91 mmol). The reaction was fitted with a reflux condenser and heated to reflux overnight. The reaction was cooled to room temperature and filtered. The solid was collected and purified via HPLC to afford the desired product (8 mg, 4% yield). $^1$H NMR (400 MHz, DMSO-$d_6$): δ 8.80-8.73 (m, 1H), 8.36 (s, 1H), 8.07-7.96 (m, 2H), 7.69 (s, 1H), 7.54 (ddd, J=1.4, 4.8, 7.3 Hz, 1H), 2.56-2.51 (m, 2H), 2.46 (s, 3H), 1.05 (t, J=7.3 Hz, 3H). MS m/z: 322 [M+H⁺].

LCMS Method A

Experiments performed on an Agilent 1200 HPLC (with a PDA detector and a ELSD detector) with Agilent 6100 MSD mass spectrometer using ESI as ionization source using an Xtimate TM-C18 30*2.1 mm column and a 0.8 ml/minute flow rate. Acquire Time: 2 min, Wavelength: UV220, Oven Temp.: 50° C. The solvent system was a gradient starting with 100% water containing 0.038% TFA (solvent A) and acetonitrile containing 0.02% TFA (solvent B), followed by a gradient up to 40% solvent A and 60% solvent B over the next 0.9 minutes. This was maintained for 0.6 minutes before returning to 100% solvent A and solvent B over the next 0.5 minute. Total run time was 2 min.

LCMS Method B

Experiments performed on an SHIMADZU 20A HPLC (with a PDA detector) with SHIMADZU 2010EV MSD mass spectrometer using ESI as ionization source using an Xtimate TM-C18 30*2.1 mm column and a 1.2 ml/minute flow rate. The solvent system was a gradient starting with 90% water containing 0.038% TFA (solvent A) and 10% acetonitrile containing 0.02% TFA (solvent B), followed by a gradient up to 20% solvent A and 80% solvent B over the next 0.9 minutes. This was maintained for 0.6 minutes before returning to 90% solvent A and 10% solvent B over the next 0.5 minute. Total run time was 2 min.

LCMS Method C

Experiments performed on an SHIMADZU 20A HPLC (with a PDA detector) with SHIMADZU 2010EV MSD mass spectrometer using ESI as ionization source using an Merk RP-18e 2*25 mm column and a 1.5 ml/minute flow rate. The solvent system was a gradient starting with 95% water containing 0.038% TFA (solvent A) and 5% acetonitrile containing 0.02% TFA (solvent B), followed by a gradient up to 5% solvent A and 95% solvent B over the next 0.7 minutes. This was maintained for 0.4 minutes before returning to 95% solvent A and 5% solvent B over the next 0.4 minute. Total run time was 1.5 min.

LCMS Method D

Experiments performed on a Agilent 6140 quadrupole LC/MS system linked to a HPLC Agilent 1200 system with a UV detector monitoring at 254 nm, and mass spectrometry scanning 90-1300 amu in ESI+ ionization mode. This system uses an Agilent SB C18 (1.8 um 30×2.1 mm) column, maintained at 25° C. and a 0.4 ml/minute flow rate. The initial solvent system was 95% water containing 0.05% TFA (solvent A) and 5% acetonitrile containing 0.05% TFA (solvent B) for the first 0.3 minute followed by a gradient up to 5% solvent A and 95% solvent B over the next 6.5 minutes. This was maintained for 1.5 minute before returning to 95% solvent A and 5% solvent B over the next 0.1 minutes. Total run time was 10 minutes.

TABLE 1

| Example | Structure | Name | Synth. Method | LCMS (ESI) m/z | NMR |
|---|---|---|---|---|---|
| 61 | 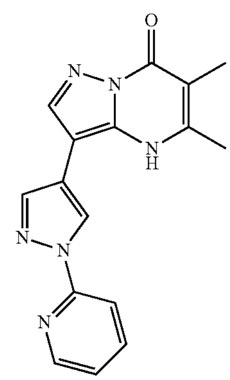 [SMILES: Cc1[nH]c2c(-c3cnn(-c4ccccn4)c3)cnn2c(=O)c1C] | 5,6-dimethyl-3-[1-(2-pyridyl)pyrazol-4-yl]-4H-pyrazolo[1,5-a]pyrimidin-7-one | B | 307 | $^1$H NMR (400 MHz, DMSO) δ 11.49 (s, 1H), 9.18-9.06 (d, J = 1.1 Hz, 1H), 8.60-8.47 (ddd, J = 4.6, 1.8, 0.9 Hz, 1H), 8.27-8.12 (m, 2H), 8.08-7.92 (m, 2H), 7.44-7.33 (m, 1H), 2.42 (s, 3H), 2.01 (s, 3H) |
| 62 | 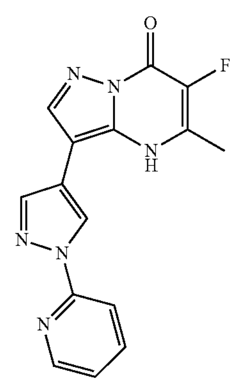 [SMILES: Cc1[nH]c2c(-c3cnn(-c4ccccn4)c3)cnn2c(=O)c1F] | 6-fluoro-5-methyl-3-[1-(2-pyridyl)pyrazol-4-yl]-4H-pyrazolo[1,5-a]pyrimidin-7-one | B | 311 | $^1$H NMR (400 MHz, DMSO-d6) δ 11.83 (s, 1H), 9.11 (d, J = 0.9 Hz, 1H), 8.52 (ddd, J = 4.8, 1.8, 0.9 Hz, 1H), 8.30 (s, 1H), 8.23 (d, J = 1.0 Hz, 1H), 8.07-7.95 (m, 2H), 7.43-7.33 (m, 1H), 2.45 (d, J = 3.4 Hz, 3H) |
| 63 | 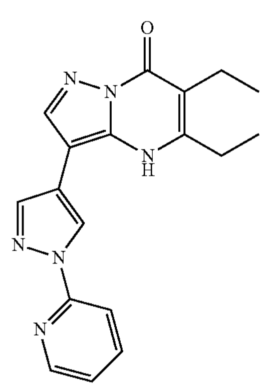 [SMILES: CCc1[nH]c2c(-c3cnn(-c4ccccn4)c3)cnn2c(=O)c1CC] | 5,6-diethyl-3-[1-(2-pyridyl)pyrazol-4-yl]-4H-pyrazolo[1,5-a]pyrimidin-7-one | B | 335 | $^1$H NMR (400 MHz, DMSO-d6) δ 11.39 (s, 1H), 9.09 (d, J = 1.0 Hz, 1H), 8.52 (ddd, J = 4.9, 1.8, 0.9 Hz, 1H), 8.23-8.17 (m, 2H), 8.07-7.94 (m, 2H), 7.43-7.34 (m, 1H), 2.76 (q, J = 7.5 Hz, 2H), 2.53 (q, J = 7.4 Hz, 2H), 1.27 (t, J = 7.5 Hz, 3H), 1.09 (t, J = 7.4 Hz, 3H) |

TABLE 1-continued

| Example | Structure | Name | Synth. Method | LCMS (ESI) m/z | NMR |
|---|---|---|---|---|---|
| 64 | 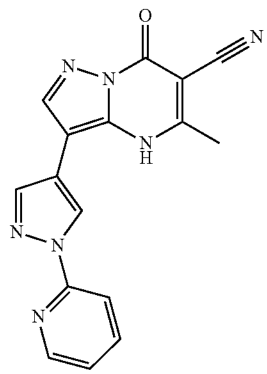 [SMILES: Cc1[nH]c2c(-c3cnn(-c4ccccn4)c3)cnn2c(=O)c1C#N] | 5-methyl-7-oxo-3-[1-(2-pyridyl)pyrazol-4-yl]-4H-pyrazolo[1,5-a]pyrimidine-6-carbonitrile | B | 318 | ¹H NMR (400 MHz, DMSO-d6) δ 12.81, (s, 1H), 9.22 (d, J = 0.8 Hz, 1H), 8.57-8.46 (m, 2H), 8.28 (d, J = 0.9 Hz, 1H), 8.06-7.92 (m, 2H), 7.37 (ddd, J = 7.2, 4.9, 1.3 Hz, 1H), 2.78 (s, 3H) |
| 65 | 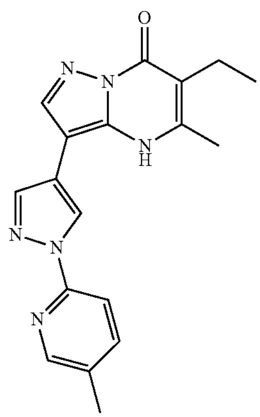 [SMILES: CCc1c(C)[nH]c2c(-c3cnn(-c4ccc(C)cn4)c3)cnn2c1=O] | 6-ethyl-5-methyl-3-[1-(5-methyl-2-pyridyl)pyrazol-4-yl]-4H-pyrazolo[1,5-a]pyrimidin-7-one | B | 335 | ¹H NMR (400 MHz, DMSO) δ 11.49-11.40 (s, 1H), 9.09-9.03 (d, J = 0.7 Hz, 1H), 8.37-8.32 (m, 1H), 8.21-8.15 (m, 2H), 7.91-7.80 (m, 2H), 2.51-2.49 (q, J = 7.4 Hz, 2H), 2.44 (s, 3H), 2.36 (s, 3H), 1.10-1.01 (t, J = 7.4 Hz, 3H) |
| 66 | 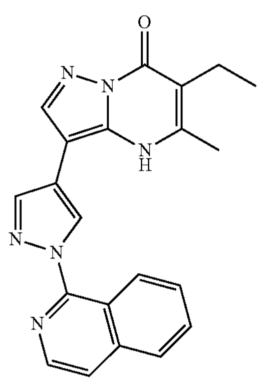 [SMILES: CCc1c(C)[nH]c2c(-c3cnn(-c4nccc5ccccc45)c3)cnn2c1=O] | 6-ethyl-3-(1-(isoquinolin-1-yl)-1H-pyrazol-4-yl)-5-methylpyrazolo[1,5-a]pyrimidin-7(4H)-one | A | 371 | ¹H NMR (400 MHz, DMSO-d₆): δ 11.52 (m, 1 H), 9.05 (s, 1 H), 8.97 (d, J = 8.7 Hz, 1 H), 8.43 (d, J = 5.5 Hz, 1 H), 8.32 (s, 1 H), 8.21 (d, J = 0.7 Hz, 1 H), 8.09 (d, J = 8.0 Hz, 1 H), 7.92 (d, J = 5.7 Hz, 1 H), 7.86 (m, 1 H), 7.79-7.65 (m, 1 H), 2.41 (s, 3 H), 1.03 (t, J = 7.3 Hz, 3 H). |
| 67 | 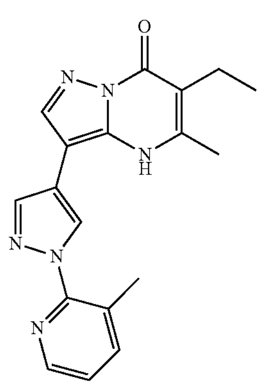 [SMILES: CCc1c(C)[nH]c2c(-c3cnn(-c4ncccc4C)c3)cnn2c1=O] | 6-ethyl-5-methyl-3-(1-(3-methylpyridin-2-yl)-1H-pyrazol-4-yl)pyrazolo[1,5-a]pyrimidin-7(4H)-one | A | 335 | ¹H NMR (400 MHz, DMSO-d₆): δ 11.38 (br. s., 1 H), 8.80 (s, 1 H), 8.38 (d, J = 3.0 Hz, 1 H), 8.14 (d, J = 1.1 Hz, 2 H), 7.87 (d, J = 6.9 Hz, 1 H), 7.37 (dd, J = 4.6, 7.6 Hz, 1 H), 2.50 (m, 2 H), 2.40 (s, 3 H), 1.02 (t, J = 7.4 Hz, 3 H). |

TABLE 1-continued

| Example | Structure | Name | Synth. Method | LCMS (ESI) m/z | NMR |
|---|---|---|---|---|---|
| 68 | 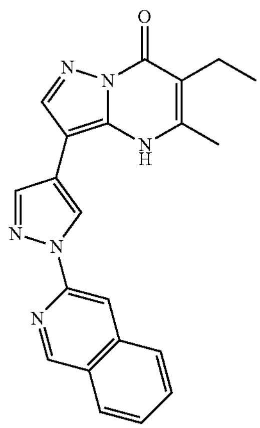 [SMILES: CCc1c(C)[nH]c2c(-c3cnn(-c4cc5ccccc5cn4)c3)cnn2c1=O] | 6-ethyl-3-(1-(isoquinolin-3-yl)-1H-pyrazol-4-yl)-5-methylpyrazolo[1,5-a]pyrimidin-7(4H)-one | A | 371 | $^1$H NMR (400 MHz, DMSO-$d_6$): δ 11.72-11.23 (bs, 1 H), 9.39-9.28 (m, 1 H), 9.20-9.01 (m, 1 H), 8.39-8.31 (m, 1 H), 8.28-8.22 (m, 1 H), 8.21-8.13 (m, 2 H), 8.12-8.03 (m, 1 H), 7.85-7.73 (m, 1 H), 7.67-7.54 (m, 1 H), 2.50 (m, 2 H), 2.42 (s, 3 H), 1.10-0.98 (m, 3 H). |
| 69 | 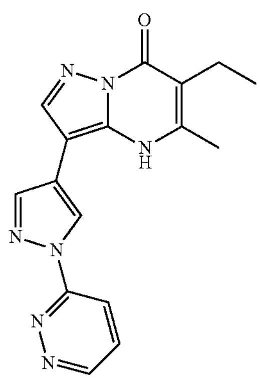 [SMILES: CCc1c(C)[nH]c2c(-c3cnn(-c4cccnn4)c3)cnn2c1=O] | 6-ethyl-5-methyl-3-(1-(pyridazin-3-yl)-1H-pyrazol-4-yl)pyrazolo[1,5-a]pyrimidin-7(4H)-one | A | 322 | $^1$H NMR (400 MHz, DMSO-$d_6$): δ 11.45 (bs, 1 H), 9.41 (s, 1 H), 9.20 (dd, J = 1.5, 4.7 Hz, 1 H), 8.34 (s, 1 H), 8.28-8.20 (m, 2 H), 7.90 (dd, J = 4.5, 8.8 Hz, 1 H), 2.50 (m, 2 H), 2.43 (s, 3 H), 1.03 (t, J = 7.3 Hz, 3 H). |
| 70 | 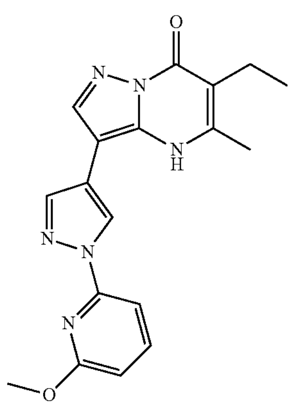 [SMILES: CCc1c(C)[nH]c2c(-c3cnn(-c4cccc(OC)n4)c3)cnn2c1=O] | 6-ethyl-3-(1-(6-methoxypyridin-2-yl)-1H-pyrazol-4-yl)-5-methylpyrazolo[1,5-a]pyrimidin-7(4H)-one | A | 351 | $^1$H NMR (400 MHz, DMSO-$d_6$): δ 11.53 (bs, 1 H), 8.90 (d, J = 0.7 Hz, 1 H), 8.17-8.04 (m, 1 H), 7.87 (t, J = 8.0 Hz, 2 H), 7.48 (d, J = 7.8 Hz, 1 H), 6.75 (d, J = 8.0 Hz, 1 H), 3.97 (s, 3 H), 2.50 (m, 2 H), 2.39 (s, 3 H), 1.08-0.93 (m, 3 H). |
| 71 | 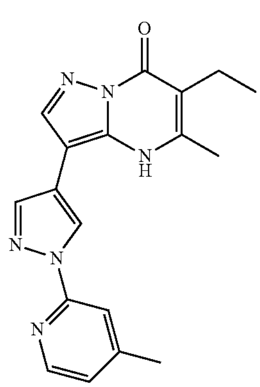 [SMILES: CCc1c(C)[nH]c2c(-c3cnn(-c4cc(C)ccn4)c3)cnn2c1=O] | 6-ethyl-5-methyl-3-(1-(4-methylpyridin-2-yl)-1H-pyrazol-4-yl)pyrazolo[1,5-a]pyrimidin-7(4H)-one | A | 335 | $^1$H NMR (400 MHz, DMSO-$d_6$): δ 11.45 (s, 1 H), 9.06 (s, 1 H), 8.34 (d, J = 5.0 Hz, 1 H), 8.18 (d, J = 1.8 Hz, 2 H), 7.80 (s, 1 H), 7.19 (d, J = 5.0 Hz, 1 H), 2.50 (m, 2 H), 2.41 (2 s, 6 H), 1.02 (t, J = 7.3 Hz, 3 H). |

TABLE 1-continued

| Example | Structure | Name | Synth. Method | LCMS (ESI) m/z | NMR |
|---|---|---|---|---|---|
| 72 | 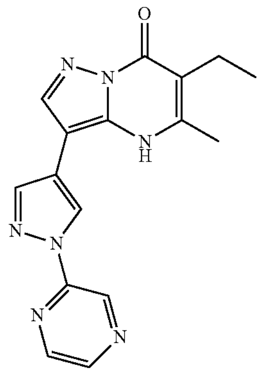 [SMILES: CCc1c(C)[nH]c2c(-c3cnn(-c4cnccn4)c3)cnn2c1=O] | 6-ethyl-5-methyl-3-(1-(pyrazin-2-yl)-1H-pyrazol-4-yl)pyrazolo[1,5-a]pyrimidin-7(4H)-one | A | 322 | $^1$H NMR (400 MHz, DMSO-d$_6$): δ 11.50 (m, 1 H), 9.25 (d, J = 1.6 Hz, 1 H), 9.11 (s, 1 H), 8.69-8.50 (m, 2 H), 8.31 (s, 1 H), 8.21 (s, 1 H), 2.50 (m, 2 H), 2.42 (s, 3 H), 1.02 (t, J = 7.4 Hz, 3 H). |
| 73 | 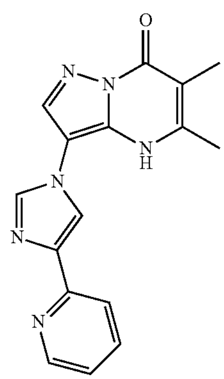 [SMILES: Cc1[nH]c2c(-n3cnc(-c4ccccn4)c3)cnn2c(=O)c1C] | 5,6-dimethyl-3-(4-(pyridin-2-yl)-1H-imidazol-1-yl)pyrazolo[1,5-a]pyrimidin-7(4H)-one | D | 307 | $^1$H NMR (300 MHz, DMSO-d$_6$): δ 12.19 (s, 1H), 8.51 (s, 1H), 8.1 (s, 1H), 7.93 (d, J = 6 Hz, 3H), 7.85 (d, J = 22.8 Hz, 1H), 7.22 (s, 1H), 2.31 (s, 3H), 1.99 (s, 3H). |
| 74 | 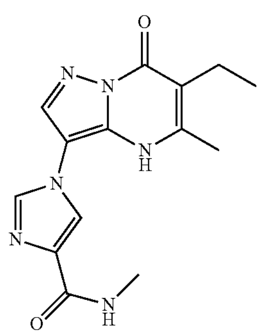 [SMILES: CCc1c(C)[nH]c2c(-n3cnc(C(=O)NC)c3)cnn2c1=O] | 1-(6-ethyl-5-methyl-7-oxo-4,7-dihydropyrazolo[1,5-a]pyrimidin-3-yl)-N-methyl-1H-imidazole-4-carboxamide | D | 301 | $^1$H NMR (300 MHz, DMSO): δ 8.13 (s, 1H), 8.04 (s, 1H), 7.63 (s, 1H), 2.83 (d, J = 4.8 Hz, 2H), 2.56 (m, 2H), 2.31 (s, 3H), 1.11 (m, 3H). |
| 75 | 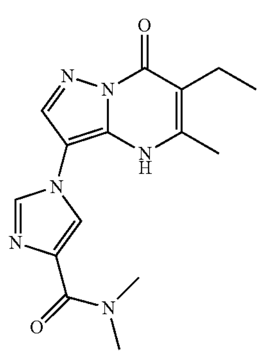 [SMILES: CCc1c(C)[nH]c2c(-n3cnc(C(=O)N(C)C)c3)cnn2c1=O] | 1-(6-ethyl-5-methyl-7-oxo-4,7-dihydropyrazolo[1,5-a]pyrimidin-3-yl)-N,N-dimethyl-1H-imidazole-4-carboxamide | D | 315 | $^1$H NMR (300 MHz, DMSO-6): δ 12.03 (s, 1H), 8.14-7.78 (m, 3H), 3.25 (s, 6H), 7.31-7.26 (m, 1H), 2.57-2.51 (m, 2H), 2.38 (s, 3H), 1.11 (s, J = 7.2 Hz, 3H). |

Example 76

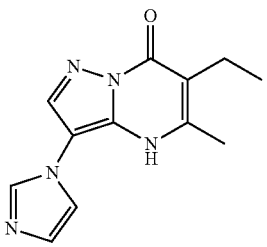

6-ethyl-3-(1H-imidazol-1-yl)-5-methylpyrazolo[1,5-a]pyrimidin-7(4H)-one

Step 1

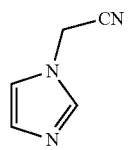

2-(1H-imidazol-1-yl)acetonitrile

To a solution of 1H-Imidazole (5 g, 73.5 mmol) in THF was added sodium hydride (1.8 g, 45 mmol) and stirred at room temperature for 0.5 hour before addition of then bromo-acetonitrile (8.8 g, 73.9 mmol) and stirring at room temperature for 2 hours. The reaction was quenched via the addition of water (50 mL) and saturated ammonium chloride (50 mL) solution and the mixture was extracted with ethyl acetate (100 mL×3). The combined organics layer was dried over anhydrous magnesium sulfate, filtered, and concentrated. The crude residue was purified on silica gel (petroleum ether:ethyl acetate=10:1) to afford 2-(1H-imidazol-1-yl)acetonitrile (4.6 g, 59%) as a yellow oil. LRMS m/z: 108 [M+H$^+$].

Step 2

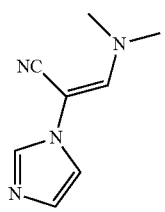

(E)-3-(dimethylamino)-2-(1H-imidazol-1-yl)acrylonitrile

A mixture of 2-(1H-imidazol-1-yl)acetonitrile (200 mg, 1.87 mmol) and N,N-dimethylformamide diethyl acetal (550 mg, 3.7 mmol) was heated to 90° C. in a microwave reactor for 15 minutes. The reaction was cooled to room temperature and the crude mixture was filtered through silica gel eluting with ethyl acetate (30 mL). The solvent was evaporated and the product was distilled to afford (E)-3-(dimethylamino)-2-(1H-imidazol-1-yl)acrylonitrile (150 mg, 49.5%).

Step 3

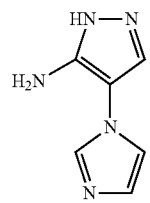 [SMILES: Nc1[nH]ncc1-n1ccnc1]

4-(1H-imidazol-1-yl)-1H-pyrazol-5-amine

To a solution of (E)-3-(dimethylamino)-2-(1H-imidazol-1-yl)acrylonitrile (100 mg, 0.6 mmol) in ethanol (20 mL) was added hydrazine hydrate (0.66 mmol) at room temperature. The reaction solution was cooled to 0° C. and the PH was adjusted to 4-5 by addition of HCl. The mixture was refluxed for 2 hours before cooling to room temperature and concentrating. The crude residue was purified on silica gel (petroleum ether:ethyl acetate=1:1) to afford 4-(1H-imidazol-1-yl)-1H-pyrazol-5-amine (50 mg, 54.4%).

Step 4

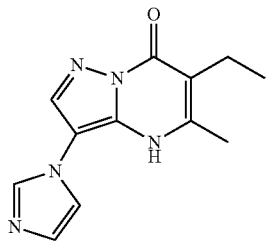 [SMILES: CCc1c(C)[nH]c2c(-n3ccnc3)cnn2c1=O]

6-ethyl-3-(1H-imidazol-1-yl)-5-methylpyrazolo[1,5-a]pyrimidin-7(4H)-one

To a solution of 4-(1H-imidazol-1-yl)-1H-pyrazol-5-amine (50 mg, 0.34 mmol) in acetic acid (10 mL) was added ethyl 2-ethyl-3-oxobutanoate (54 mg, 0.34 mmol) at room temperature before heating the solution to reflux for 2 h. The reaction was cooled to room temperature and concentrated. The crude residue was washed with methanol (5 mL) to afford 6-ethyl-3-(1H-imidazol-1-yl)-5-methylpyrazolo[1,5-a]pyrimidin-7(4H)-one (10 mg, 12%). $^1$H NMR (300 MHz, CD$_3$OD): δ 8.25 (s, 1H), 8.12 (s, 1H), 7.50 (s, 1H), 7.34 (s, 1H), 2.67 (q, J=7.8 Hz, 2H), 2.45 (s, 3H), 2.17 (t, J=7.5 Hz, 3H). LRMS m/z: 244 [M+H$^+$].

Using procedures similar to those described in Example 76, the following compounds were prepared.

| Example | Structure | Name | LCMS (ESI) m/z | NMR |
|---|---|---|---|---|
| 77 | 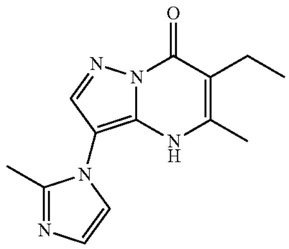 [SMILES: CCc1c(C)[nH]c2c(-n3ccnc3C)cnn2c1=O] | 6-ethyl-5-methyl-3-(2-methyl-1H-imidazol-1-yl)pyrazolo[1,5-a]pyrimidin-7(4H)-one | 258 | $^1$H NMR (300 MHz, CD$_3$OD): δ 7.90 (s, 1H), 7.05 (d, J = 1.8 Hz, 1H), 6.91 (d, J = 1.5 Hz, 1H), 2.54 (q, J = 7.5 Hz, 2H), 2.30 (s, 3H), 2.16 (s, 3H), 1.05 (t, J = 7.2 Hz, 3H). |
| 78 | 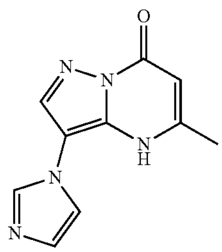 [SMILES: Cc1cc(=O)n2ncc(-n3ccnc3)c2[nH]1] | 3-(1H-imidazol-1-yl)-5-methylpyrazolo[1,5-a]pyrimidin-7(4H)-one | 216 | $^1$H NMR (300 MHz, DMSO-d$_6$): δ 12.80 (br, 1H), 9.38 (s, 1H), 8.25 (s, 1H), 7.93 (d, J = 3.6 Hz, 1H), 7.87 (d, J = 3.6 Hz, 1H), 5.79 (s, 1H), 2.33 (s, 3H). |
| 79 | 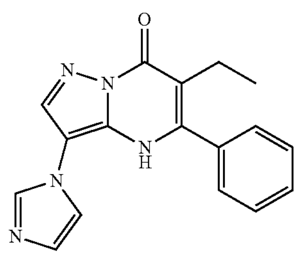 [SMILES: CCc1c(-c2ccccc2)[nH]c2c(-n3ccnc3)cnn2c1=O] | 6-ethyl-3-(1H-imidazol-1-yl)-5-phenylpyrazolo[1,5-a]pyrimidin-7(4H)-one | 306 | $^1$H NMR (300 MHz, DMSO-d6): δ 12.80 (s, 1H), 7.93 (s, 2H), 7.51 (d, 5H), 7.41 (s, 1H), 7.10 (s, 1H), 2.22 (d, 2H), 0.98 (s, 3H). |
| 80 | 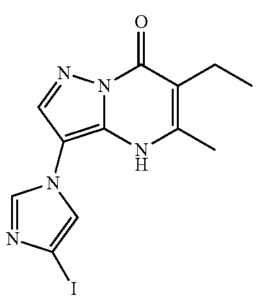 [SMILES: CCc1c(C)[nH]c2c(-n3cnc(I)c3)cnn2c1=O] | 6-ethyl-3-(4-iodo-1H-imidazol-1-yl)-5-methylpyrazolo[1,5-a]pyrimidin-7(4H)-one | 370 | $^1$H NMR (400 MHz, DMSO-d6): δ 12.10 (br. s., 1H), 8.04 (s, 1H), 7.79 (d, J = 1.37 Hz, 1H), 7.57 (d, J = 1.37 Hz, 1H), 2.50 (m, 2H), 2.17-2.36 (m, 3H), 1.02 (t, J = 7.21, 3H). |
| 81 | 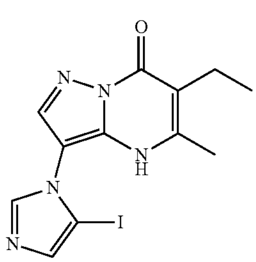 [SMILES: CCc1c(C)[nH]c2c(-n3cncc3I)cnn2c1=O] | 6-ethyl-3-(5-iodo-1H-imidazol-1-yl)-5-methylpyrazolo[1,5-a]pyrimidin-7(4H)-one | 370 | $^1$H NMR (400 MHz, DMSO-d6): δ 12.00-12.33 (m, 1H), 7.93 (br. s., 2H), 7.17 (s, 1H), 2.50 (m, 2H), 2.27 (s, 3H), 1.02 (t, J = 7.32 Hz, 3H). |
| 82 | 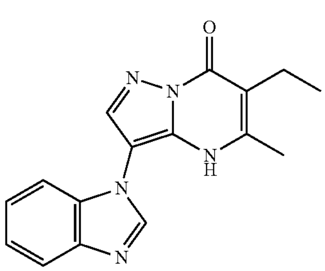 [SMILES: CCc1c(C)[nH]c2c(-n3cnc4ccccc43)cnn2c1=O] | 3-(1H-benzo[d]imidazol-1-yl)-6-ethyl-5-methylpyrazolo[1,5-a]pyrimidin-7(4H)-one | 294 | $^1$H NMR (400 MHz, DMSO-d6): δ 12.13 (s, 1H), 8.32 (s, 1H), 8.15 (s, 1H), 7.64-7.82 (m, 1H), 7.15-7.34 (m, 3H), 2.50 (M + 1), 2.27 (s, 3H), 1.05 (t, J = 7.32 Hz, 3H). |

Example 83

Assessment of Inhibitory Effect of Test Compounds on KDM5A Demethylase Activity KDM5A Demethylase Assay (MassSpec Assay-A)

Full length recombinant Flag tagged KDM5A protein was purified from SD insect cells. The demethylation reaction buffer contained 50 mM TrisCl pH 7.4, 0.01% Triton X-100, 0.025 mg/mL BSA, 1 mM ascorbate (Cat# A4034, Sigma Aldrich), 2 mM TCEP (Cat# D9779, Sigma Aldrich), 2.0 µM α-ketoglutarate (# K2010, Sigma Aldrich) and 50 µM $Fe_2(NH_4)_2(SO_4)_2$ (Cat# F1543, Sigma Aldrich). In a 25 µL demethylation reaction system, 20 nM recombinant KDM5A and was incubated with compounds for 10 minutes in the above buffer, and then 2.0 α-ketoglutarate (# K2010, Sigma Aldrich), 4.0 µM biotinylated H3K9me1 peptide (1-21 aa), and $Fe_2(NH_4)_2(SO_4)_2$ were added to initiate the reaction. (All reagent concentrations are final reagent concentrations.) Reactions were incubated for 30 minutes at room temperature, and then quenched by addition of an equal volume of 1% formic acid. After termination, plates were sealed and frozen at −80° C. for analysis.

KDM5A Demethylase Assays (TR-FRET Assay-B)

Full length recombinant Flag tagged KDM5A protein was purified from Sf9 insect cells. The demethylation reaction buffer contained 50 mM TrisCl pH 7.4, 0.01% Triton X-100, 0.025 mg/mL BSA, 1 mM ascorbate, 2 mM TCEP, 3.0 µM α-ketoglutarate, and 50 µM $Fe_2(NH_4)_2(SO_4)_2$. In a 10 µL demethylation reaction system, 2 nM recombinant KDM5A and was incubated with compounds for 15 minutes in the above buffer ($V_t$ 5 uL) in a 384 well Proxi Plate (Perkin Elmer Corp.), and then 0.1 µM biotinylated H3K9me1 peptide (1-21 aa, New England Peptide, $V_t$ 5 uL) was added to initiate the reaction ($V_t$ 10 uL). (All protein/reagent concentrations are final concentrations.) Reactions were incubated for 25 minutes at room temperature, and then quenched by addition of 5 uL of detection reagents (buffer as above with addition of 0.3 mM EDTA, 150 mM NaCl, 150 nM SA-SurelightAPC and 1.5 nM Eu(W1024)-K3K4Me1/2 antibody (TR-FRET reagents both Perkin-Elmer)). After a one hour incubation assays were read on a Perkin-Elmer Envision equipped with a laser source and appropriate filters. $IC_{50}$s were calculated using standard dose-response equations and relative to a Max (no inhibition) and Min (no enzyme or quenched enzyme) controls.

KDM5A Demethylase Assays (TR-FRET Assay-C)

Full length recombinant Flag tagged KDM5A protein was purified from Sf9 insect cells. The demethylation reaction buffer contained 50 mM HEPES pH 7.0, 0.01% Triton X-100, 0.5 mM ascorbate, 2 mM DTT, 1 µM α-ketoglutarate, and 100 µM $Fe_2(NH_4)_2(SO_4)_2$. In a 10 µL demethylation reaction system, 2 nM recombinant KDM5A was added to compounds in the above buffer ($V_t$ 5 uL) in a 384 well Proxi Plate (Perkin Elmer Corp.) and then 0.1 µM biotinylated H3K9me1 peptide (1-21 aa, New England Peptide, $V_t$ 5 uL) was added to initiate the reaction ($V_t$ 10 uL). (All protein/reagent concentrations are final concentrations.) Reactions were incubated for 30 minutes at room temperature, and then quenched by addition of 5 uL stop buffer (3 mM EDTA, 50 mM TrisCl pH 7.5, 0.01% Triton X-100, 0.01 mg/mL BSA) followed by addition of 5 uL of detection reagents (buffer as above without EDTA but with addition of 200 nM SA-XL665 (CisBio) and 2 nM Eu(W1024)-anti-H3K4Me1-2 antibody (PerkinElmer)). After a 30 minute incubation assays were read on a Perkin-Elmer Envision equipped with appropriate filters. $IC_{50}$s were calculated using standard dose-response equations and relative to a Max (no inhibition) and Min (no enzyme or quenched enzyme) controls.

Data for representative compounds from Example 83 is provided in the following table (in µM).

| Example | Structure | A KDM5A MS (IC50) | B KDM5A HTRF (IC50) | C KDM5A HTRF (IC50) |
|---|---|---|---|---|
| 1 | 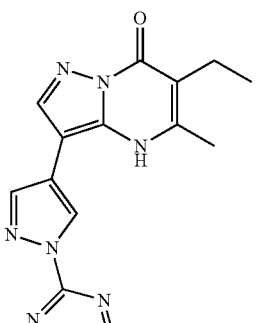 | 0.0263 | | |

-continued
| Example | Structure | A KDM5A MS (IC50) | B KDM5A HTRF (IC50) | C KDM5A HTRF (IC50) |
|---|---|---|---|---|
| 2 | 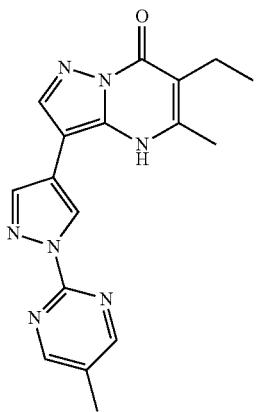 [SMILES: CCc1c(C)[nH]c2c(-c3cnn(-c4ncc(C)cn4)c3)cnn2c1=O] | | 0.0161 | |
| 3 | 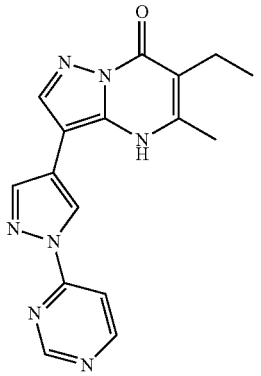 [SMILES: CCc1c(C)[nH]c2c(-c3cnn(-c4ccncn4)c3)cnn2c1=O] | | 0.158 | |
| 4 | 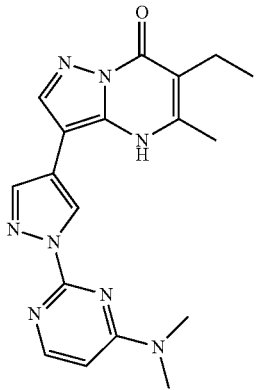 [SMILES: CCc1c(C)[nH]c2c(-c3cnn(-c4nccc(N(C)C)n4)c3)cnn2c1=O] | | 0.047 | |

-continued

| Example | Structure | A KDM5A MS (IC50) | B KDM5A HTRF (IC50) | C KDM5A HTRF (IC50) |
|---|---|---|---|---|
| 5 | 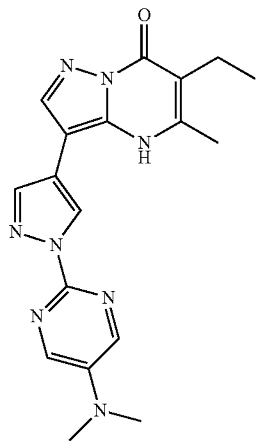 [SMILES: CCc1c(C)[nH]c2c(-c3cnn(-c4ncc(N(C)C)cn4)c3)cnn2c1=O] | | 0.0603 | |
| 6 | 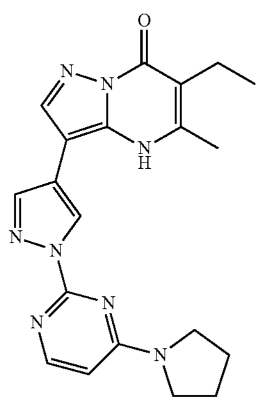 [SMILES: CCc1c(C)[nH]c2c(-c3cnn(-c4nccc(N5CCCC5)n4)c3)cnn2c1=O] | | 0.0529 | |
| 7 | 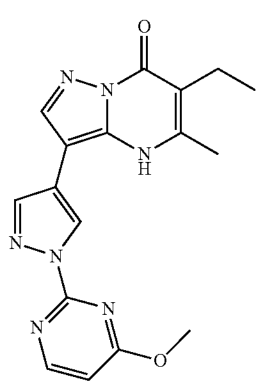 [SMILES: CCc1c(C)[nH]c2c(-c3cnn(-c4nccc(OC)n4)c3)cnn2c1=O] | | 0.0086 | |

-continued

| Example | Structure | A KDM5A MS (IC50) | B KDM5A HTRF (IC50) | C KDM5A HTRF (IC50) |
|---------|-----------|-------------------|---------------------|---------------------|
| 8 | 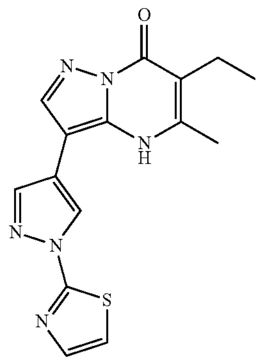 [SMILES: CCc1c(C)[nH]c2c(-c3cnn(-c4nccs4)c3)cnn2c1=O] | | 0.136 | |
| 9 | 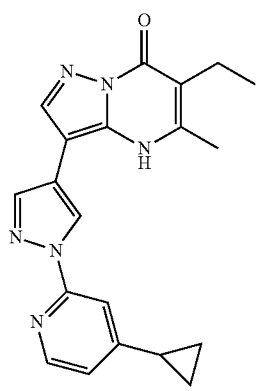 [SMILES: CCc1c(C)[nH]c2c(-c3cnn(-c4cc(C5CC5)ccn4)c3)cnn2c1=O] | | 0.0166 | |
| 10 | 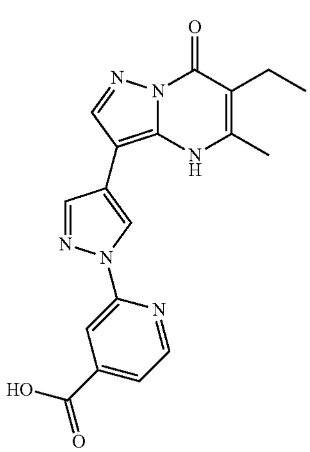 [SMILES: CCc1c(C)[nH]c2c(-c3cnn(-c4cc(C(=O)O)ccn4)c3)cnn2c1=O] | | 0.201 | |

-continued

| Example | Structure | A KDM5A MS (IC50) | B KDM5A HTRF (IC50) | C KDM5A HTRF (IC50) |
|---------|-----------|-------------------|---------------------|---------------------|
| 11 | 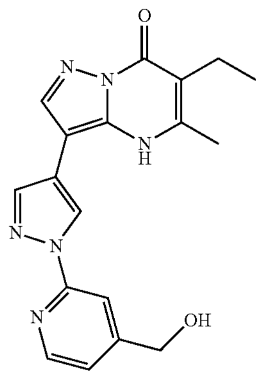 [SMILES: CCc1c(C)[nH]c2c(-c3cnn(-c4cc(CO)ccn4)c3)cnn2c1=O] | | 0.0023 | |
| 12 | 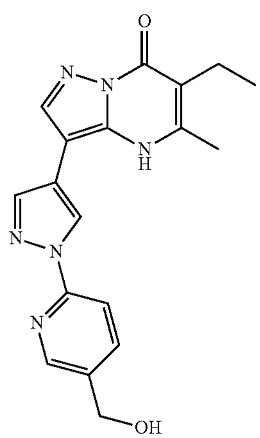 [SMILES: CCc1c(C)[nH]c2c(-c3cnn(-c4ccc(CO)cn4)c3)cnn2c1=O] | | 0.0313 | |
| 13 | 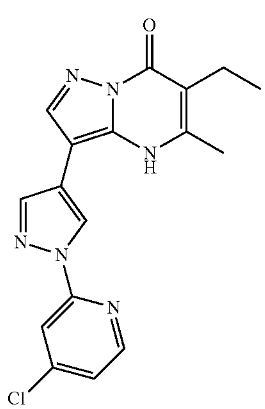 [SMILES: CCc1c(C)[nH]c2c(-c3cnn(-c4cc(Cl)ccn4)c3)cnn2c1=O] | | 0.0661 | |

-continued
| Example | Structure | A KDM5A MS (IC50) | B KDM5A HTRF (IC50) | C KDM5A HTRF (IC50) |
|---|---|---|---|---|
| 14 | 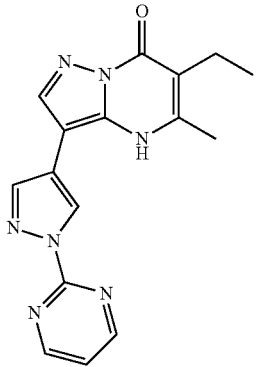 [SMILES: CCc1c(C)[nH]c2c(-c3cnn(-c4ncccn4)c3)cnn2c1=O] | | 0.0165 | |
| 15 | 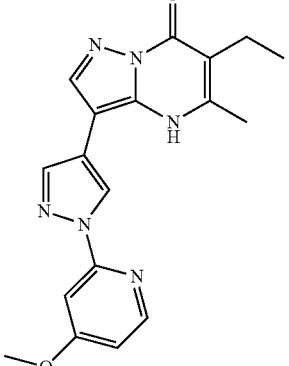 | | 0.0661 | |
| 16 | 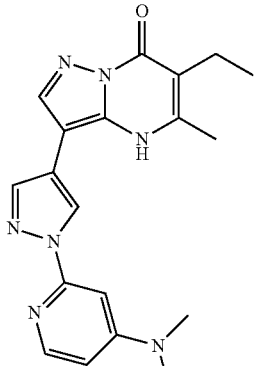 | | 0.406 | |
| 17 | 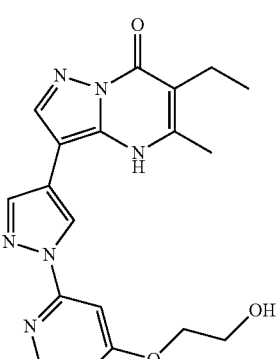 | | 0.0141 | |

-continued
| Example | Structure | A KDM5A MS (IC50) | B KDM5A HTRF (IC50) | C KDM5A HTRF (IC50) |
|---|---|---|---|---|
| 18 | 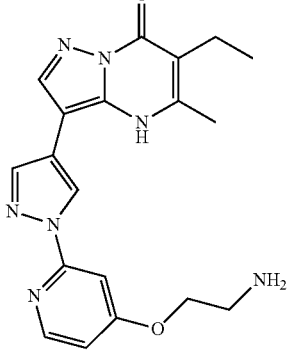 | | 0.0098 | |
| 19 | 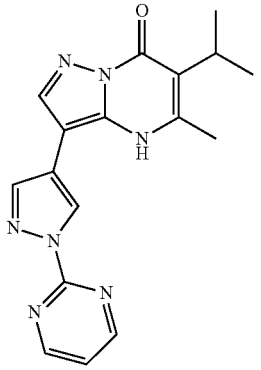 [SMILES: Cc1[nH]c2c(-c3cnn(-c4ncccn4)c3)cnn2c(=O)c1C(C)C] | | 0.0057 | |
| 20 | 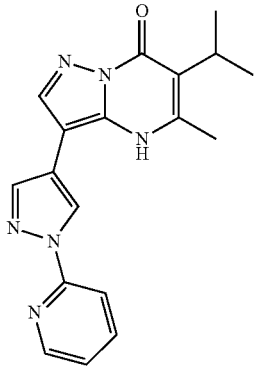 [SMILES: Cc1[nH]c2c(-c3cnn(-c4ccccn4)c3)cnn2c(=O)c1C(C)C] | | 0.0083 | |

-continued

| Example | Structure | A KDM5A MS (IC50) | B KDM5A HTRF (IC50) | C KDM5A HTRF (IC50) |
|---------|-----------|-------------------|---------------------|---------------------|
| 21 | 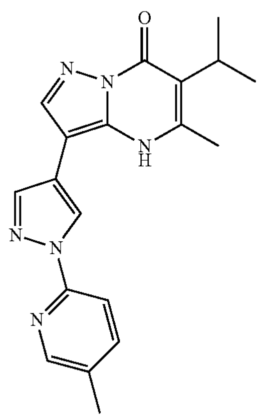 [SMILES: Cc1ccc(-n2cc(-c3cnn4c(=O)c(C(C)C)c(C)[nH]c34)cn2)nc1] | | 0.0091 | |
| 22 | 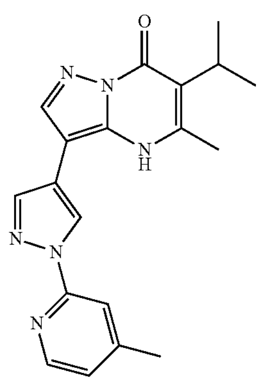 [SMILES: Cc1ccnc(-n2cc(-c3cnn4c(=O)c(C(C)C)c(C)[nH]c34)cn2)c1] | | 0.0236 | |
| 23 | 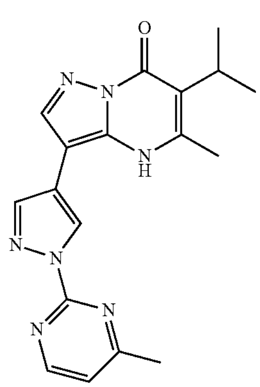 [SMILES: Cc1ccnc(-n2cc(-c3cnn4c(=O)c(C(C)C)c(C)[nH]c34)cn2)n1] | | 0.0543 | |

-continued

| Example | Structure | A KDM5A MS (IC50) | B KDM5A HTRF (IC50) | C KDM5A HTRF (IC50) |
|---|---|---|---|---|
| 24 | 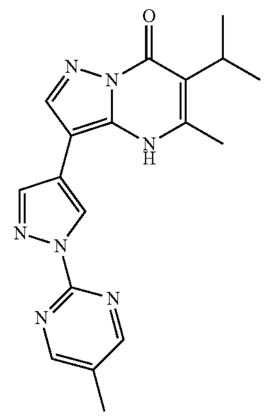 [SMILES: Cc1cnc(-n2cc(-c3cnn4c(=O)c(C(C)C)c(C)[nH]c34)cn2)nc1] | | 0.0166 | |
| 25 | 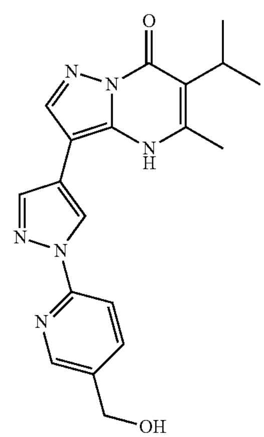 [SMILES: Cc1[nH]c2c(-c3cnn(-c4ccc(CO)cn4)c3)cnn2c(=O)c1C(C)C] | | 0.0066 | |
| 27 | 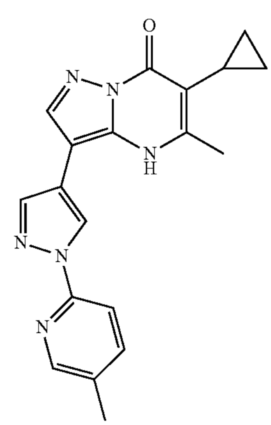 [SMILES: Cc1ccc(-n2cc(-c3cnn4c(=O)c(C5CC5)c(C)[nH]c34)cn2)nc1] | | 0.0332 | |

-continued

| Example | Structure | A KDM5A MS (IC50) | B KDM5A HTRF (IC50) | C KDM5A HTRF (IC50) |
|---|---|---|---|---|
| 28 | 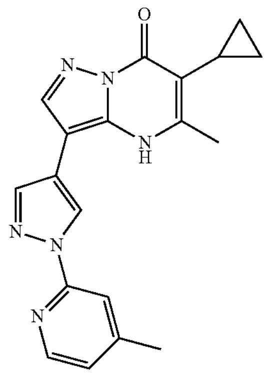 [SMILES: Cc1ccnc(-n2cc(-c3cnn4c(=O)c(C5CC5)c(C)[nH]c34)cn2)c1] | | 0.0134 | |
| 29 | 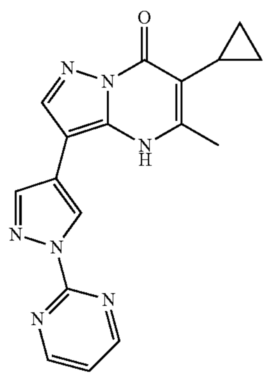 [SMILES: Cc1[nH]c2c(-c3cnn(-c4ncccn4)c3)cnn2c(=O)c1C1CC1] | | 0.0185 | |
| 30 | 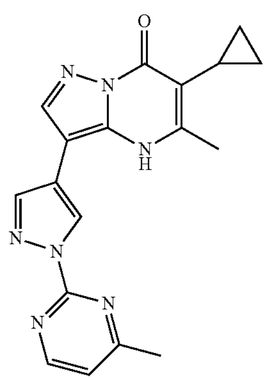 [SMILES: Cc1ccnc(-n2cc(-c3cnn4c(=O)c(C5CC5)c(C)[nH]c34)cn2)n1] | | 0.0048 | |
| 31 | 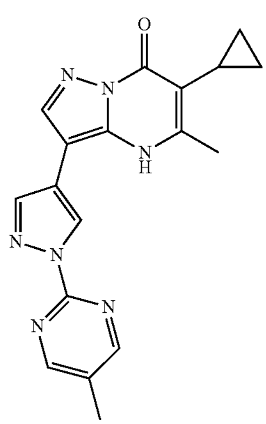 [SMILES: Cc1cnc(-n2cc(-c3cnn4c(=O)c(C5CC5)c(C)[nH]c34)cn2)nc1] | | 0.0487 | |

-continued
| Example | Structure | A KDM5A MS (IC50) | B KDM5A HTRF (IC50) | C KDM5A HTRF (IC50) |
|---|---|---|---|---|
| 32 | 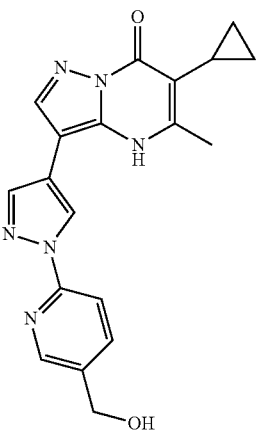 [SMILES: Cc1[nH]c2c(-c3cnn(-c4ccc(CO)cn4)c3)cnn2c(=O)c1C1CC1] | | 0.0079 | |
| 33 | 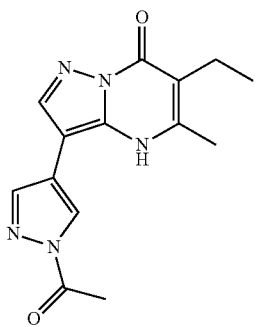 [SMILES: CCc1c(C)[nH]c2c(-c3cnn(C(C)=O)c3)cnn2c1=O] | | 0.196 | |
| 34 | 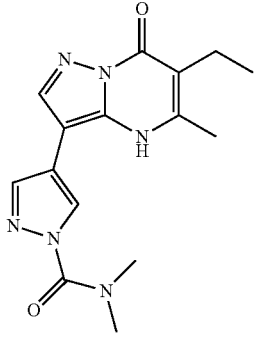 [SMILES: CCc1c(C)[nH]c2c(-c3cnn(C(=O)N(C)C)c3)cnn2c1=O] | | 4.18 | |
| 35 | 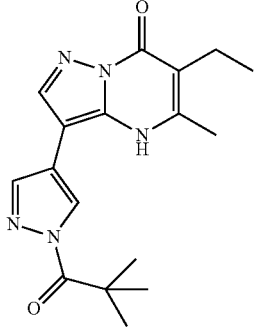 [SMILES: CCc1c(C)[nH]c2c(-c3cnn(C(=O)C(C)(C)C)c3)cnn2c1=O] | | 0.543 | |

-continued
| Example | Structure | A KDM5A MS (IC50) | B KDM5A HTRF (IC50) | C KDM5A HTRF (IC50) |
|---|---|---|---|---|
| 36 | 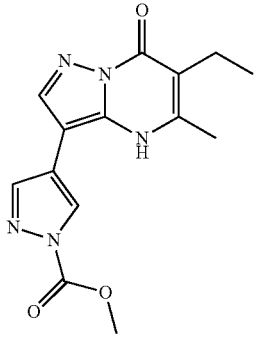 [SMILES: CCc1c(C)[nH]c2c(-c3cnn(C(=O)OC)c3)cnn2c1=O] | | 1.0 | |
| 37 | 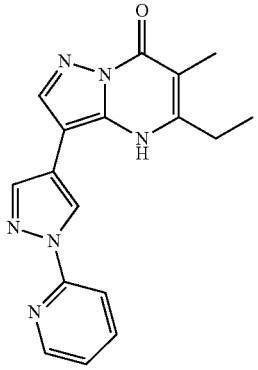 [SMILES: CCc1[nH]c2c(-c3cnn(-c4ccccn4)c3)cnn2c(=O)c1C] | | 0.335 | |
| 38 | 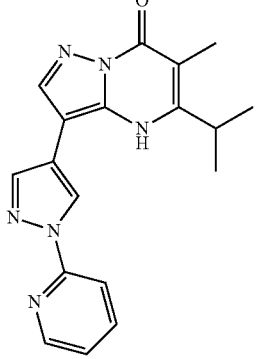 | | 1.0 | |
| 39 | 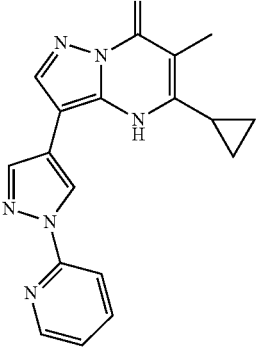 | | 0.624 | |

-continued

| Example | Structure | A KDM5A MS (IC50) | B KDM5A HTRF (IC50) | C KDM5A HTRF (IC50) |
|---------|-----------|-------------------|---------------------|---------------------|
| 40 | 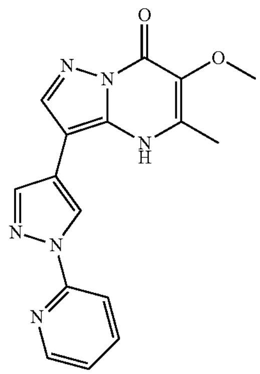 [SMILES: COc1c(C)[nH]c2c(-c3cnn(-c4ccccn4)c3)cnn2c1=O] | | 0.101 | |
| 41 | 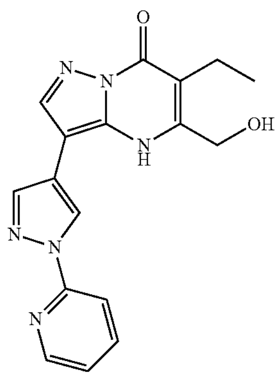 [SMILES: CCc1c(CO)[nH]c2c(-c3cnn(-c4ccccn4)c3)cnn2c1=O] | | 0.0041 | |
| 42 | 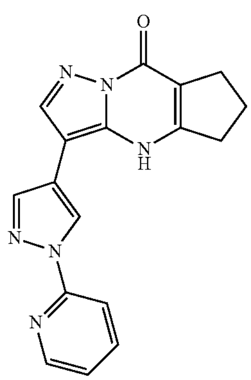 [SMILES: O=c1c2c([nH]c3c(-c4cnn(-c5ccccn5)c4)cnn13)CCC2] | | 0.0322 | |
| 43 | 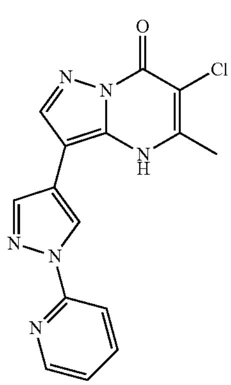 [SMILES: Cc1[nH]c2c(-c3cnn(-c4ccccn4)c3)cnn2c(=O)c1Cl] | | 0.0605 | |

| Example | Structure | A KDM5A MS (IC50) | B KDM5A HTRF (IC50) | C KDM5A HTRF (IC50) |
|---|---|---|---|---|
| 45 | 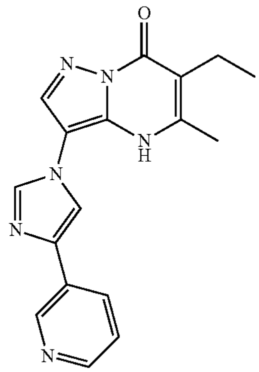 [SMILES: CCc1c(C)[nH]c2c(-n3cnc(-c4cccnc4)c3)cnn2c1=O] | 6.32 | | |
| 46 | 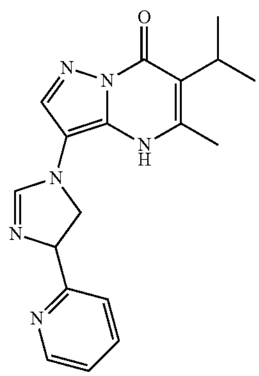 [SMILES: Cc1[nH]c2c(N3C=NC(c4ccccn4)C3)cnn2c(=O)c1C(C)C] | | | 0.0234 |
| 47 | 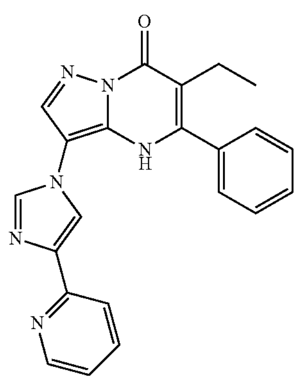 [SMILES: CCc1c(-c2ccccc2)[nH]c2c(-n3cnc(-c4ccccn4)c3)cnn2c1=O] | 0.574 | | |
| 48 | 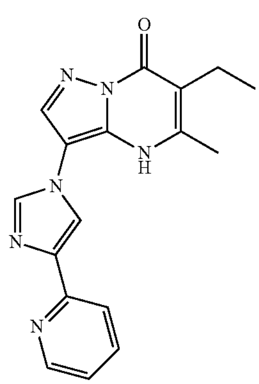 [SMILES: CCc1c(C)[nH]c2c(-n3cnc(-c4ccccn4)c3)cnn2c1=O] | 0.0705 | | |

-continued

| Example | Structure | A KDM5A MS (IC50) | B KDM5A HTRF (IC50) | C KDM5A HTRF (IC50) |
|---|---|---|---|---|
| 49 | 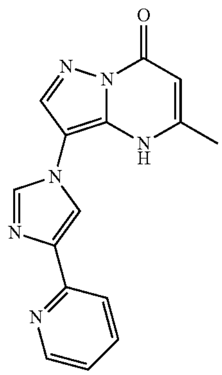 [SMILES: Cc1cc(=O)n2ncc(-n3cnc(-c4ccccn4)c3)c2[nH]1] | | 0.0437 | |
| 51 | 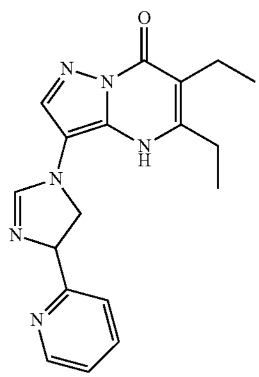 [SMILES: CCc1[nH]c2c(N3C=NC(c4ccccn4)C3)cnn2c(=O)c1CC] | | 0.0708 | |
| 52 | 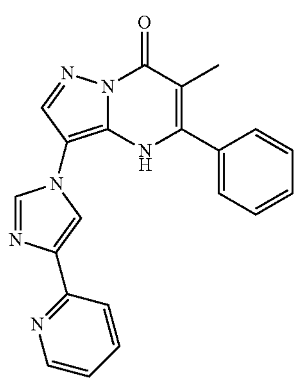 [SMILES: Cc1c(-c2ccccc2)[nH]c2c(-n3cnc(-c4ccccn4)c3)cnn2c1=O] | | 0.47 | |
| 53 | 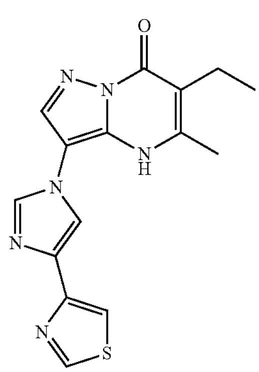 [SMILES: CCc1c(C)[nH]c2c(-n3cnc(-c4cscn4)c3)cnn2c1=O] | | 0.453 | |

|  | | A KDM5A MS (IC50) | B KDM5A HTRF (IC50) | C KDM5A HTRF (IC50) |
|---|---|---|---|---|
| Example | Structure | | | |
| 54 | | 0.538 | | |
| 55 | | 0.0945 | | |
| 56 | | 0.276 | | |
| 57 | | 0.268 | | |

-continued

| Example | Structure | A KDM5A MS (IC50) | B KDM5A HTRF (IC50) | C KDM5A HTRF (IC50) |
|---------|-----------|-------------------|---------------------|---------------------|
| 58 | 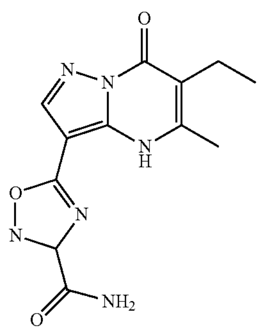 [SMILES: CCc1c(C)[nH]c2c(C3=NC(C(N)=O)NO3)cnn2c1=O] | 0.332 | | |
| 59 | 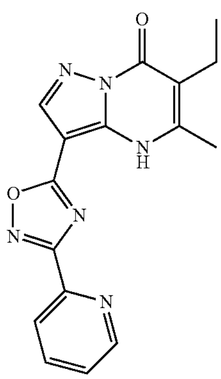 [SMILES: CCc1c(C)[nH]c2c(-c3nc(-c4ccccn4)no3)cnn2c1=O] | 0.518 | | |
| 60 | 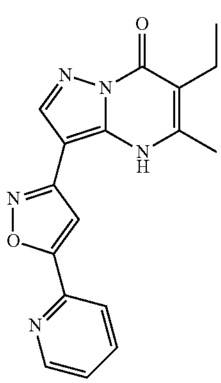 [SMILES: CCc1c(C)[nH]c2c(-c3cc(-c4ccccn4)on3)cnn2c1=O] | 4.0 | | |
| 61 | 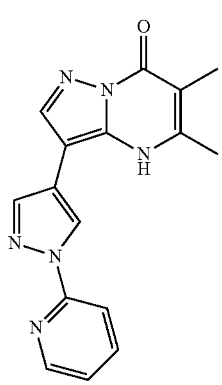 [SMILES: Cc1[nH]c2c(-c3cnn(-c4ccccn4)c3)cnn2c(=O)c1C] | 0.0661 | | |

-continued

| Example | Structure | A KDM5A MS (IC50) | B KDM5A HTRF (IC50) | C KDM5A HTRF (IC50) |
|---|---|---|---|---|
| 62 | 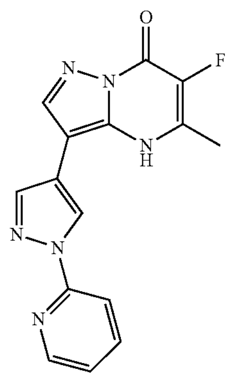 [SMILES: Cc1[nH]c2c(-c3cnn(-c4ccccn4)c3)cnn2c(=O)c1F] | | 0.212 | |
| 63 | 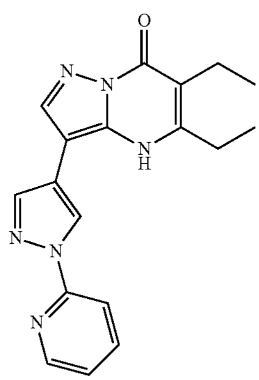 [SMILES: CCc1[nH]c2c(-c3cnn(-c4ccccn4)c3)cnn2c(=O)c1CC] | | 0.169 | |
| 64 | 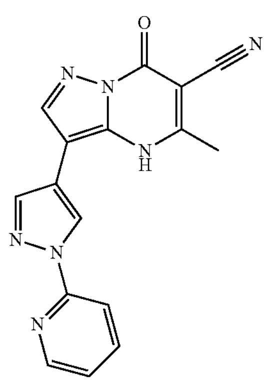 [SMILES: Cc1[nH]c2c(-c3cnn(-c4ccccn4)c3)cnn2c(=O)c1C#N] | | 0.83 | |
| 65 | 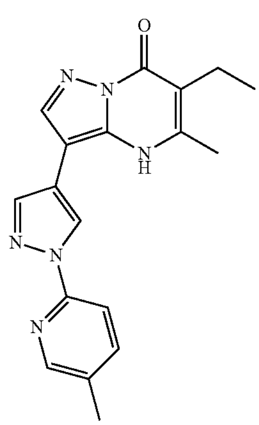 [SMILES: CCc1c(C)[nH]c2c(-c3cnn(-c4ccc(C)cn4)c3)cnn2c1=O] | | 0.0051 | |

-continued

| Example | Structure | A KDM5A MS (IC50) | B KDM5A HTRF (IC50) | C KDM5A HTRF (IC50) |
|---|---|---|---|---|
| 66 | 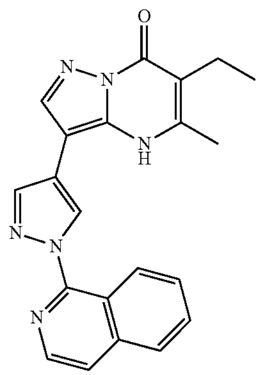 [SMILES: CCc1c(C)[nH]c2c(-c3cnn(-c4nccc5ccccc45)c3)cnn2c1=O] | 0.861 | | |
| 67 | 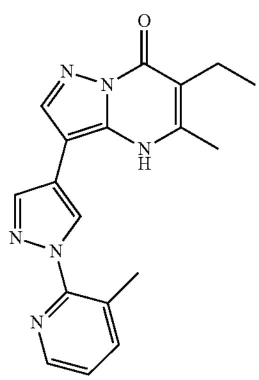 [SMILES: CCc1c(C)[nH]c2c(-c3cnn(-c4ncccc4C)c3)cnn2c1=O] | 0.363 | | |
| 68 | 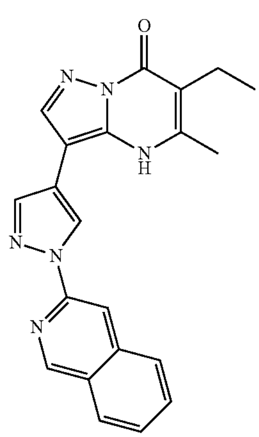 [SMILES: CCc1c(C)[nH]c2c(-c3cnn(-c4cc5ccccc5cn4)c3)cnn2c1=O] | 0.0369 | | |

-continued

| Example | Structure | A KDM5A MS (IC50) | B KDM5A HTRF (IC50) | C KDM5A HTRF (IC50) |
|---|---|---|---|---|
| 69 | 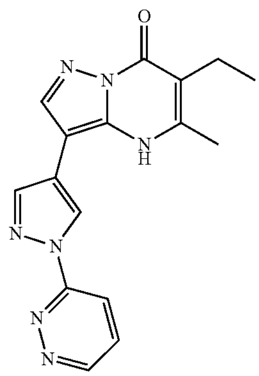 [SMILES: CCc1c(C)[nH]c2c(-c3cnn(-c4cccnn4)c3)cnn2c1=O] | 0.233 | | |
| 70 | 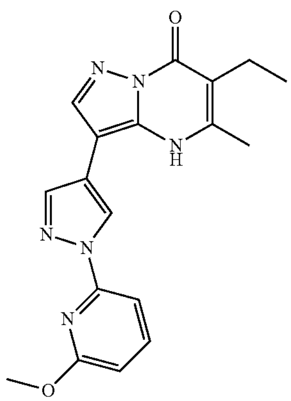 [SMILES: CCc1c(C)[nH]c2c(-c3cnn(-c4cccc(OC)n4)c3)cnn2c1=O] | 3.73 | | |
| 71 | 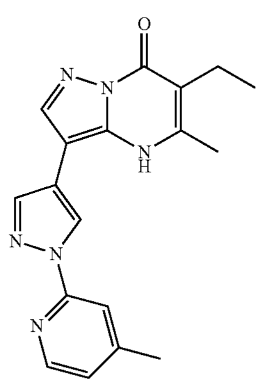 [SMILES: CCc1c(C)[nH]c2c(-c3cnn(-c4cc(C)ccn4)c3)cnn2c1=O] | 0.0263 | | |
| 72 | 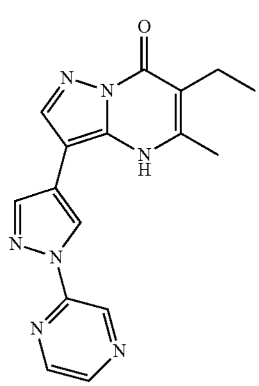 [SMILES: CCc1c(C)[nH]c2c(-c3cnn(-c4cnccn4)c3)cnn2c1=O] | 0.076 | | |

-continued
| Example | Structure | A KDM5A MS (IC50) | B KDM5A HTRF (IC50) | C KDM5A HTRF (IC50) |
|---|---|---|---|---|
| 73 | 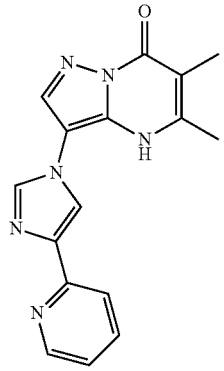 | 0.0537 | | |
| 74 | 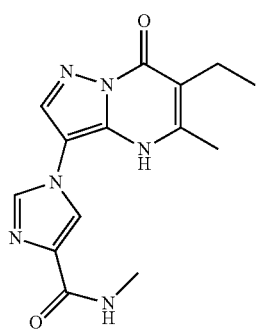 [SMILES: CCc1c(C)[nH]c2c(-n3cnc(C(=O)NC)c3)cnn2c1=O] | 0.996 | | |
| 75 | 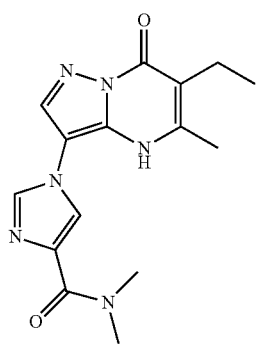 [SMILES: CCc1c(C)[nH]c2c(-n3cnc(C(=O)N(C)C)c3)cnn2c1=O] | 0.178 | | |
| 77 | 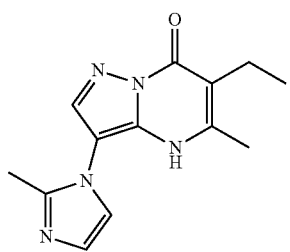 [SMILES: CCc1c(C)[nH]c2c(-n3ccnc3C)cnn2c1=O] | 3.38 | | |

| Example | Structure | A KDM5A MS (IC50) | B KDM5A HTRF (IC50) | C KDM5A HTRF (IC50) |
|---|---|---|---|---|
| 79 | 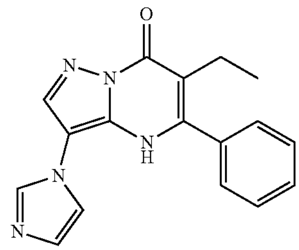 [SMILES: CCc1c(-c2ccccc2)[nH]c2c(-n3ccnc3)cnn2c1=O] | 43.2 | | |
| 80 | 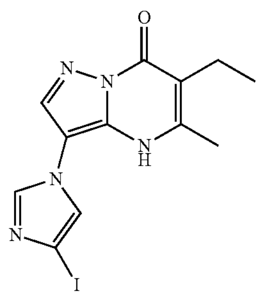 [SMILES: CCc1c(C)[nH]c2c(-n3cnc(I)c3)cnn2c1=O] | 29.4 | | |
| 81 | 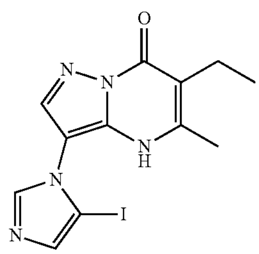 [SMILES: CCc1c(C)[nH]c2c(-n3cncc3I)cnn2c1=O] | 3.05 | | |
| 82 | 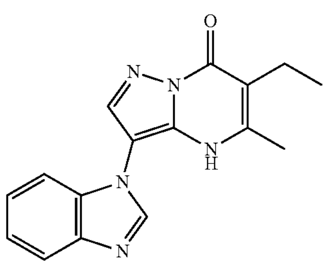 [SMILES: CCc1c(C)[nH]c2c(-n3cnc4ccccc43)cnn2c1=O] | 80.0 | | |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I):

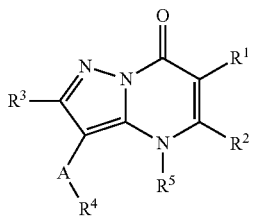

I wherein:

$R^1$ and $R^2$ are each independently H, $C_{1-12}$alkyl, $C_{2-12}$alkenyl, $C_{2-12}$alkynyl, carbocyclyl, heterocyclyl, halo, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —C=$NOR^a$, —$C(=N(R^a))N(R^a)_2$, —$OC(O)R^a$, or —$OC(O)N(R^a)_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups $R^x$; and wherein $R^1$ and $R^2$ are not each H; or $R^1$ and $R^2$ taken together with the atoms to which they are attached form a 4, 5, 6, 7, or 8 membered carbocyclyl, which carbocyclyl is optionally substituted with one or more groups $R^x$;

$R^3$ is H, $C_{1-6}$alkyl, trifluoromethyl, 3-6 membered carbocyclyl, 3-6 membered heterocyclyl, halo, —OR$^f$, —SR$^f$, —N(R$^f$)$_2$, —CN, or —NO$_2$, wherein said alkyl, carbocyclyl and heterocyclyl are optionally substituted with one or more groups independently selected from oxo, halo, $C_{1-3}$alkoxy and $C_{1-3}$alkyl;

$R^4$ is a pyrimidine, thiazole, pyridine, isoquinoline, or pyridazine ring, which ring is optionally substituted with one or more groups independently selected from $C_{1-6}$alkyl, carbocyclyl, —F, —Cl, —Br, —I, —N(R$^v$)$_2$, —O—R$^v$, and —C(O)—O—R$^v$;

$R^5$ is H, $C_{1-12}$alkyl, $C_{2-12}$alkenyl, $C_{2-12}$alkynyl, carbocyclyl, and heterocyclyl, wherein each $C_{1-12}$alkyl, $C_{2-12}$alkenyl, $C_{2-12}$alkynyl, carbocyclyl, and heterocyclyl is optionally substituted with one or more groups independently selected from oxo, $C_{1-12}$ alkyl, $C_{1-12}$haloalkyl, carbocyclyl, heterocyclyl, halo, —CN, —NO$_2$, —NR$^m$R$^m$, —OR$^m$, —C(=O)OR$^m$, and —OC(=O)R$^m$; or $R^5$ and $R^2$ taken together with the atoms to which they are attached form a heterocyclyl;

each $R^a$ is independently selected from H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups $R^x$;

each $R^f$ is independently selected from H, $C_{1-3}$ alkyl, trifluoromethyl, 3-6 membered carbocyclyl, and 3-6 membered heterocyclyl; or two $R^f$ groups together with the nitrogen to which they are attached form a 3-6 membered heterocycle;

each $R^g$ is independently selected from H, $C_{1-6}$alkyl, $C_{2-6}$alkenyl, $C_{2-6}$alkynyl, $C_{3-8}$carbocyclyl, and heterocyclyl, wherein each $C_{1-6}$alkyl, $C_{2-6}$alkenyl, $C_{2-6}$alkynyl, $C_{3-8}$carbocyclyl, and heterocyclyl is optionally substituted with one or more groups $R^x$; or two $R^g$ groups together with the nitrogen to which they are attached form a 3-6 membered heterocycle;

each $R^m$ is independently selected from H, $C_{1-6}$alkyl, $C_{2-6}$alkenyl, $C_{2-6}$alkynyl, $C_{1-6}$haloalkyl, carbocyclyl, $C_{1-6}$ alkanoyl, phenyl, and benzyl, wherein any $C_{1-6}$alkyl, $C_{2-6}$alkenyl, $C_{2-6}$alkynyl, $C_{1-6}$ haloalkyl, carbocyclyl, $C_{1-6}$ alkanoyl, phenyl, or benzyl is optionally substituted with one or more groups independently selected from halo, —CN, —NO$_2$, —NR$^y$R$^z$, and —OR$^w$; or two $R^m$ groups together with the nitrogen to which they are attached form a 3-6 membered heterocycle;

A is a pyrazole, imidazole, oxadiazole, or isoxazole ring, which pyrazole, imidazole, oxadiazole, or isoxazole ring is substituted with $R^4$ and which pyrazole, imidazole, oxadiazole, or isoxazole ring is also optionally substituted with one or more groups independently selected from halo, nitro, cyano, $C_{1-6}$alkyl, $C_{2-6}$alkenyl, $C_{2-6}$alkynyl, $C_{1-6}$haloalkyl, $C_{1-6}$alkoxy, $C_{1-6}$ alkanoyl, $C_{1-6}$alkanoyloxy, $C_{1-6}$alkoxycarbonyl, carbocyclyl, and —N(R$^t$)$_2$;

each $R^t$ is independently selected from H, $C_{1-6}$alkyl, $C_{2-6}$alkenyl, $C_{2-6}$alkynyl, $C_{3-8}$ carbocyclyl, and heterocyclyl, wherein each $C_{1-6}$alkyl, $C_{2-6}$alkenyl, $C_{2-6}$alkynyl, $C_{3-8}$carbocyclyl, and heterocyclyl is optionally substituted with one or more groups $R^x$; or two $R^t$ groups together with the nitrogen to which they are attached form a 3-6 membered heterocycle;

each $R^v$ is independently hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from oxo, halo, amino, hydroxyl, and $C_1$-$C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^w$ is independently selected from H, $C_{1-4}$alkyl, $C_{1-4}$alkanoyl, phenyl, benzyl, and phenethyl;

each $R^x$ is independently selected from oxo, $C_{1-6}$alkyl, $C_{2-6}$alkenyl, $C_{2-6}$alkynyl, $C_{1-6}$ haloalkyl, carbocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —S—C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —S(O)$_2$—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, $C_{1-6}$haloalkyl and carbocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —S(O)$_2$—N(R$^v$)$_2$, —N(R$^v$)—C(O)—R$^v$, —N(R$^v$)—S(O)—R$^v$—N(R$^v$)—S(O)$_2$—R$^v$ and $C_{1-6}$alkyl that is optionally substituted with one or more groups independently selected from oxo and halo; and each $R^y$ and $R^z$ is independently selected from H, $C_{1-4}$alkyl, $C_{1-4}$alkanoyl, $C_{1-4}$ alkoxycarbonyl, phenyl, benzyl, and phenethyl, or $R^y$ and $R^z$ together with the nitrogen to which they are attached form a heterocyclyl; or a salt thereof.

2. A compound of formula (I):

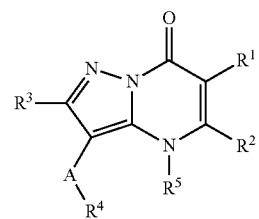

wherein:

$R^1$ and $R^2$ are each independently H, $C_{1-12}$alkyl, $C_{2-12}$alkenyl, $C_{2-12}$alkynyl, carbocyclyl, heterocyclyl, halo, —OR$^a$, —SR$^a$, —N(R$^a$)$_2$, —CN, —NO$_2$, —C(O)R$^a$, —CO$_2$R$^a$, —C(O)N(R$^a$)$_2$, —C(O)SR$^a$, —C(O)C(O)R$^a$, —C(O)CH$_2$C(O)R$^a$, —C(S)N(R$^a$)$_2$, —C(S)OR$^a$, —S(O)R$^a$, —SO$_2$R$^a$, —SO$_2$N(R$^a$)$_2$, —N(R$^a$)C(O)R$^a$, —N(R$^a$)C(O)N(R$^a$)$_2$, —N(R$^a$)SO$_2$R$^a$, —N(R$^a$)SO$_2$N(R$^a$)$_2$, —N(R$^a$)N(R$^a$)$_2$, —N(R$^a$)C(=N(R$^a$))N(R$^a$)$_2$, —C=NOR$^a$, —C(=N(R$^a$))N(R$^a$)$_2$, —OC(O)R$^a$, or —OC(O)N(R$^a$)$_2$, wherein each $C_{1-12}$alkyl, $C_{2-12}$alkenyl, $C_{2-12}$alkynyl, carbocyclyl, and heterocyclyl of $R^1$ and $R^2$ is independently optionally substituted with one or more groups R$^x$; and wherein R$^1$ and R$^2$ are not each H; or R$^1$ and R$^2$ taken together with the atoms to which they are attached form a 4, 5, 6, 7, or 8 membered carbocyclyl, which carbocyclyl is optionally substituted with one or more groups R$^x$;

R$^3$ is H, C$_{1-6}$alkyl, trifluoromethyl, 3-6 membered carbocyclyl, 3-6 membered heterocyclyl, halo, —OR$^f$, —SR$^f$, —N(R$^f$)$_2$, —CN, or —NO$_2$, wherein said alkyl, carbocyclyl and heterocyclyl are optionally substituted with one or more groups independently selected from oxo, halo, C$_{1-3}$alkoxy and C$_{1-3}$alkyl;

R$^5$ is H, C$_{1-12}$alkyl, C$_{2-12}$alkenyl, C$_{2-12}$alkynyl, carbocyclyl, and heterocyclyl, wherein each C$_{1-12}$alkyl, C$_{2-12}$alkenyl, C$_{2-12}$alkynyl, carbocyclyl, and heterocyclyl is optionally substituted with one or more groups independently selected from oxo, C$_{1-12}$ alkyl, C$_{1-12}$haloalkyl, carbocyclyl, heterocyclyl, halo, —CN, —NO$_2$, —NR$^m$R$^m$, —OR$^m$, —C(=O)OR$^m$, and —OC(=O)R$^m$; or R$^5$ and R$^2$ taken together with the atoms to which they are attached form a heterocyclyl;

each R$^a$ is independently selected from H, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, and heterocyclyl is optionally substituted with one or more groups R$^x$;

each R$^f$ is independently selected from H, C$_{1-3}$ alkyl, trifluoromethyl, 3-6 membered carbocyclyl, and 3-6 membered heterocyclyl; or two R$^f$ groups together with the nitrogen to which they are attached form a 3-6 membered heterocycle;

each R$^g$ is independently selected from H, C$_{1-6}$alkyl, C$_{2-6}$alkenyl, C$_{2-6}$alkynyl, C$_{3-8}$carbocyclyl, and heterocyclyl, wherein each C$_{1-6}$alkyl, C$_{2-6}$alkenyl, C$_{2-6}$alkynyl, C$_{3-8}$ carbocyclyl, and heterocyclyl is optionally substituted with one or more groups R$^x$; or two R$^g$ groups together with the nitrogen to which they are attached form a 3-6 membered heterocycle;

each R$^m$ is independently selected from H, C$_{1-6}$alkyl, C$_{2-6}$alkenyl, C$_{2-6}$alkynyl, C$_{1-6}$haloalkyl, carbocyclyl, C$_{1-6}$ alkanoyl, phenyl, and benzyl, wherein any C$_{1-6}$alkyl, C$_{2-6}$alkenyl, C$_{2-6}$alkynyl, C$_{1-6}$ haloalkyl, carbocyclyl, C$_{1-6}$ alkanoyl, phenyl, or benzyl is optionally substituted with one or more groups independently selected from halo, —CN, —NO$_2$, —NR$^y$R$^z$, and —OR$^w$; or two R$^m$ groups together with the nitrogen to which they are attached form a 3-6 membered heterocycle;

each R$^v$ is independently hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, and heterocyclyl is optionally substituted with one or more groups independently selected from oxo, halo, amino, hydroxyl, and C$_1$-C$_6$ alkyl that is optionally substituted with one or more groups independently selected from oxo and halo; or two R$^v$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^w$ is independently selected from H, C$_{1-4}$alkyl, C$_{1-4}$alkanoyl, phenyl, benzyl, and phenethyl;

each R$^x$ is independently selected from oxo, C$_{1-6}$alkyl, C$_{2-6}$alkenyl, C$_{2-6}$alkynyl, C$_{1-6}$haloalkyl, carbocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —S(O)$_2$—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any C$_{1-6}$alkyl, C$_{2-6}$alkenyl, C$_{2-6}$alkynyl, C$_{1-6}$haloalkyl and carbocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —S(O)$_2$—N(R$^v$)$_2$, —N(R$^v$)—C(O)—R$^v$, —N(R$^v$)—S(O)—R$^v$—N(R$^v$)—S(O)$_2$—R$^v$ and C$_{1-6}$alkyl that is optionally substituted with one or more groups independently selected from oxo and halo; and each R$^y$ and R$^z$ is independently selected from H, C$_{1-4}$alkyl, C$_{1-4}$alkanoyl, C$_{1-4}$alkoxycarbonyl, phenyl, benzyl, and phenethyl, or R$^y$ and R$^z$ together with the nitrogen to which they are attached form a heterocyclyl; or a salt thereof wherein -A-R$^4$ taken together is selected from:

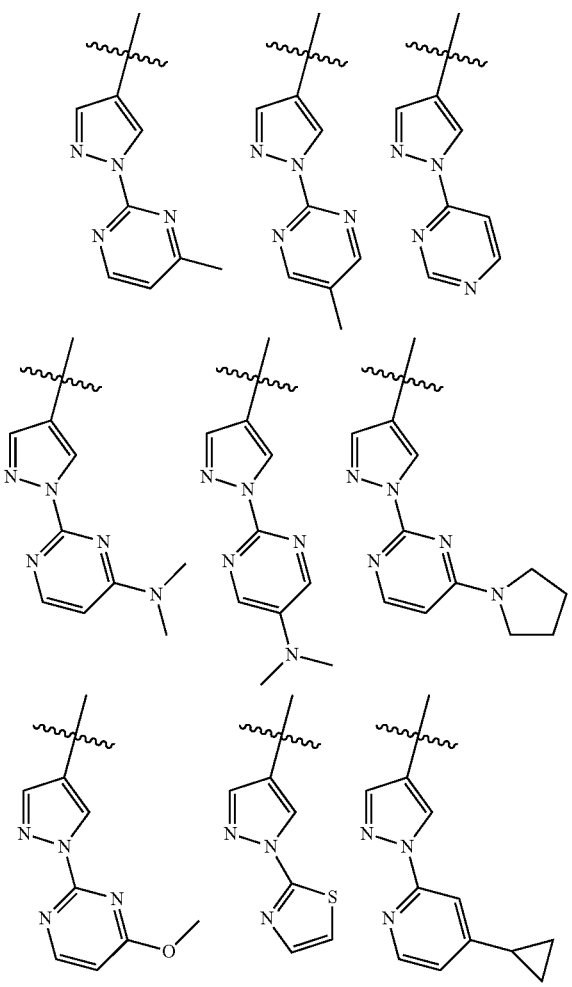

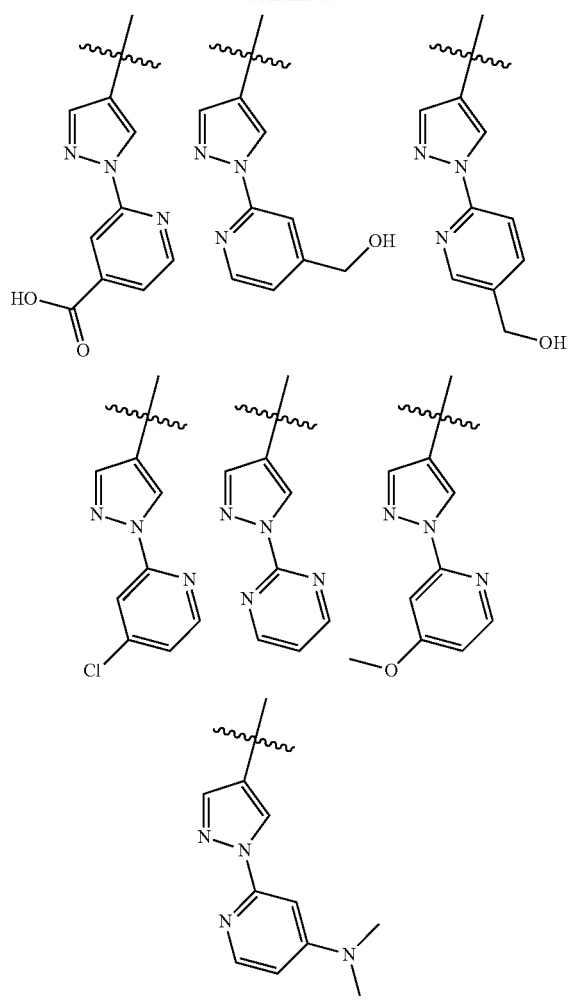
3. A compound selected from:
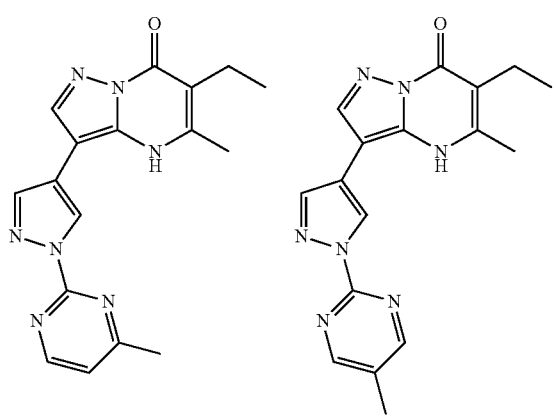
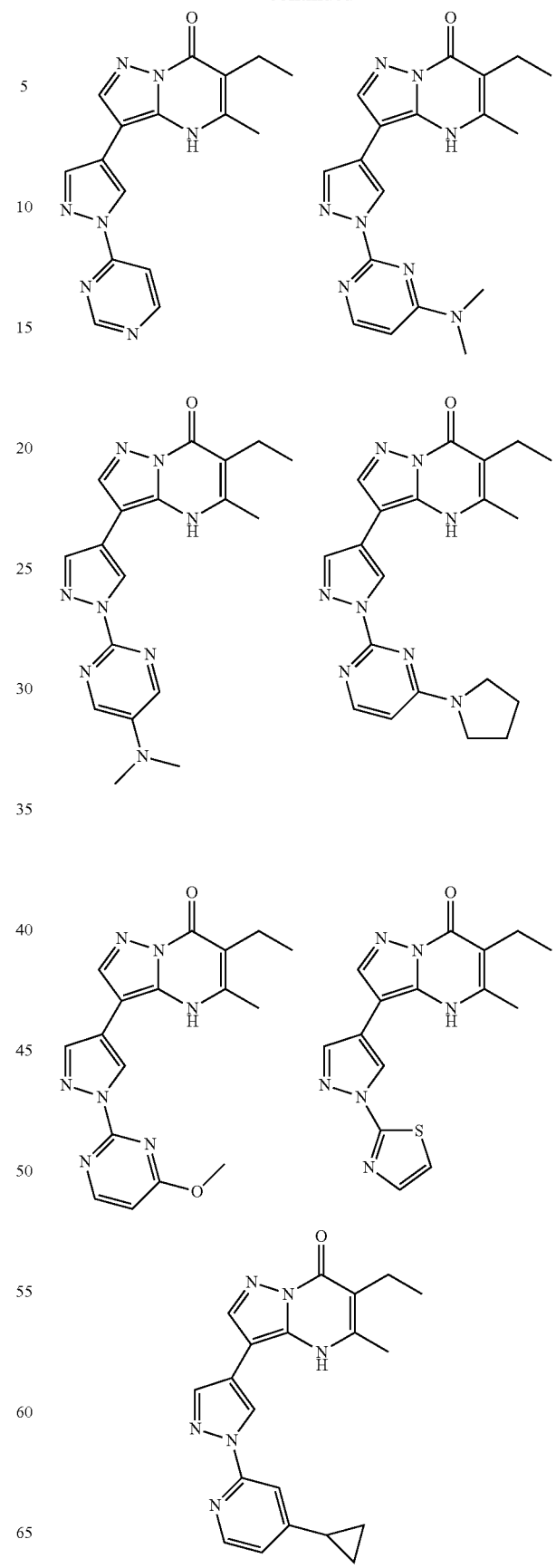

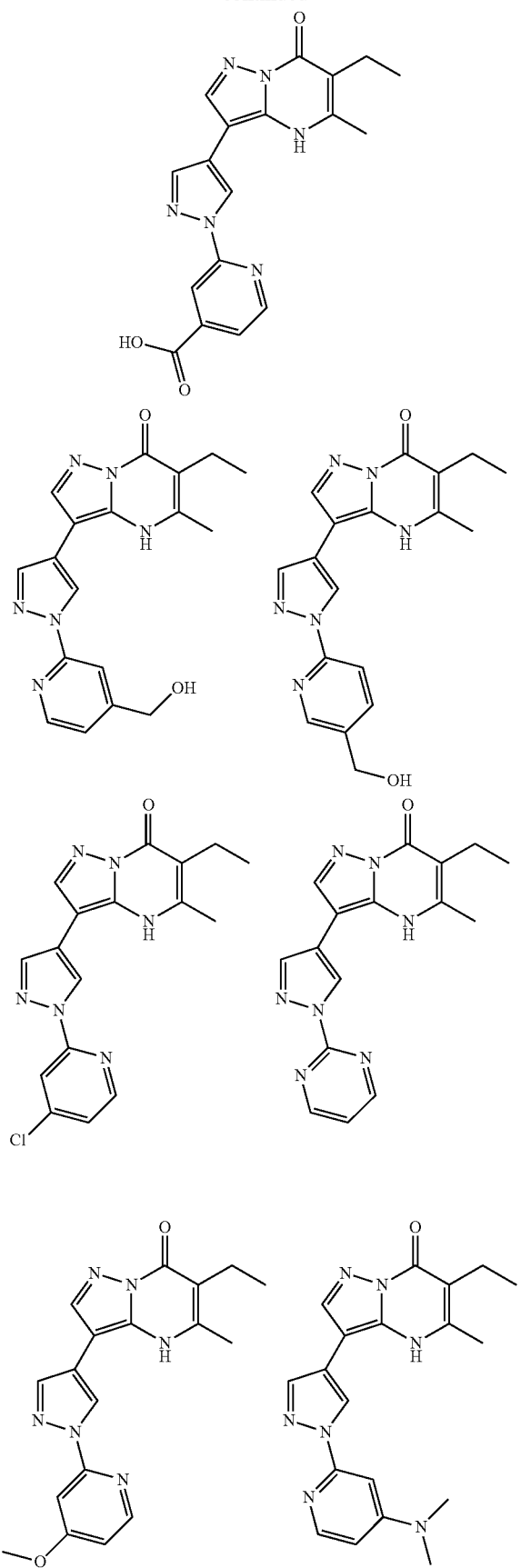
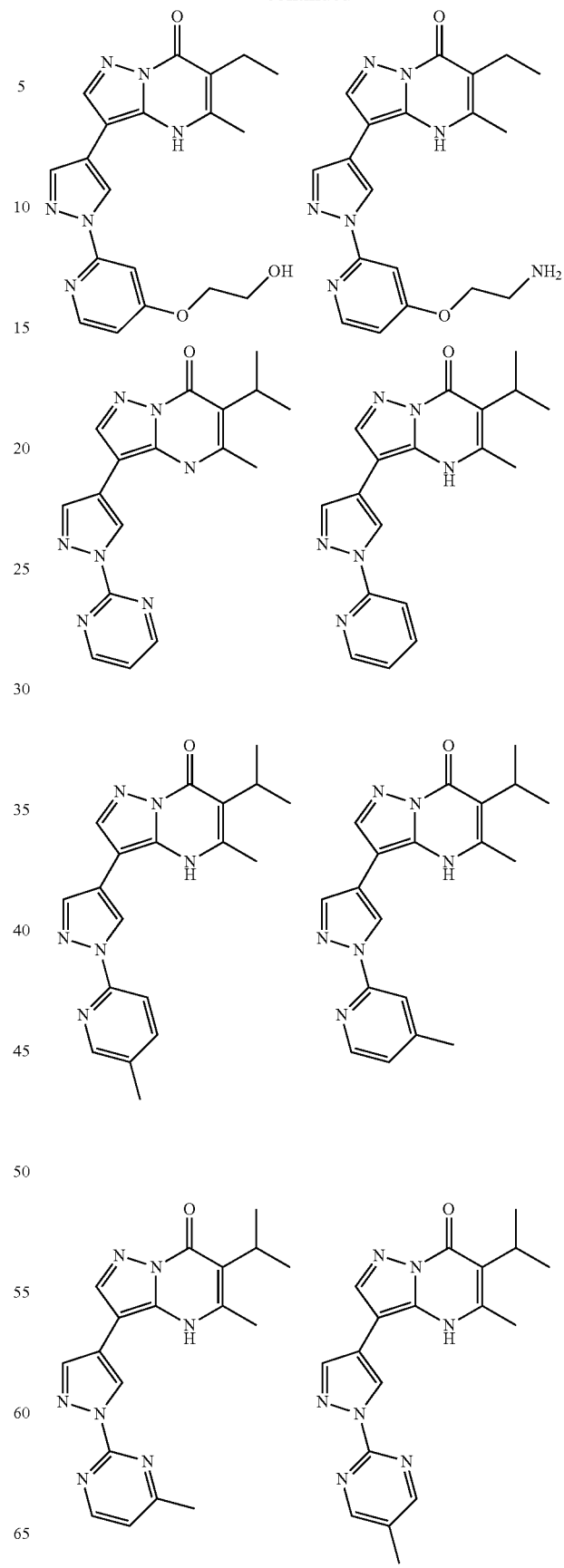

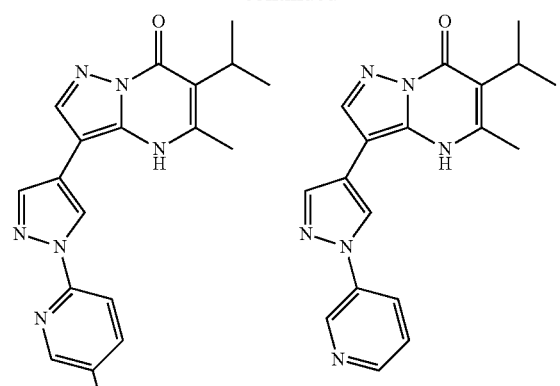
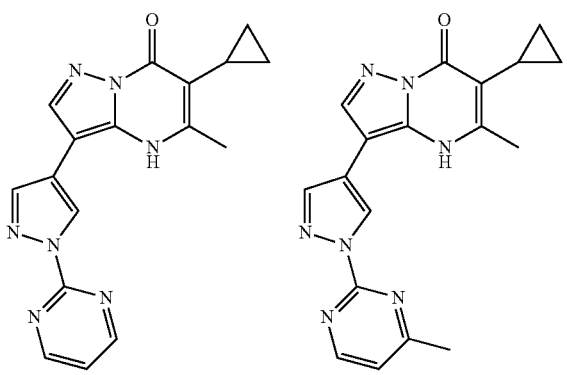
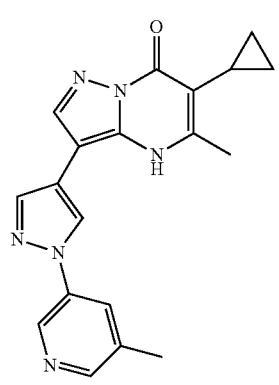
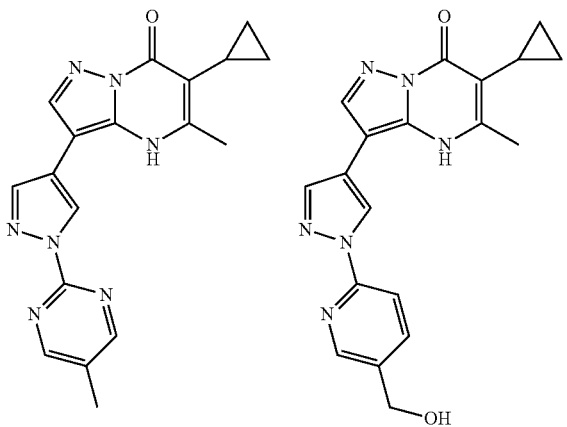
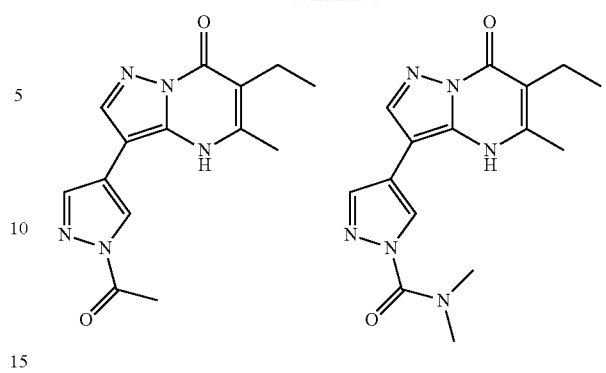
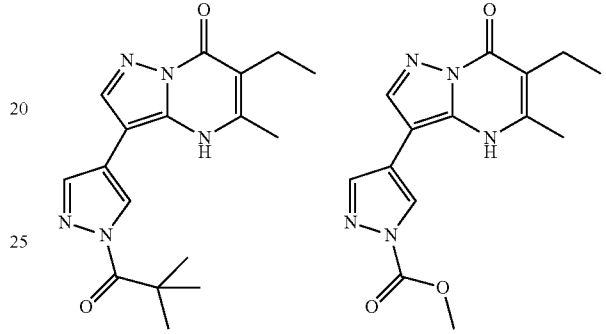
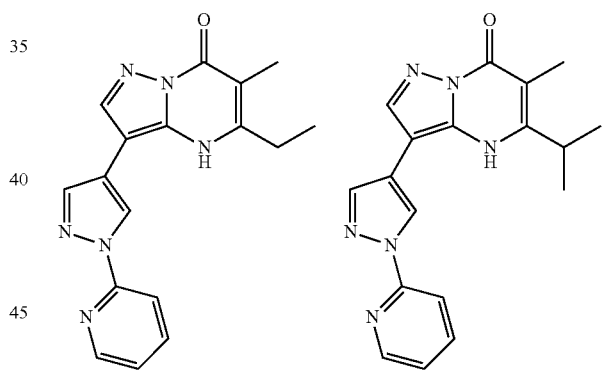
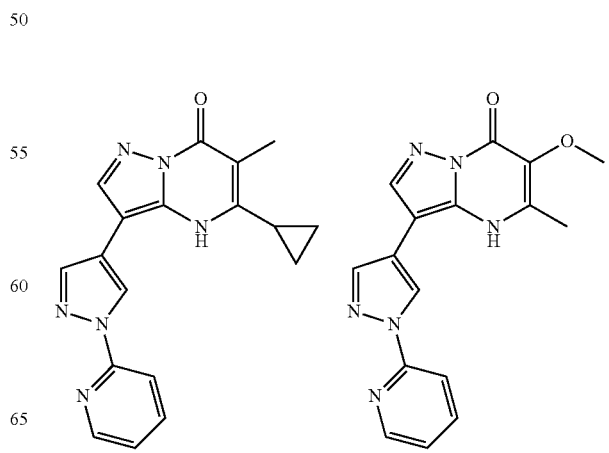

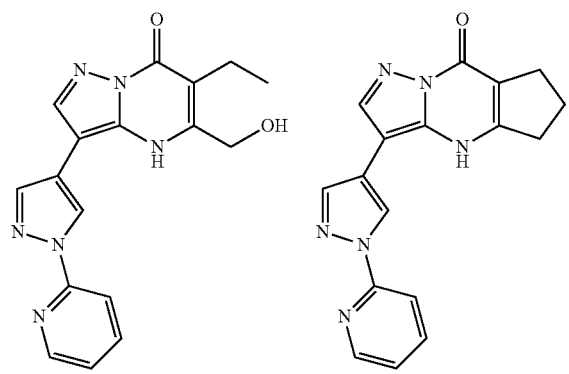
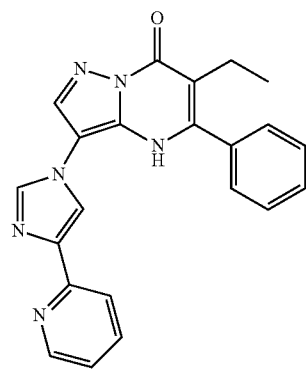
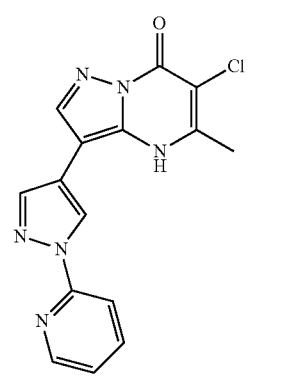
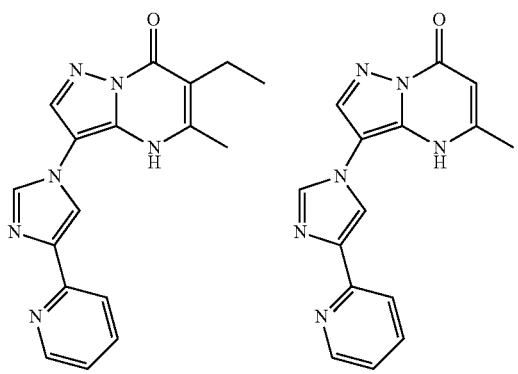
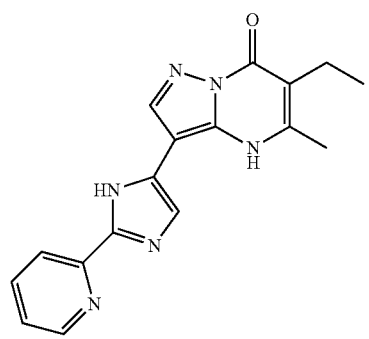
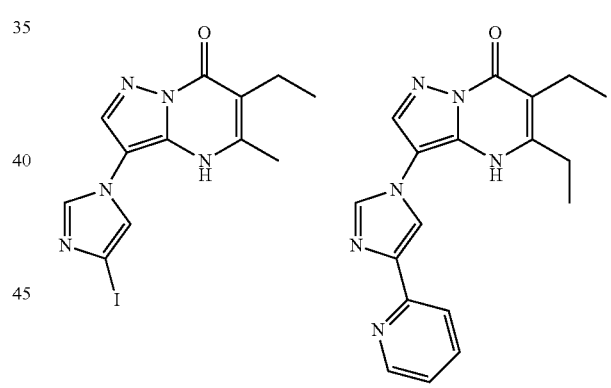
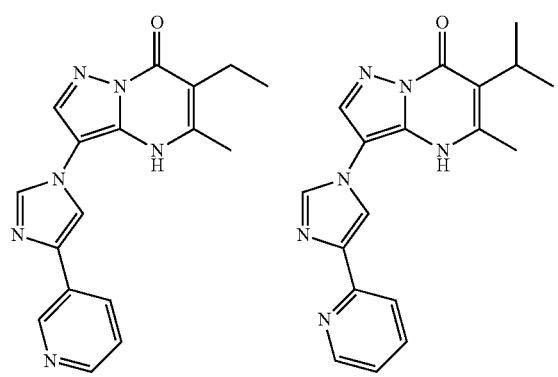
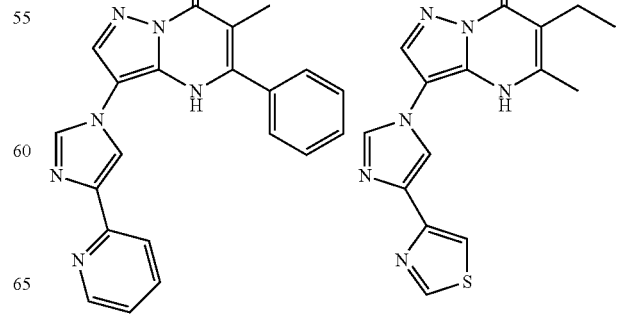

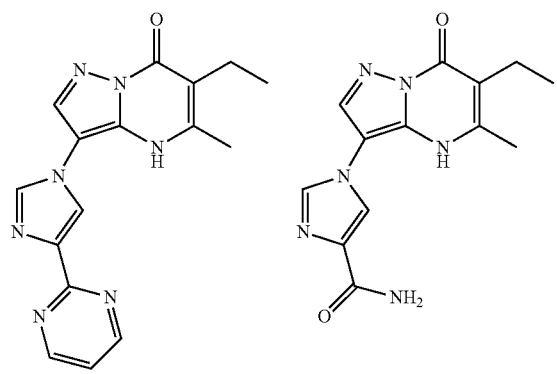
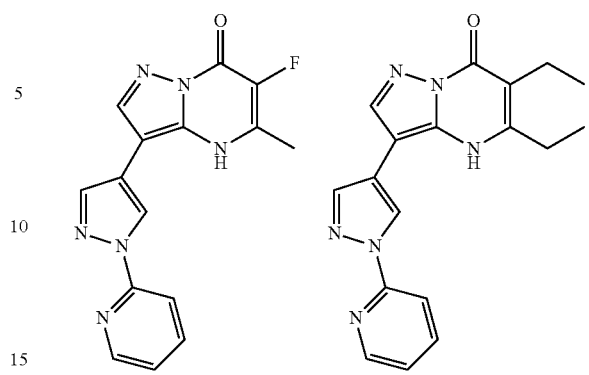
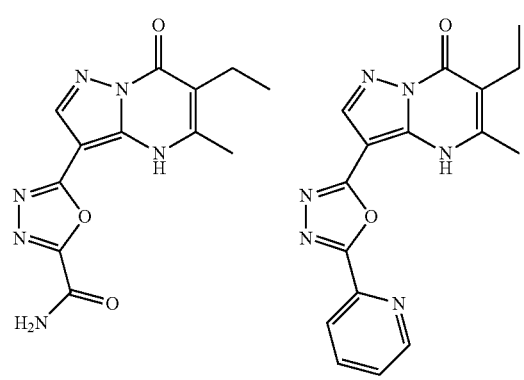
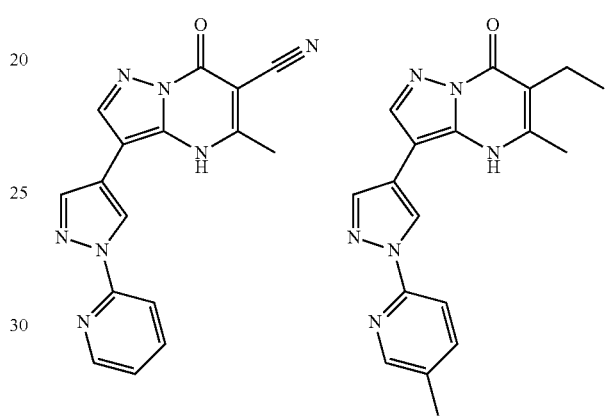
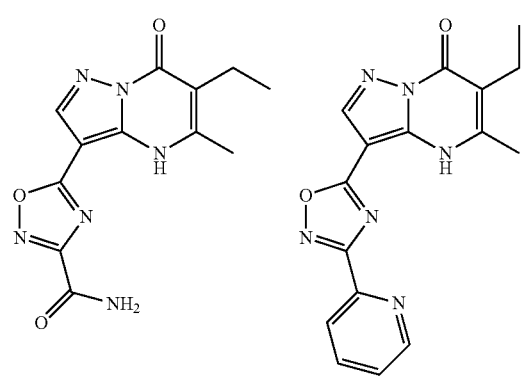
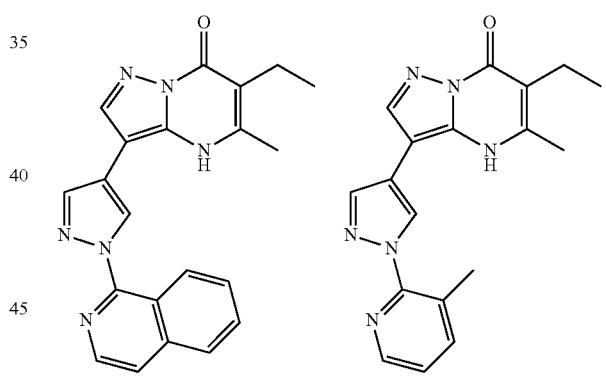
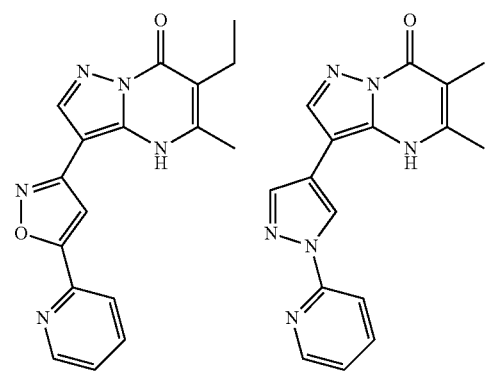
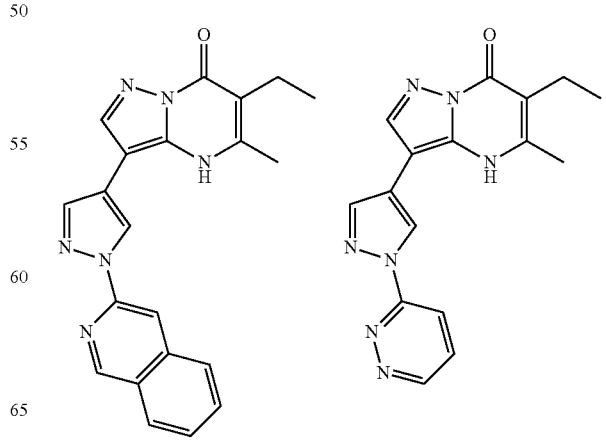

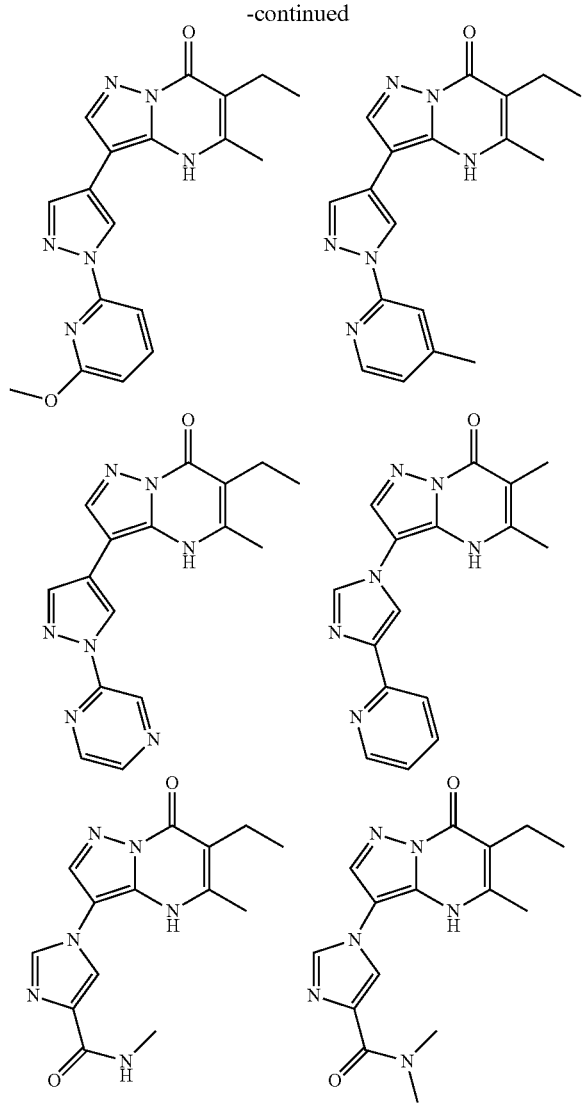
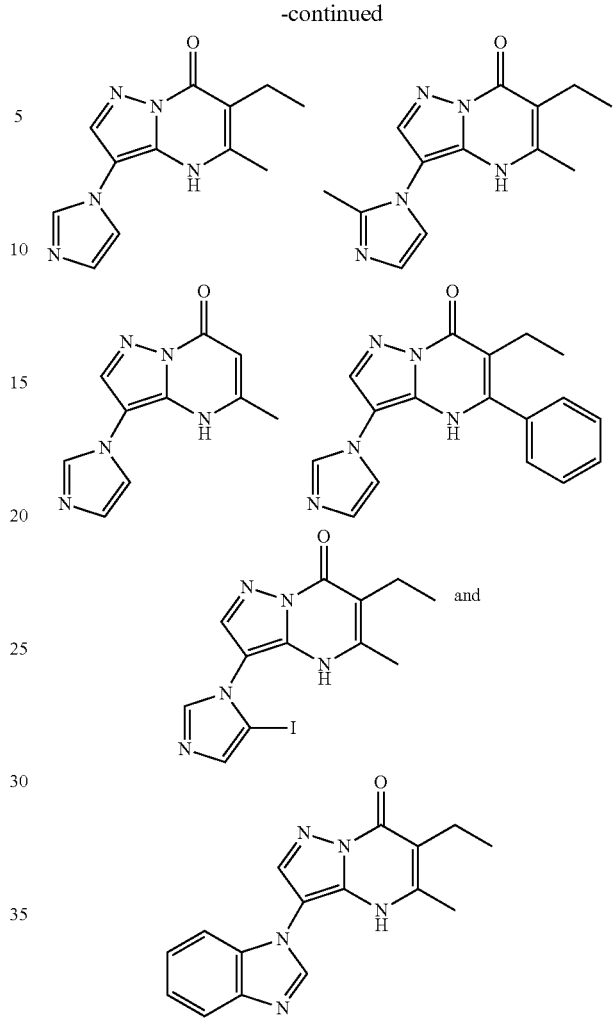
and pharmaceutically acceptable salts thereof.
* * * * *

UNITED STATES PATENT AND TRADEMARK OFFICE
CERTIFICATE OF CORRECTION

PATENT NO. : 9,505,767 B2
APPLICATION NO. : 14/477566
DATED : November 29, 2016
INVENTOR(S) : Brian K. Albrecht et al.

Page 1 of 1

It is certified that error appears in the above-identified patent and that said Letters Patent is hereby corrected as shown below:

In the Claims

Column 185, Lines 15-33, please delete " 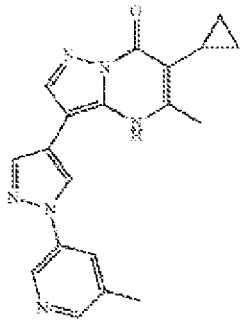 " and insert -- 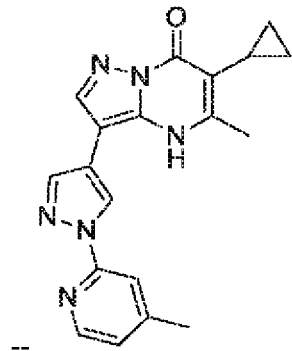 -- therefor.

Signed and Sealed this
Eighteenth Day of April, 2017

Michelle K. Lee
*Director of the United States Patent and Trademark Office*